United States Patent
Tanabe et al.

(10) Patent No.: US 11,286,454 B2
(45) Date of Patent: Mar. 29, 2022

(54) PLURIPOTENT STEM CELL MANUFACTURING SYSTEM AND METHOD FOR PRODUCING INDUCED PLURIPOTENT STEM CELLS

(71) Applicants: I PEACE, INC., Palo Alto, CA (US); Koji Tanabe, Palo Alto, CA (US)

(72) Inventors: Koji Tanabe, Palo Alto, CA (US); Brendan Kelly, Palo Alto, CA (US); Kenta Suto, Palo Alto, CA (US)

(73) Assignee: I PEACE, INC., Palo Alto, CA (US)

( * ) Notice: Subject to any disclaimer, the term of this patent is extended or adjusted under 35 U.S.C. 154(b) by 231 days.

(21) Appl. No.: 15/756,029

(22) PCT Filed: Aug. 30, 2016

(86) PCT No.: PCT/US2016/049530
§ 371 (c)(1),
(2) Date: Feb. 27, 2018

(87) PCT Pub. No.: WO2017/040548
PCT Pub. Date: Mar. 9, 2017

(65) Prior Publication Data
US 2018/0273891 A1    Sep. 27, 2018

Related U.S. Application Data

(60) Provisional application No. 62/356,199, filed on Jun. 29, 2016.

(30) Foreign Application Priority Data

Aug. 31, 2015    (JP) .............................. JP2015-170797

(51) Int. Cl.
| | |
|---|---|
| C12M 1/36 | (2006.01) |
| C12M 1/00 | (2006.01) |
| C12M 1/34 | (2006.01) |
| C12M 1/33 | (2006.01) |
| C12M 1/42 | (2006.01) |
| C12N 5/078 | (2010.01) |
| C12M 3/00 | (2006.01) |
| C12M 1/02 | (2006.01) |
| C12M 1/12 | (2006.01) |
| C12N 5/074 | (2010.01) |

(52) U.S. Cl.
CPC ............ *C12M 41/48* (2013.01); *C12M 23/28* (2013.01); *C12M 23/44* (2013.01); *C12M 27/00* (2013.01); *C12M 29/00* (2013.01); *C12M 29/04* (2013.01); *C12M 35/00* (2013.01); *C12M 37/02* (2013.01); *C12M 41/12* (2013.01); *C12M 41/36* (2013.01); *C12M 45/02* (2013.01); *C12M 47/04* (2013.01); *C12N 5/0634* (2013.01); *C12N 5/0696* (2013.01)

(58) Field of Classification Search
CPC ...... C12M 23/28; C12M 23/44; C12M 27/00; C12M 29/00; C12M 29/04; C12M 35/00; C12M 37/02; C12M 41/12; C12M 41/36; C12M 41/48; C12M 45/02; C12M 47/04; C12N 5/0634; C12N 5/0696
See application file for complete search history.

(56) References Cited

U.S. PATENT DOCUMENTS

| | | | |
|---|---|---|---|
| 6,498,690 | B2 | 12/2002 | Ramm et al. |
| 2009/0029462 | A1 | 1/2009 | Beardsley et al. |
| 2009/0068742 | A1 | 3/2009 | Yamanaka |
| 2009/0104594 | A1 | 4/2009 | Webb |
| 2011/0281281 | A1 | 11/2011 | Irion |
| 2013/0309710 | A1 | 11/2013 | Nakamura |
| 2013/0345094 | A1 | 12/2013 | Noggle et al. |
| 2014/0106348 | A1 | 4/2014 | Nishino et al. |
| 2014/0248698 | A1 | 9/2014 | Kotera et al. |
| 2014/0329317 | A1 | 11/2014 | Nakatsuji |
| 2016/0046905 | A1 | 2/2016 | Inoue et al. |
| 2016/0060588 | A1 | 3/2016 | Nakatsuji et al. |
| 2016/0215258 | A1 | 7/2016 | Okairi et al. |
| 2016/0272929 | A1 | 9/2016 | Fuji et al. |
| 2017/0002311 | A1 | 1/2017 | Otani et al. |
| 2017/0009201 | A1 | 1/2017 | Hayashi et al. |
| 2017/0306279 | A1 | 10/2017 | Kagawa et al. |
| 2018/0127714 | A1 | 5/2018 | Ko |

FOREIGN PATENT DOCUMENTS

| | | |
|---|---|---|
| CN | 102174395 A | 9/2011 |
| EP | 2878664 | 6/2015 |
| EP | 2878664 A1 | 6/2015 |
| JP | 2005-521405 A | 7/2005 |

(Continued)

OTHER PUBLICATIONS

"Biotech Cellulose Ester (CE) Membrane: Dialysis Tubing & Dialysis Trial Kits", Spectrum Laboratories, Inc. [online], Apr. 22, 2012 [retrieved Jan. 4, 2017]. Retrieved from the Internet: URL <http://web.archive.org/web/20120422151024/http://www.spectrumlabs.com/dialysis/BiotechTubing.html>, 2 pages.

(Continued)

*Primary Examiner* — Blaine Lankford
(74) *Attorney, Agent, or Firm* — Studebaker & Brackett PC

(57) ABSTRACT

The present invention provides a stem cell manufacturing system comprising: a sending channel (20) through which a solution containing cells flows; an apparatus (30) which is connected to the sending channel (20) and transfers a pluripotency inducer into the cells to produce cells harboring the inducer; and an apparatus (40) which cultures the cells harboring the inducer to produce cell clusters consisting of stem cells.

8 Claims, 46 Drawing Sheets
Specification includes a Sequence Listing.

(56) References Cited

FOREIGN PATENT DOCUMENTS

| | | |
|---|---|---|
| JP | 2006-014693 A | 1/2006 |
| JP | 2007-000038 A | 1/2007 |
| JP | 2008-526203 A | 7/2008 |
| JP | 4183742 B1 | 11/2008 |
| JP | 2010-532173 A | 10/2010 |
| JP | 2012-528599 | 11/2012 |
| JP | 2015-092849 A | 5/2015 |
| JP | 2015-522257 A | 8/2015 |
| WO | 2003-083092 | 10/2003 |
| WO | 2003083092 A1 | 10/2003 |
| WO | WO 2009/096614 A1 | 8/2009 |
| WO | 2010-141801 | 12/2010 |
| WO | 2010141801 A2 | 12/2010 |
| WO | WO 2012/115153 A1 | 8/2012 |
| WO | WO 2013/077423 A1 | 5/2013 |
| WO | WO 2013/094365 A1 | 6/2013 |
| WO | WO 2013/136372 A1 | 9/2013 |
| WO | 2013-188679 A | 12/2013 |
| WO | 2014-072061 A | 5/2014 |
| WO | 2016-143826 A | 9/2014 |
| WO | WO 2014/136581 A1 | 9/2014 |
| WO | WO 2014/144789 A2 | 9/2014 |
| WO | WO2015/033558 A1 | 3/2015 |
| WO | WO2015/111685 A1 | 7/2015 |
| WO | WO2015/111686 A1 | 7/2015 |
| WO | 2014-017513 A | 7/2016 |
| WO | WO 2016/117615 A1 | 7/2016 |
| WO | 2014148646 A | 2/2017 |

OTHER PUBLICATIONS

Chanda et al., "Generation of Induced Neuronal Cells by the Single Reprogramming Factor ASCL1", Stem Cell Reports. Aug. 12, 2014;3(2):282-96. Epub Jul. 4, 2014.

Fusaki et al., "Efficient induction of transgene-free human pluripotent stem cells using a vector based on Sendai virus, an RNA virus that does not integrate into the host genome", Proc Jpn Acad Ser B Phys Biol Sci. 2009;85(8):348-62.

Hacein-Bey-Abina et al., "LMO2-Associated Clonal T Cell Proliferation in Two Patients after Gene Therapy for SCID-X1", Science. Oct. 17, 2003;302(5644):415-9.

Hacein-Bey-Abina et al., "Sustained correction of X-linked severe combined immunodeficiency by ex vivo gene therapy", N Engl J Med. Apr. 18, 2002;346(16):1185-93.

Hamot et al., "Method validation for automated isolation of viable peripheral blood mononuclear cells", Biopreserv Biobank. Jun. 2015;13(3):152-63. Epub Apr. 1, 2015.

Ishii et al., "Novel cultivation method development for suspension culture of pluripotent stem cell", BIO Clinica. May 2015;30(5):82-86.

"Lipofectamine® MessengerMAX™", Thermo Fisher Scientific [online], Aug. 25, 2015 [retrieved Jan. 3, 2017]. Retrieved from the Internet: URL <http://web.archive.org/web/20150825014508/http://www.thermofisher.com/us/en/home/brands/product-brand/lipofectamine/lipofectamine-messengermax.html>, 5 pages.

Ohnuki et al., "Dynamic regulation of human endogenous retroviruses mediates factor-induced reprogramming and differentiation potential", Proc Natl Acad Sci U S A. Aug. 26, 2014;111(34):12426-31. Epub Aug. 5, 2014.

Okita et al., "Generation of germline-competent induced pluripotent stem cells", Nature. Jul. 19, 2007;448(7151):313-7. Epub Jun. 6, 2007.

Osafune et al., "Marked differences in differentiation propensity among human embryonic stem cell lines", Nat Biotechnol. Mar. 2008;26(3):313-5. Epub Feb. 17, 2008.

Ujam et al., "Isolation of monocytes from human peripheral blood using immuno-affinity expanded-bed adsorption", Biotechnol Bioeng. Sep. 5, 2003;83(5):554-66.

Yu et al., "Human Induced Pluripotent Stem Cells Free of Vector and Transgene Sequences", Science. May 8, 2009;324(5928):797-801. Epub Mar. 26, 2009.

Osakada et al., "In vitro differentiation of retinal cells from human pluripotent stem cells by small-molecule induction", J Cell Sci. Sep. 1, 2009; 122(Pt 17): 3169-3179. Epub Aug. 11, 2009.

STEMCELL Technologies Inc., "TeSR™", 2019, accessed on Nov. 27, 2019, URL: www.stemcell.com/products/brands/tesr-es-ips-feeder-free-media.html.

Bohmann et al, "Performance of a membrane-dialysis bioreactor with a radial-flow fixed bed for the cultivation of a hybridoma cell line", Appl Microbiol Biotechnol. Oct. 1995; 43(5): 772-780.

CELLine Bioreactors: Membane Culture Flasks for Antibody and Protein Reduction. Datasheet [online], Wheaton. Jun. 2012. Retrieved from the Internet: <URL: www.wheaton.com>, 1 page.

Xu, C., "High-Density Cell Microarrays for Parallel Functional Determinations", Genome Res. Mar. 2002; 12(3): 482-486.

TeSR—Feeder-Free Media for Human ES and iPS Cell Culture; STEMCELL Technologies; Nov. 27, 2019; https://www.stemcell.com/products/brands/tesr-es-ips-feeder-free-media.html—pp. 1-5.

dish@cellculturedish.com; "Ask the Expert Session Got mRNA? Solve DNA transfection issues with mRNA transfection", The Cell Culture Dish, [online], Thermo Fisher Scientific, Oct. 13, 2014 https://www.thermofisher.com/content/dam/LifeTech/global/lifesciences/ProteinExpressionAnalysis/pdfs/ask-the-Expert_101214.pdf.

[Fig. 1]
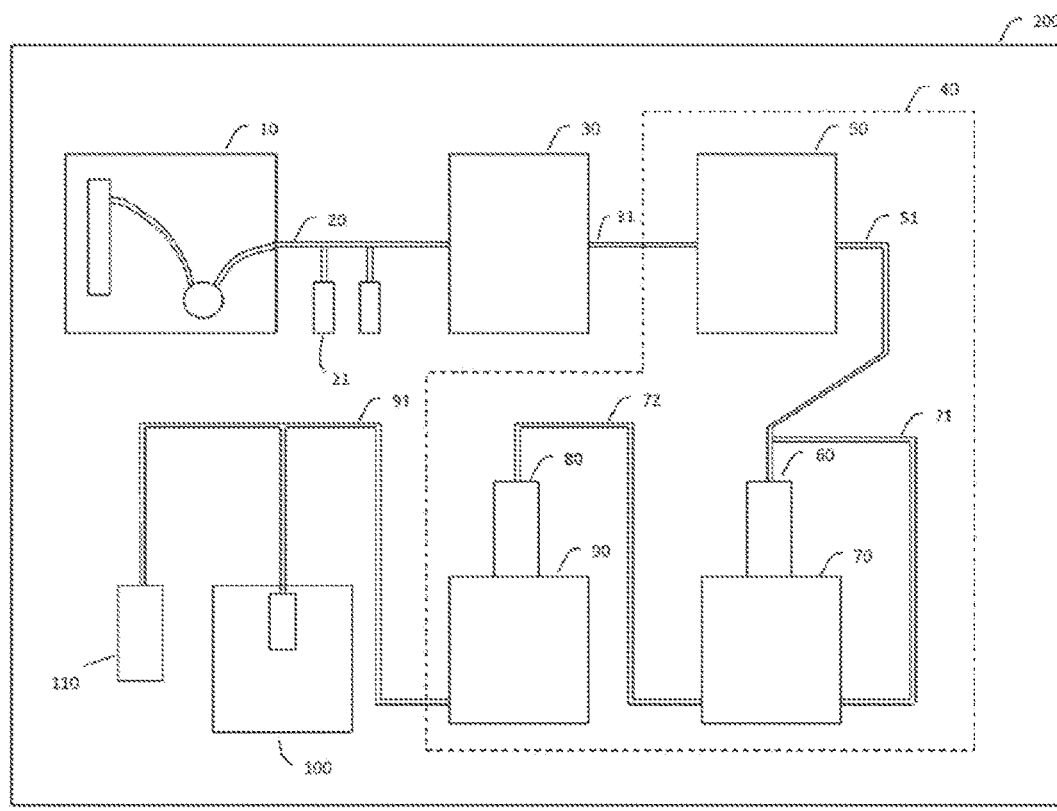

[Fig. 2]
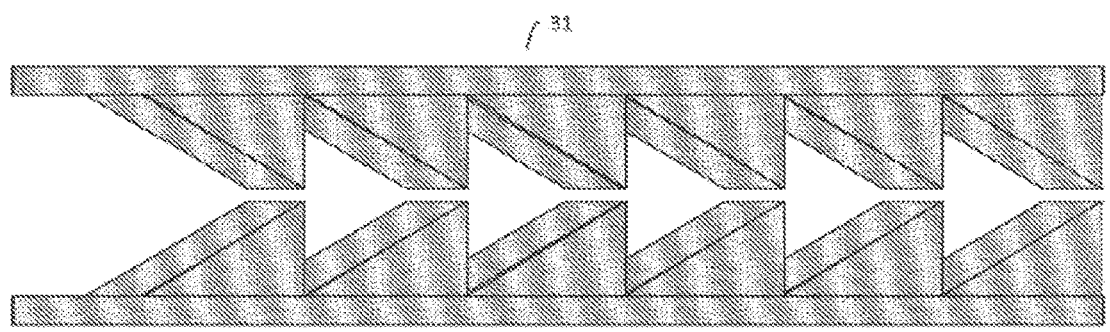

[Fig. 3]
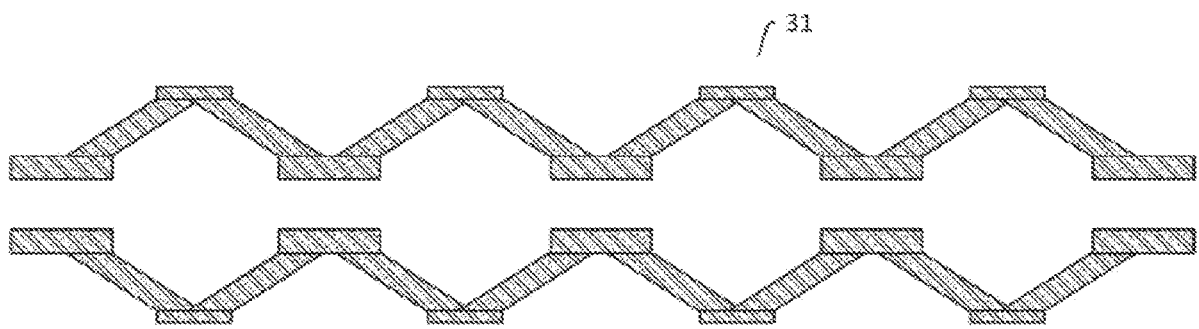

[Fig. 4]
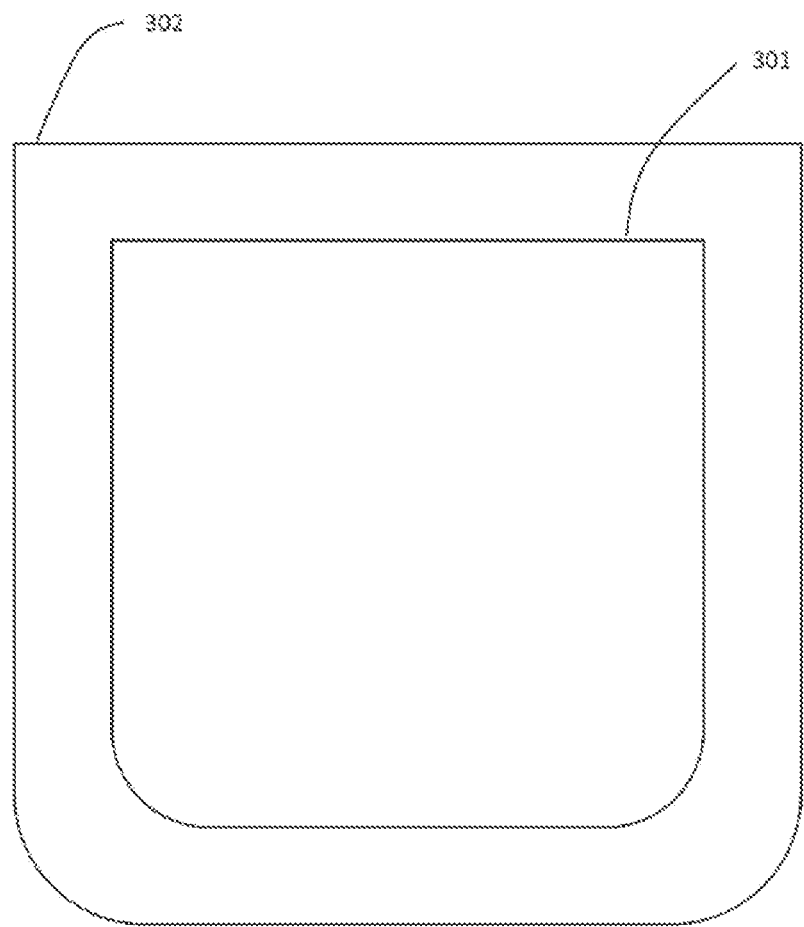

[Fig. 5]
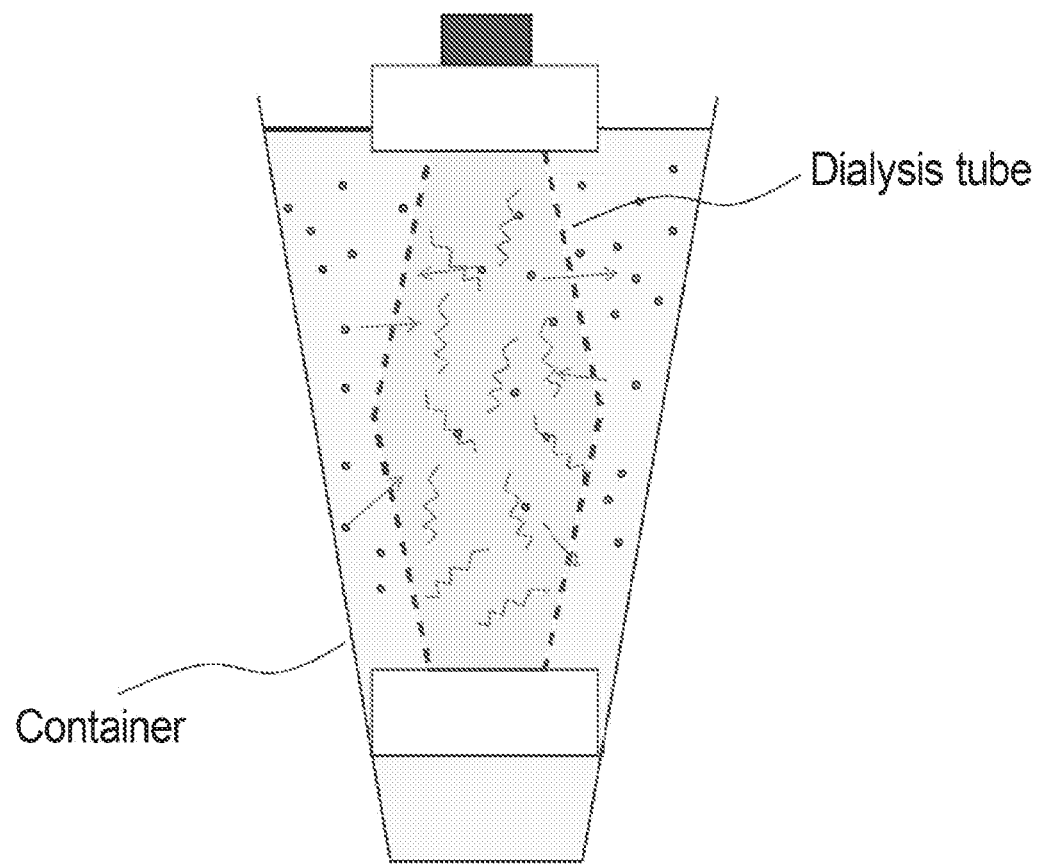

[Fig. 6]
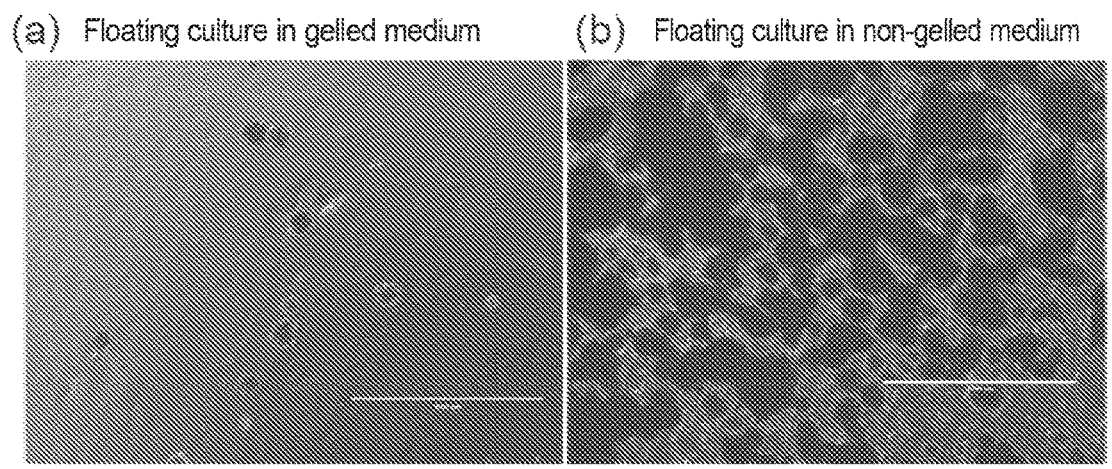

[Fig. 7]
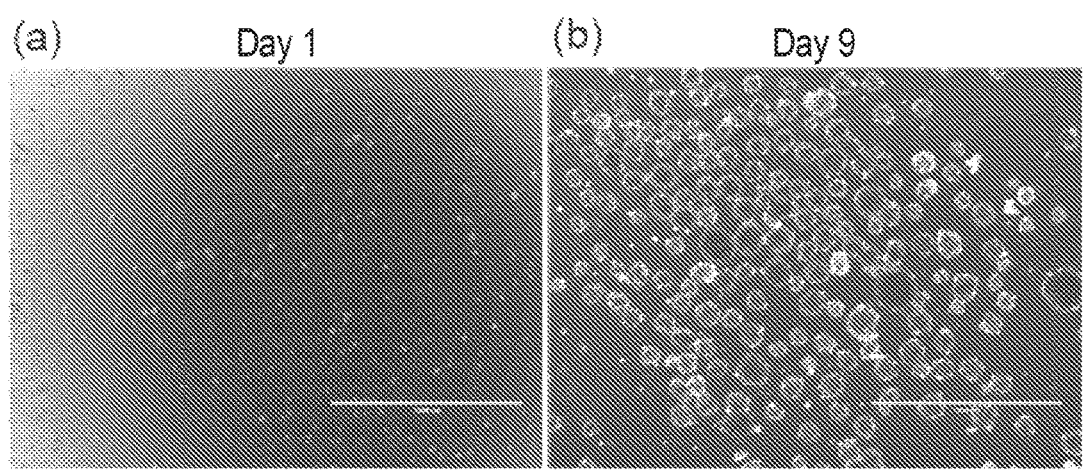

[Fig. 8]
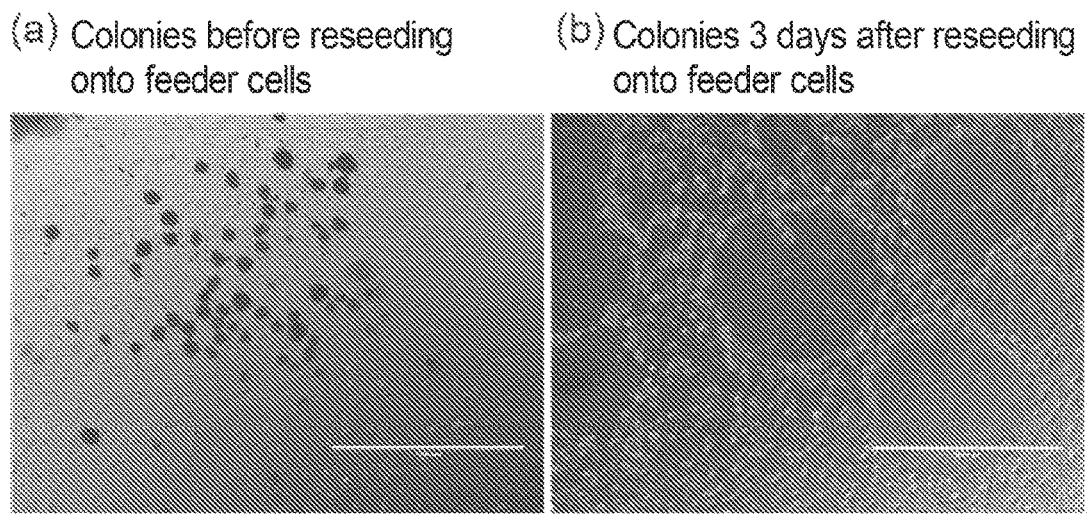

[Fig. 9]
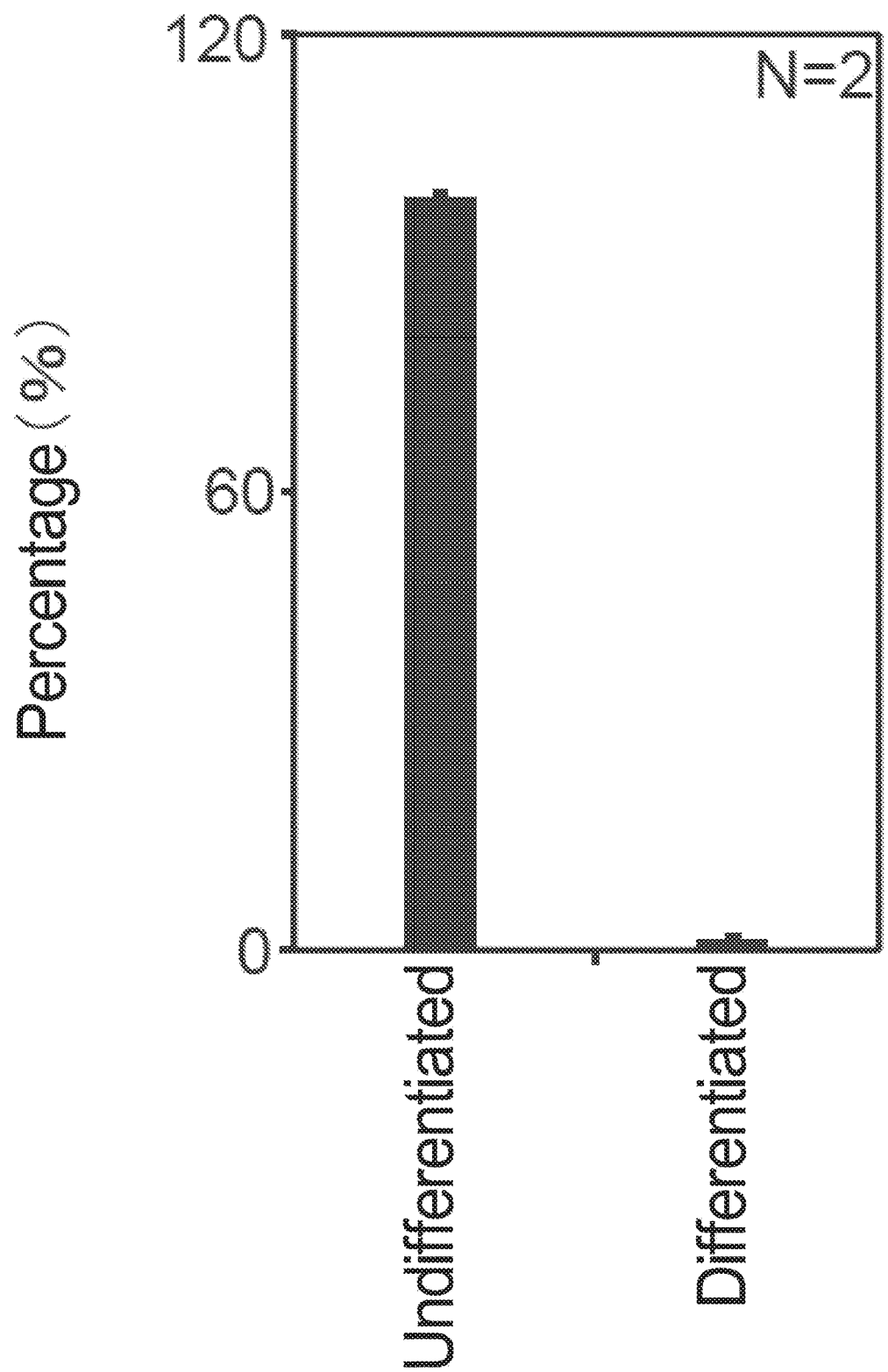

[Fig. 10]
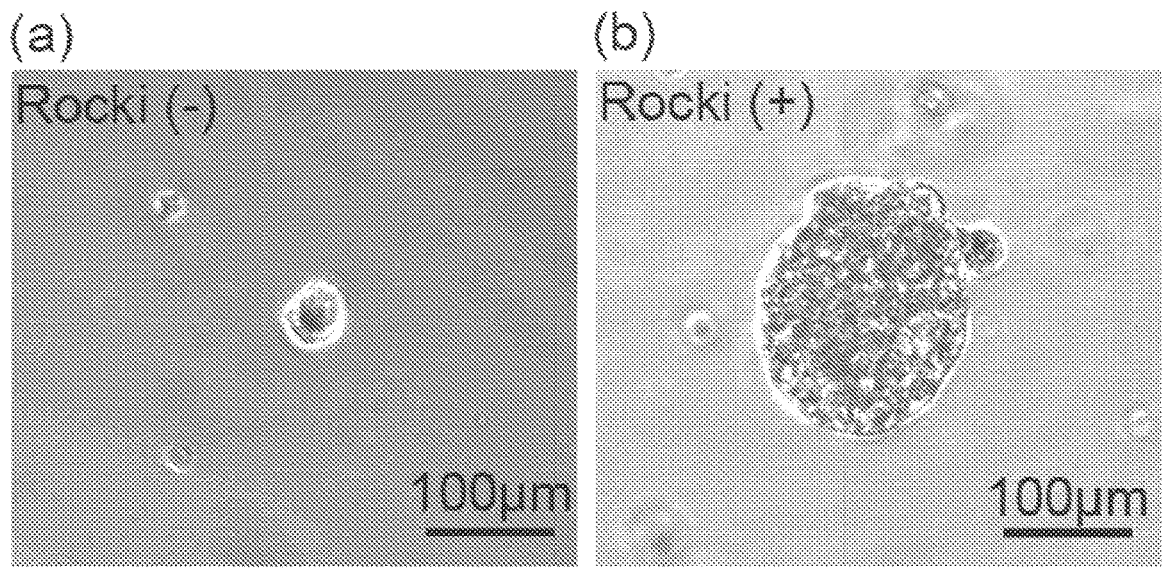

[Fig.11]
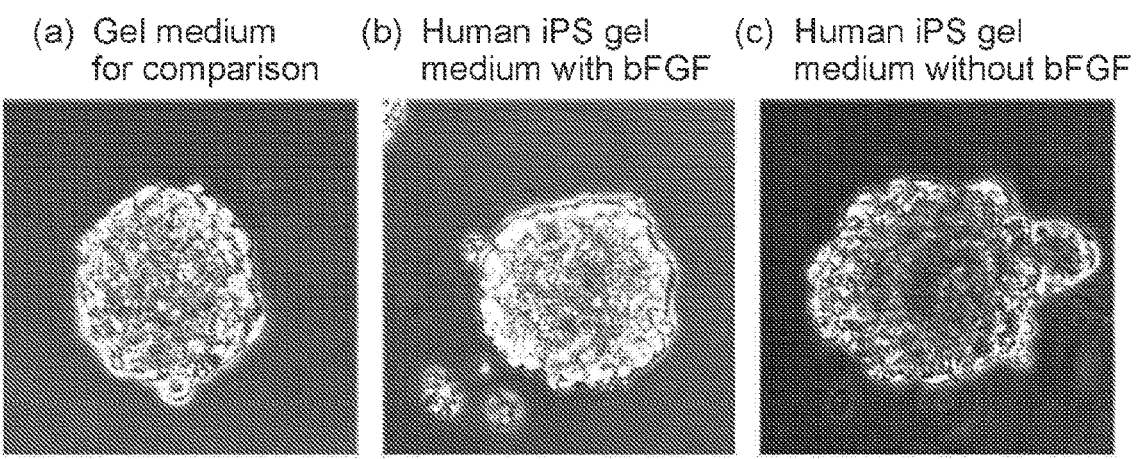

[Fig.12]
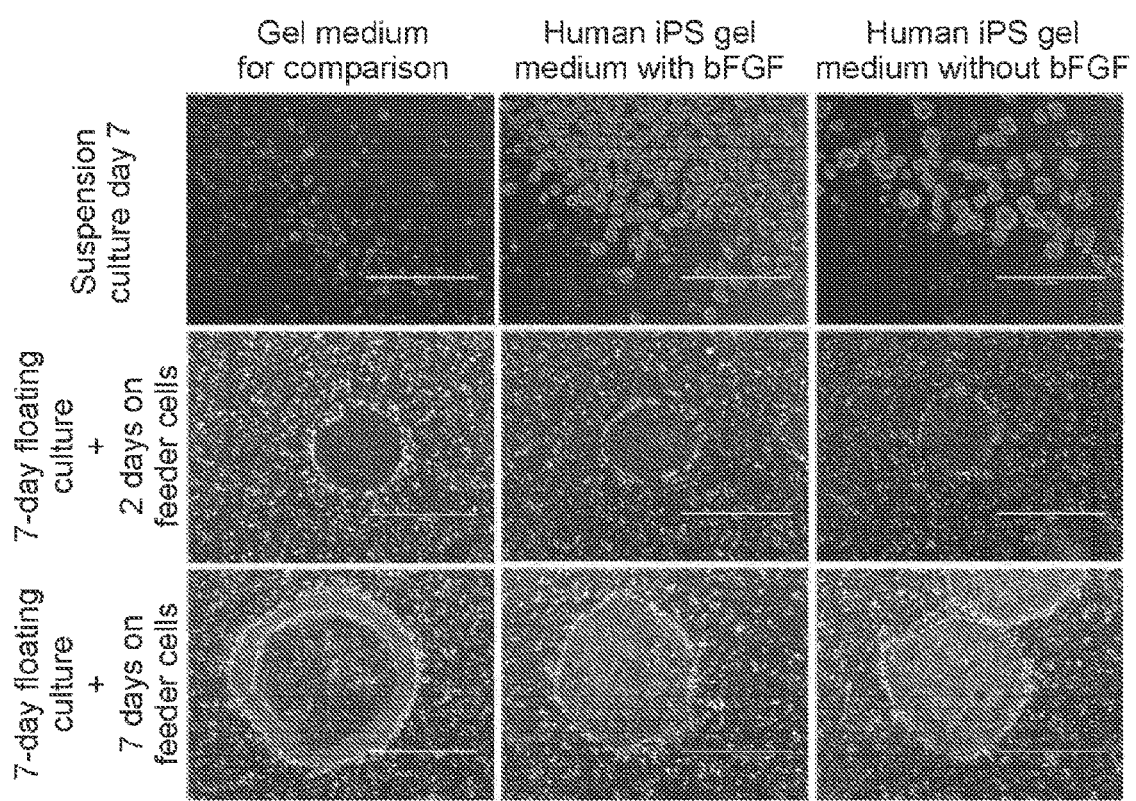

[Fig.13]
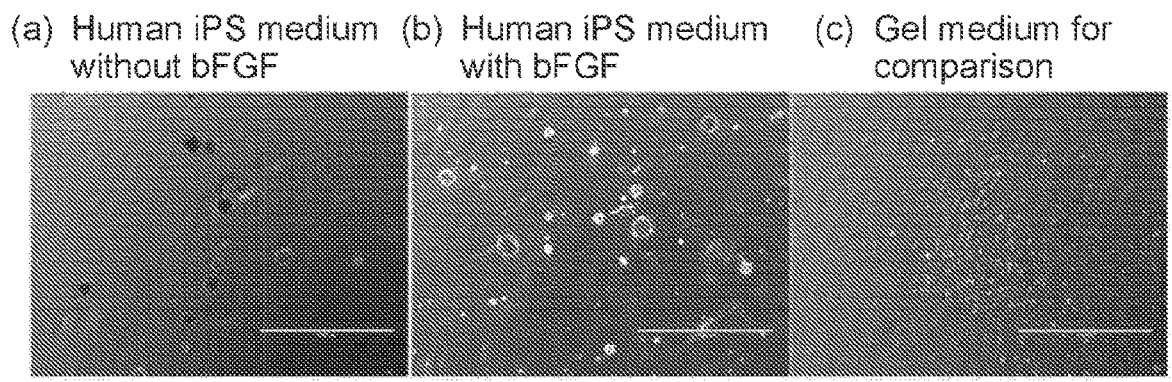

[Fig.14]
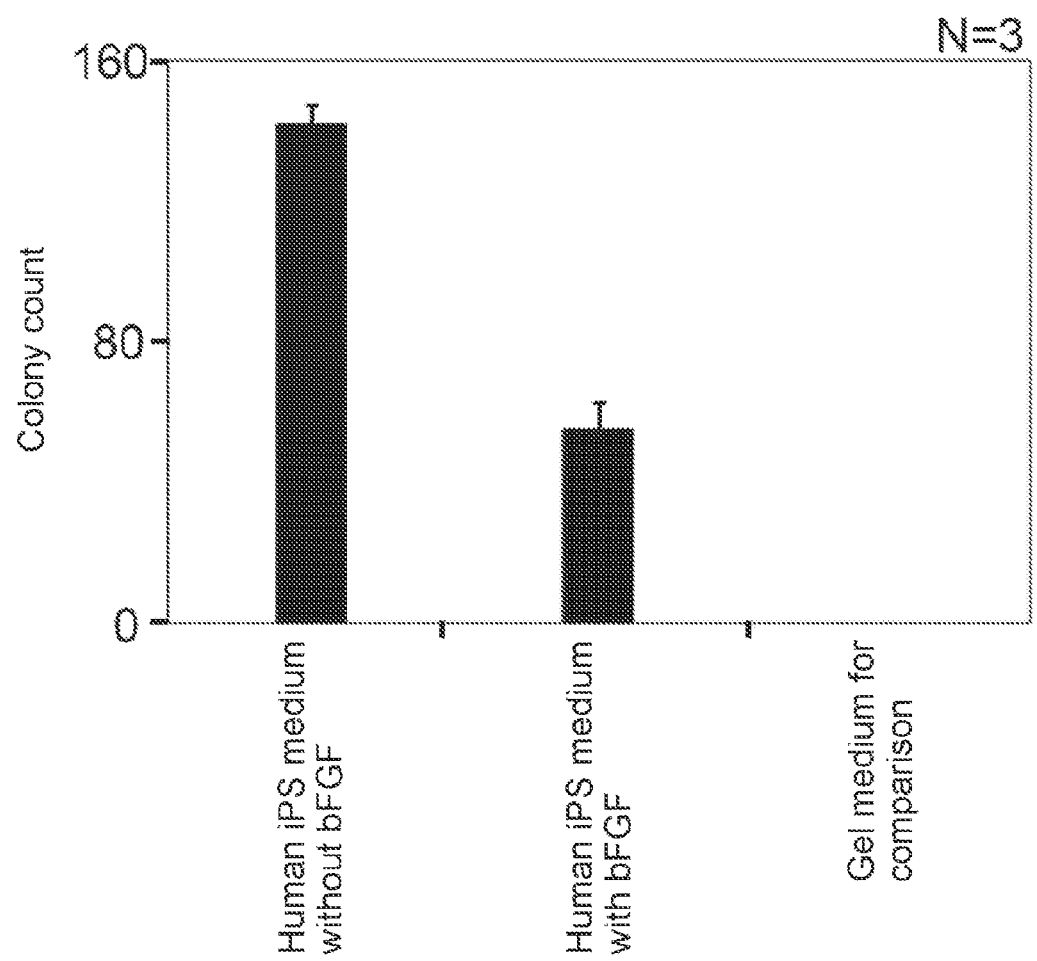

[Fig.15]
(a) NANOG-w/ bFGF
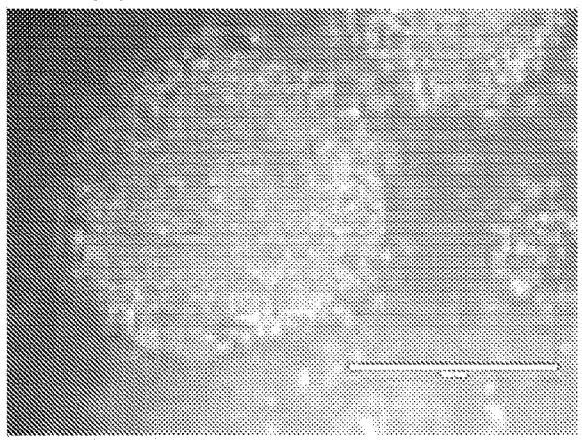
(b) OCT3/4-w/ bFGF
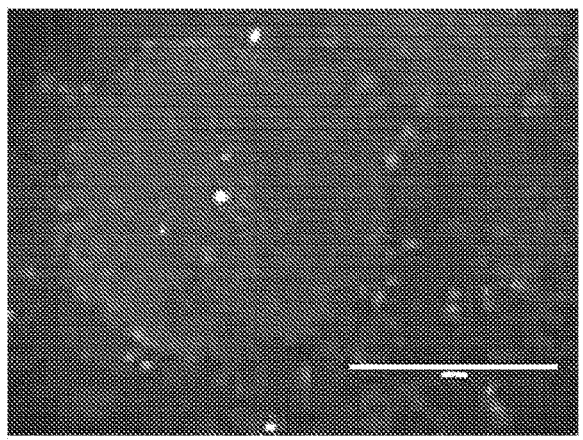
(c) NANOG-w/o bFGF
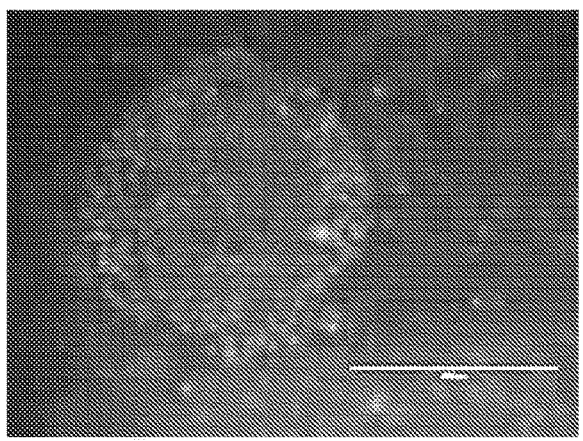
(d) OCT3/4-w/o bFGF
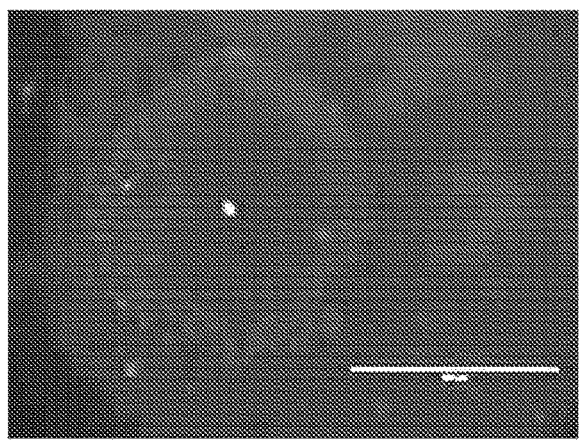

[Fig. 16]
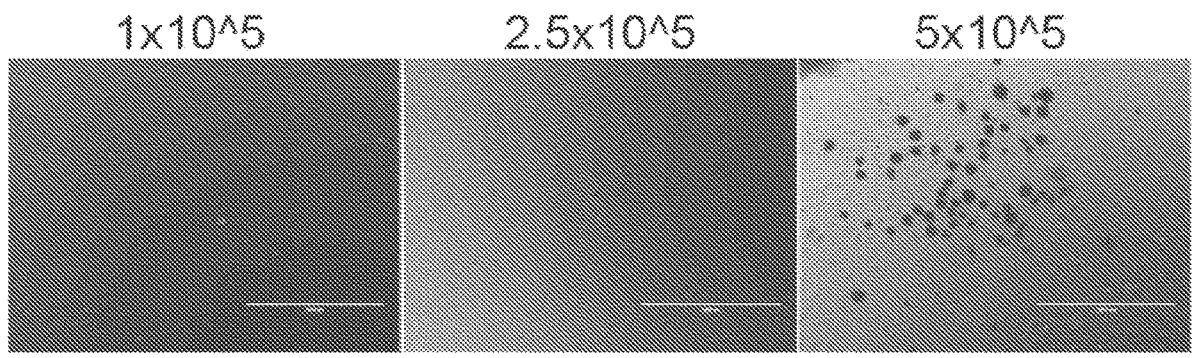

[Fig. 17]
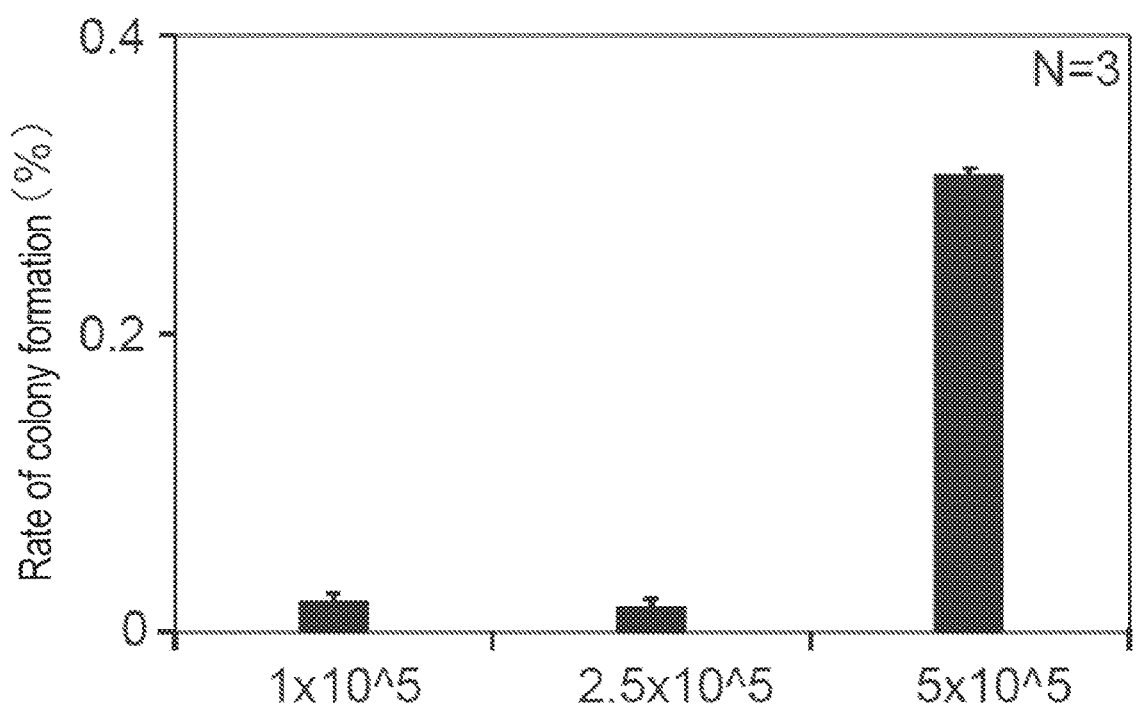

[Fig. 18]
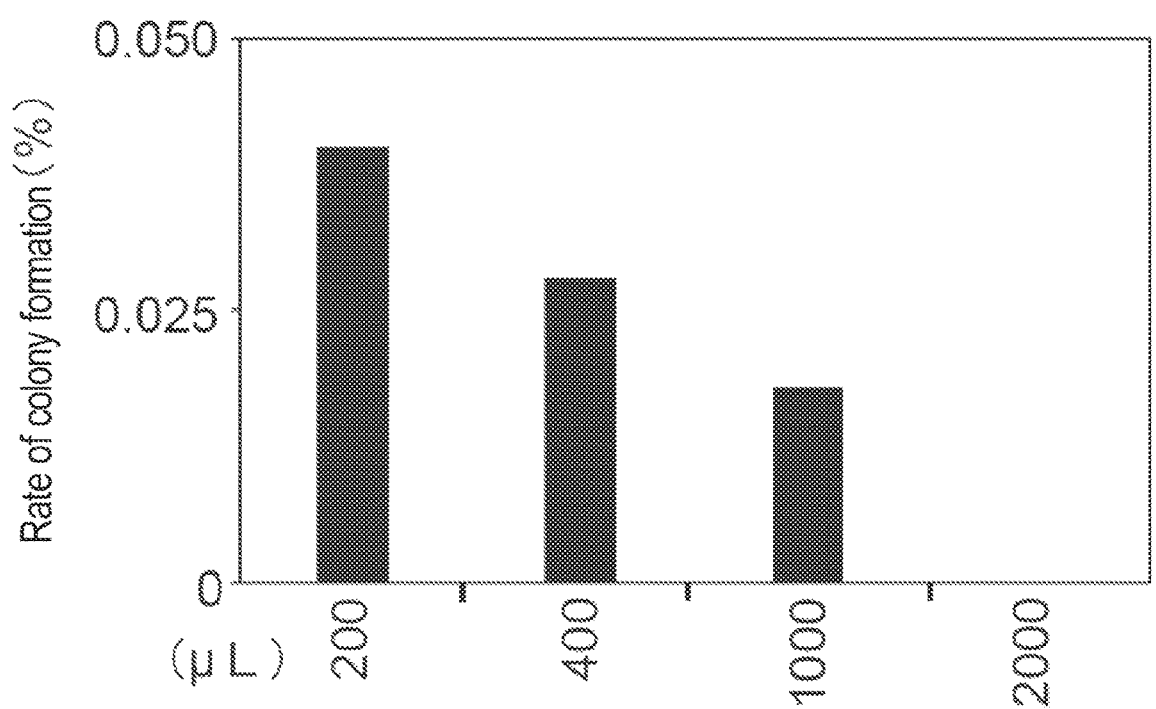

[Fig. 19]
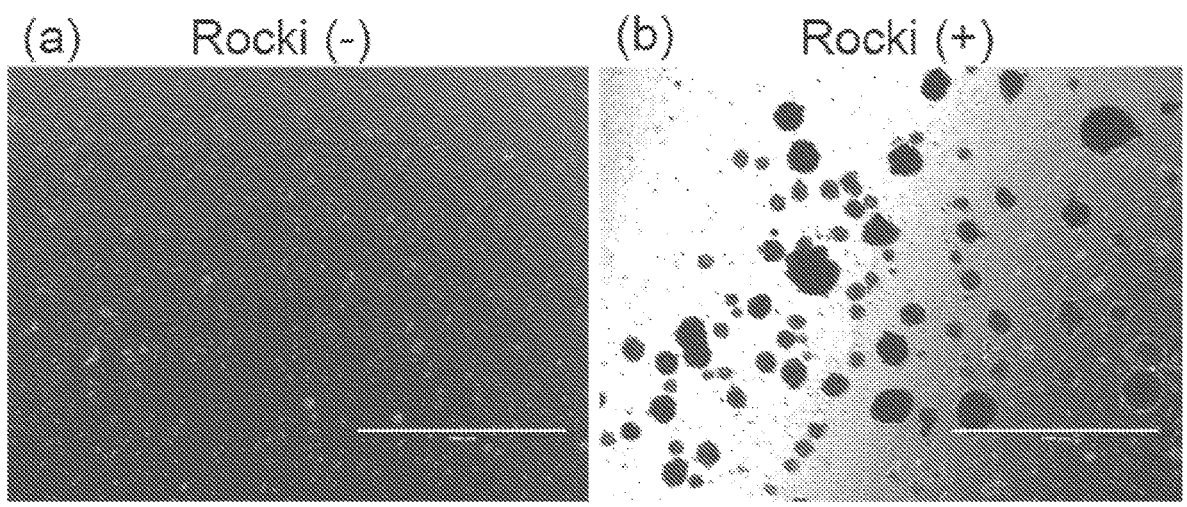

[Fig. 20]
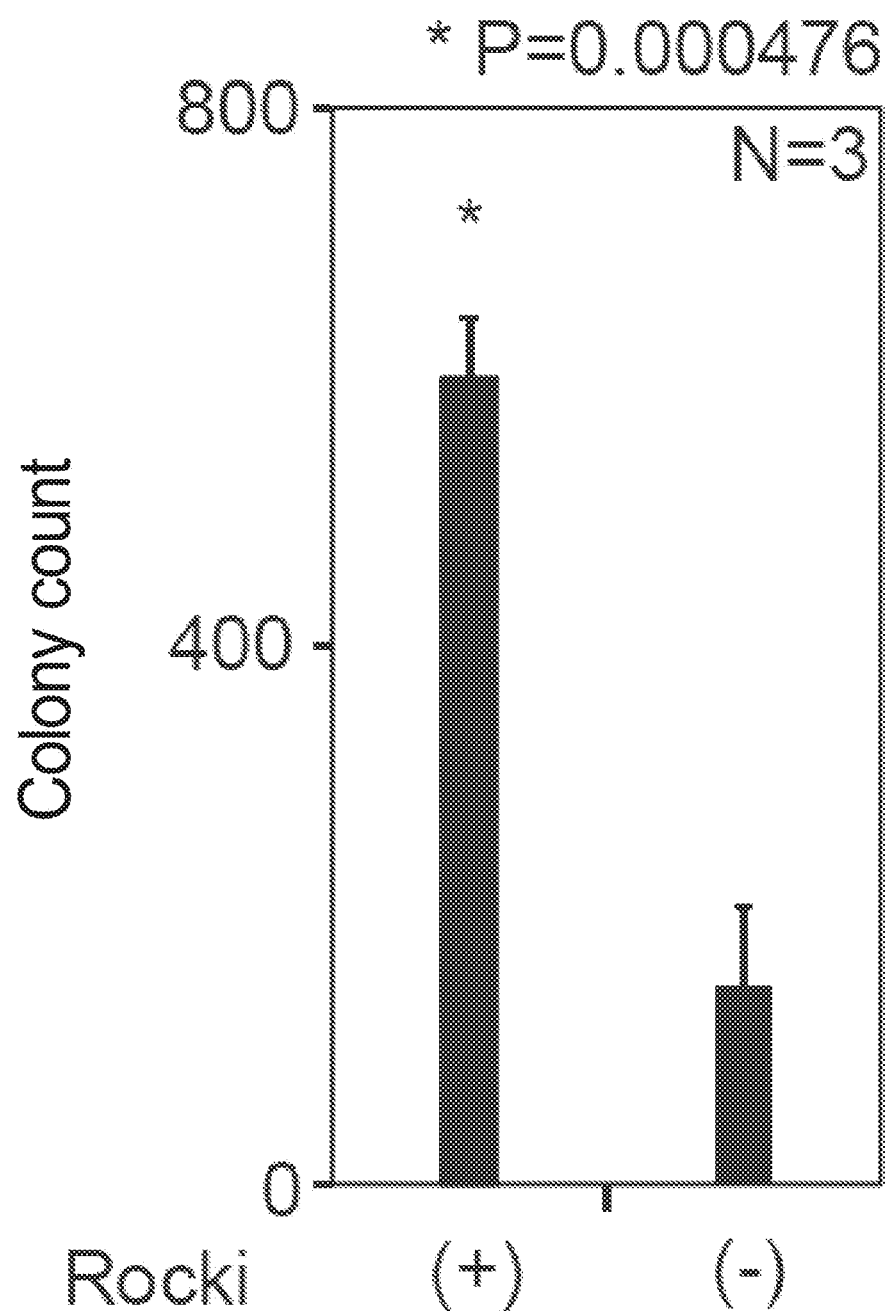

[Fig. 21]
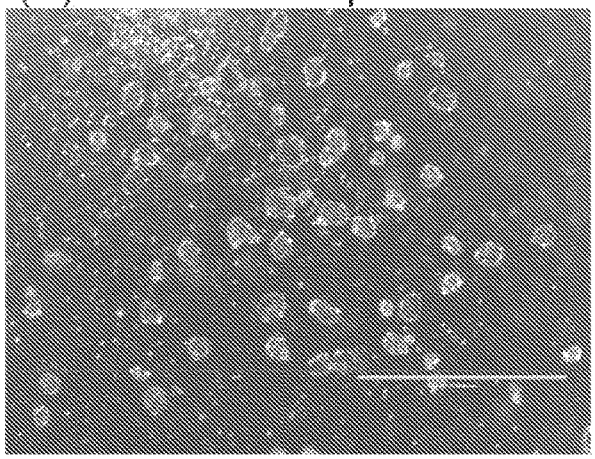
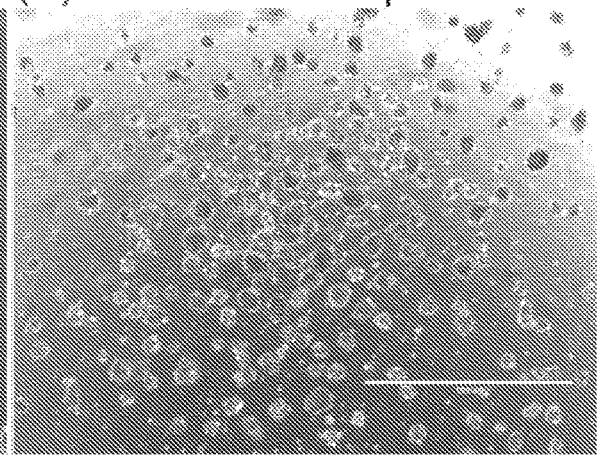

[Fig. 22]
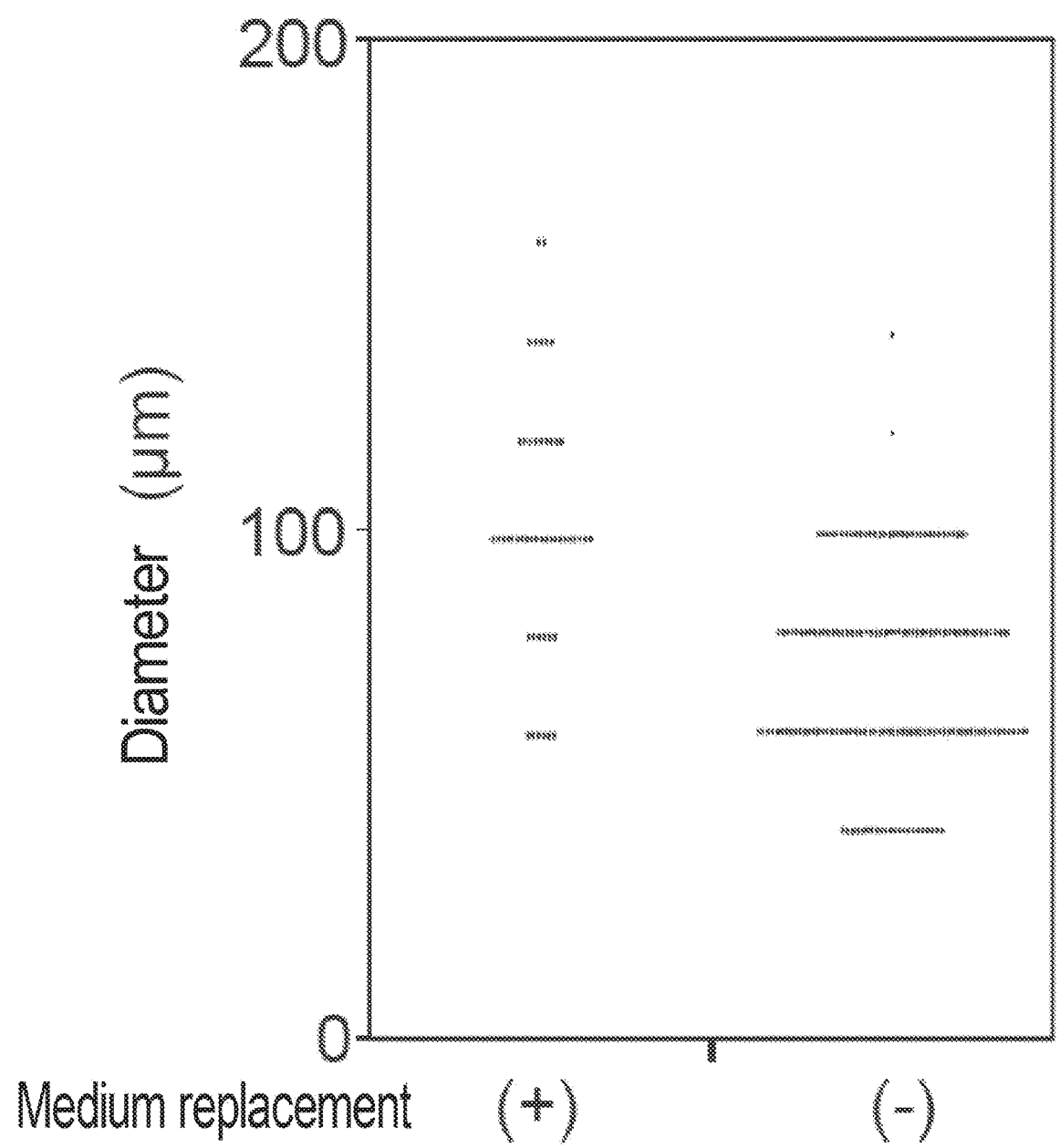

[Fig. 23]
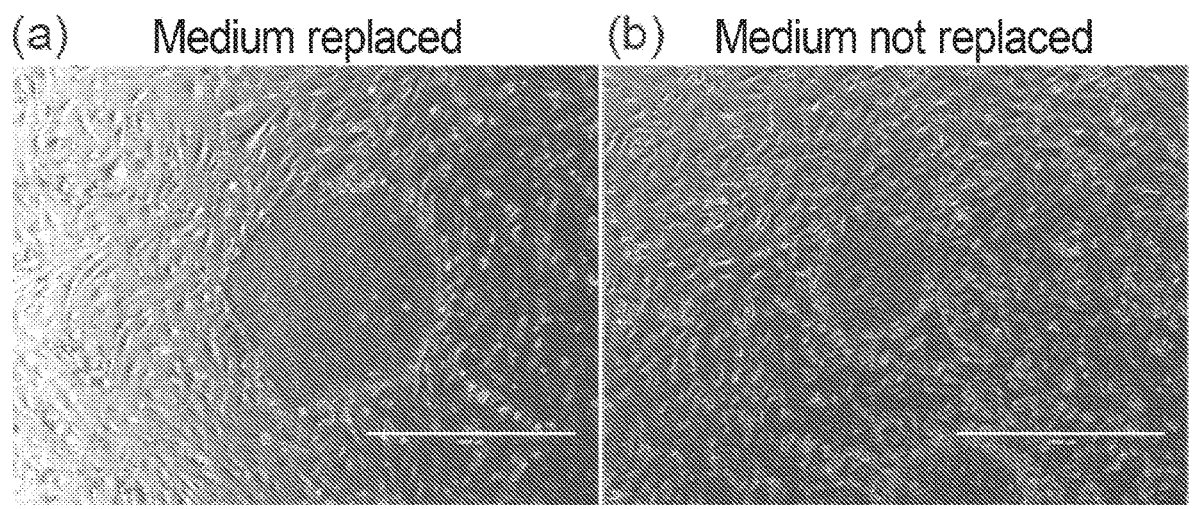

[Fig.24]
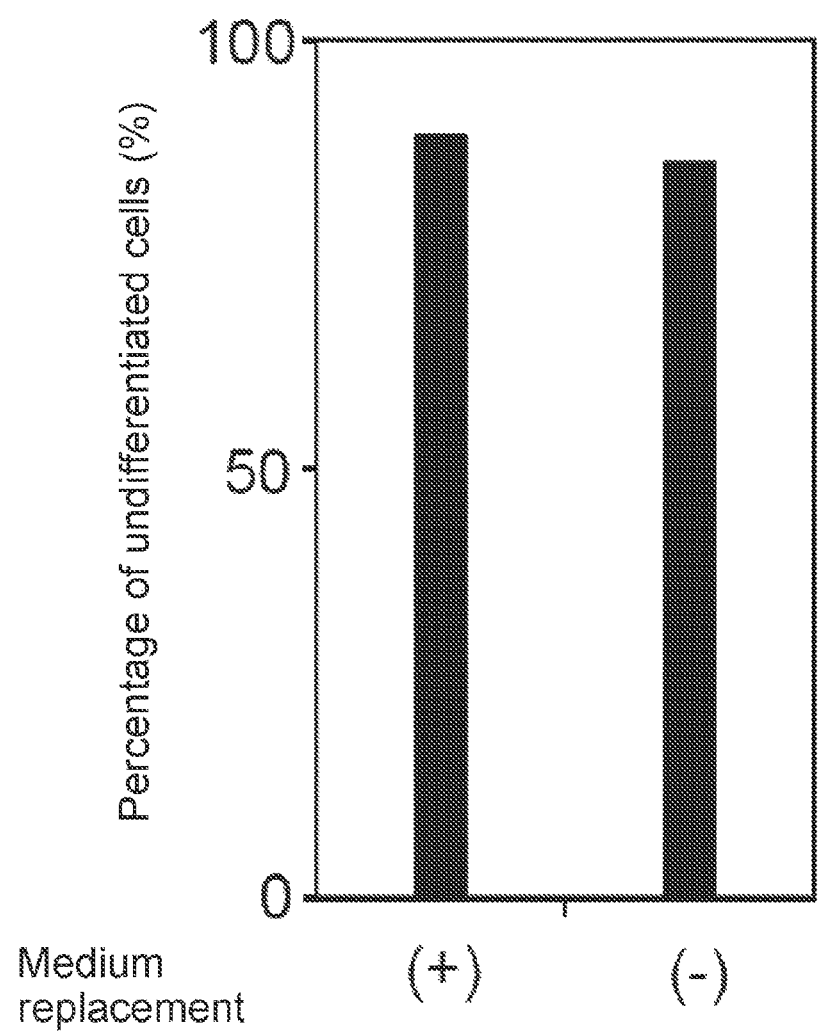

[Fig.25]
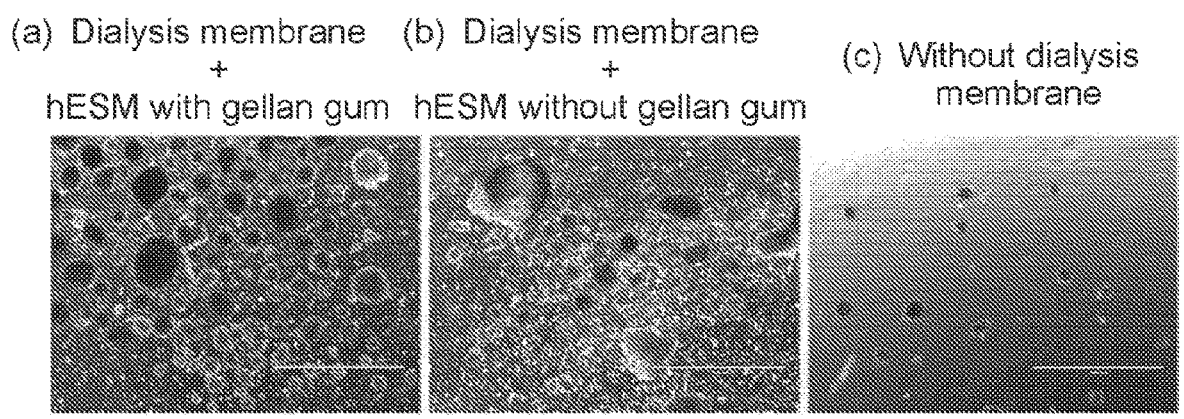

[Fig.26]
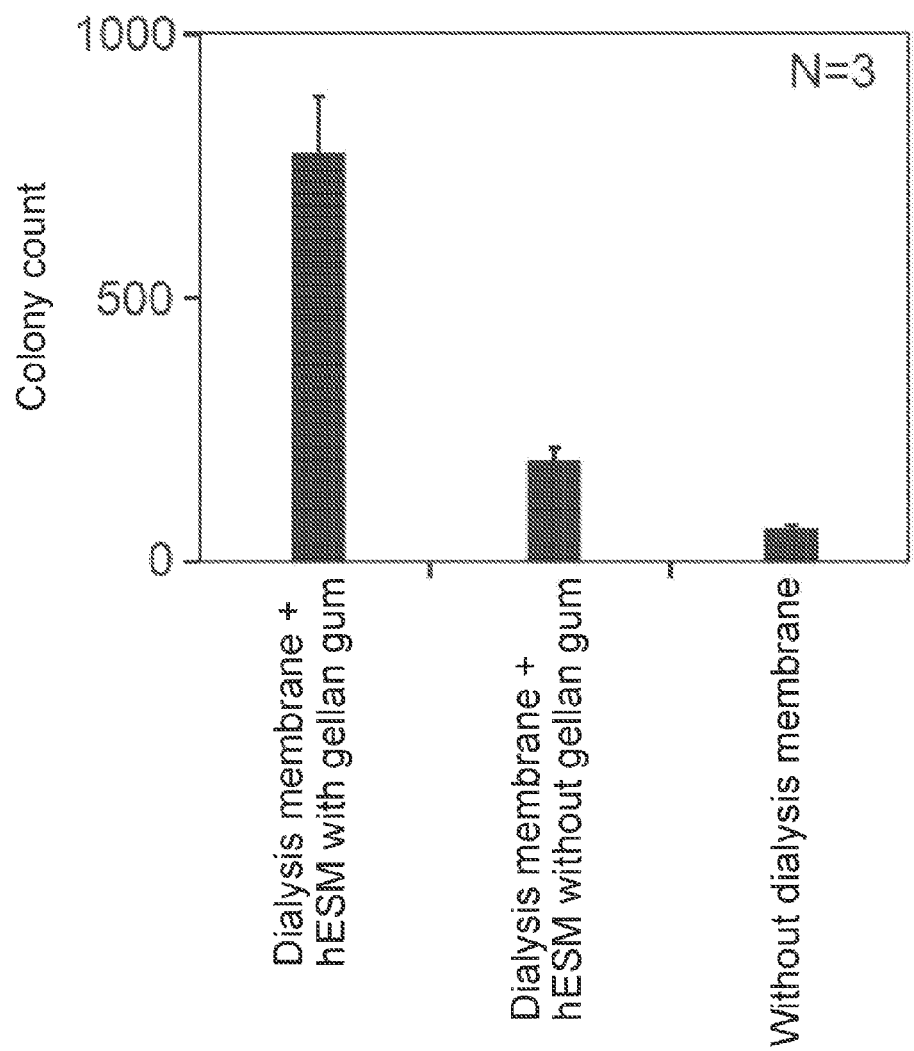

[Fig.27]
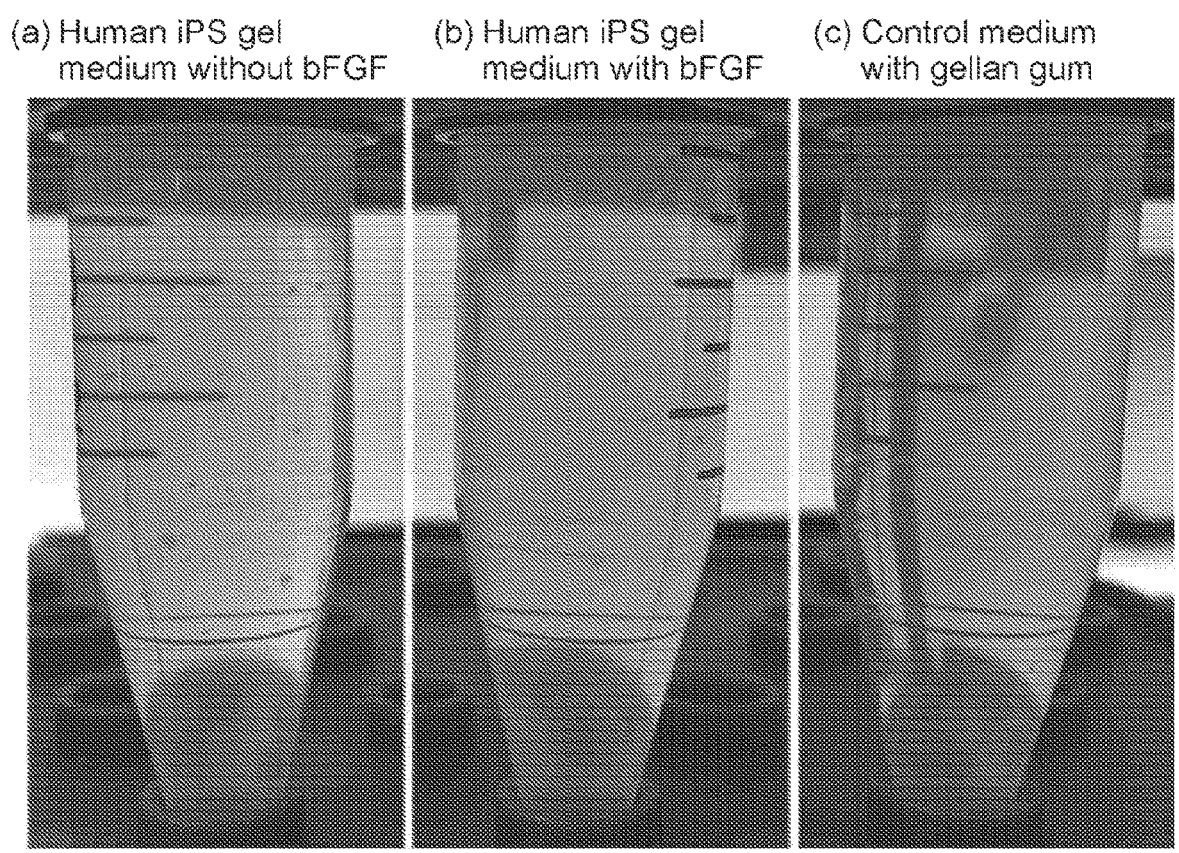

[Fig.28]
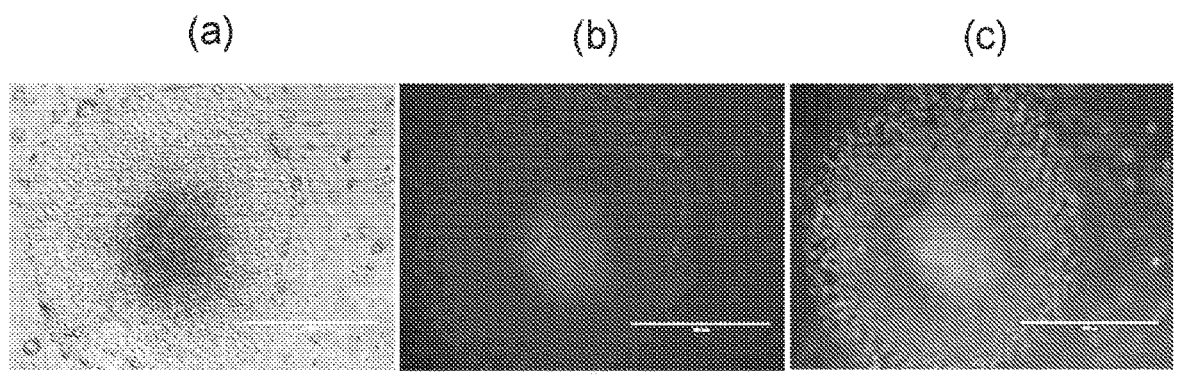

[Fig.29]
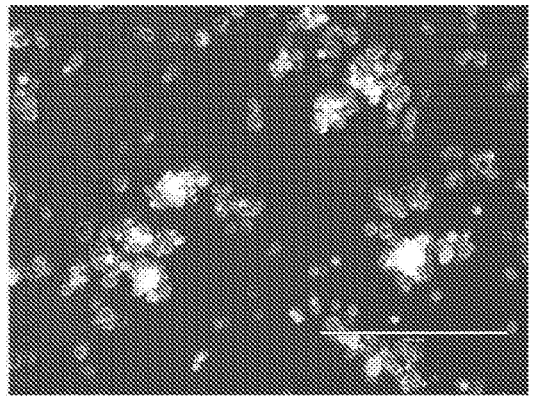 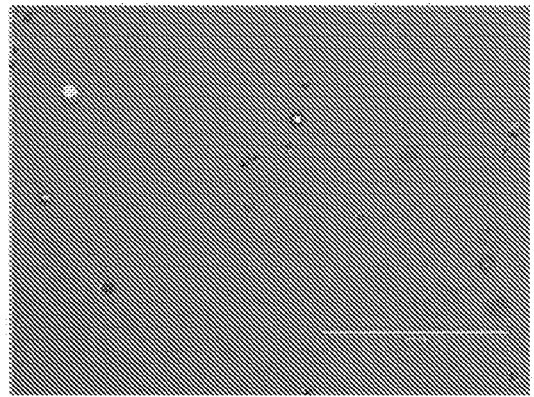
(a) Medium without gellan gum  (b) Medium with gellan gum

[Fig. 30]
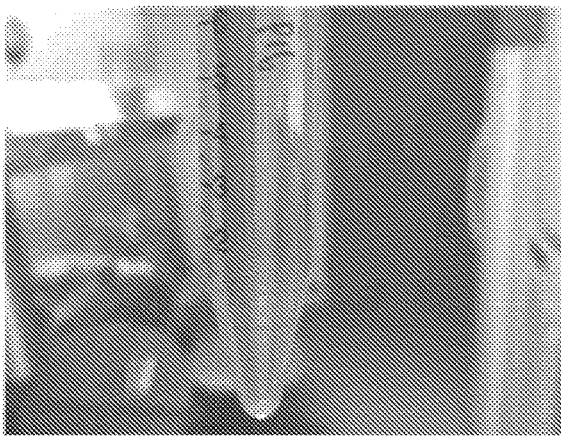 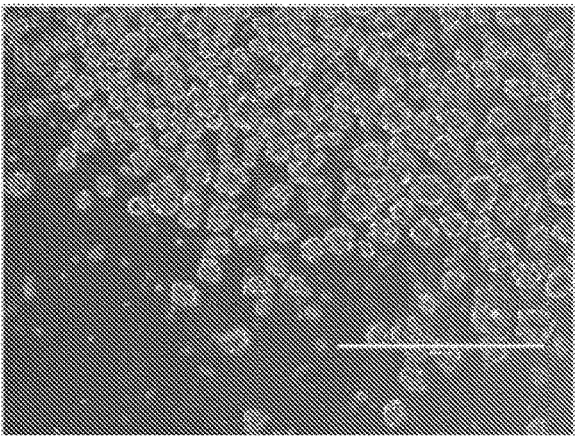
(a) GG(-) in tube   (b) GG(+) in tube
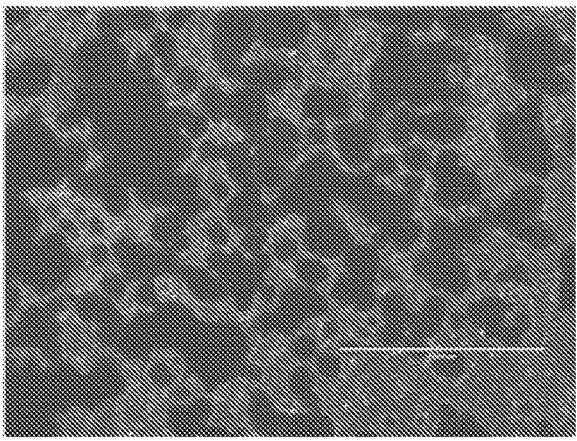 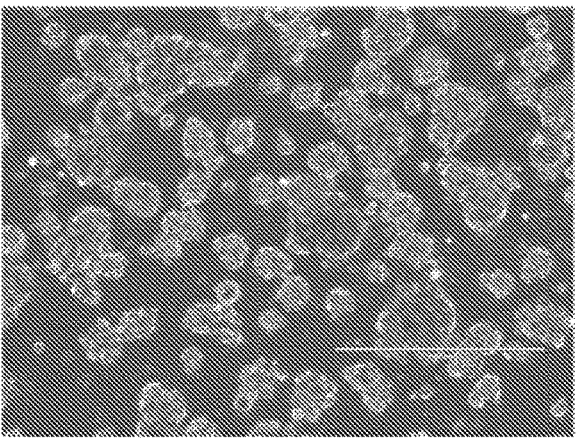
(c) GG(-) in dish   (d) GG(+) in dish

[Fig. 31]
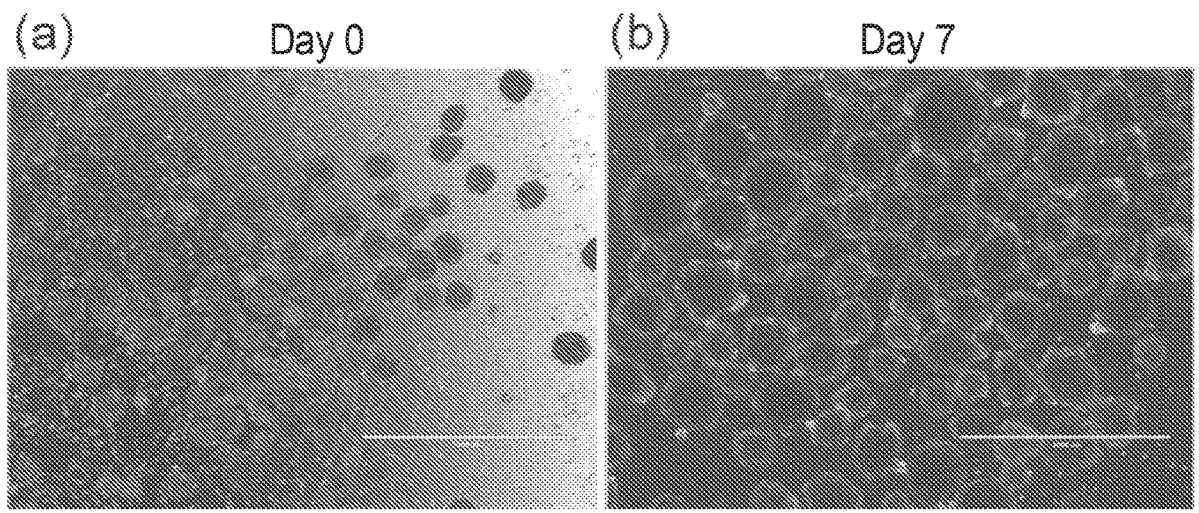

[Fig. 32]
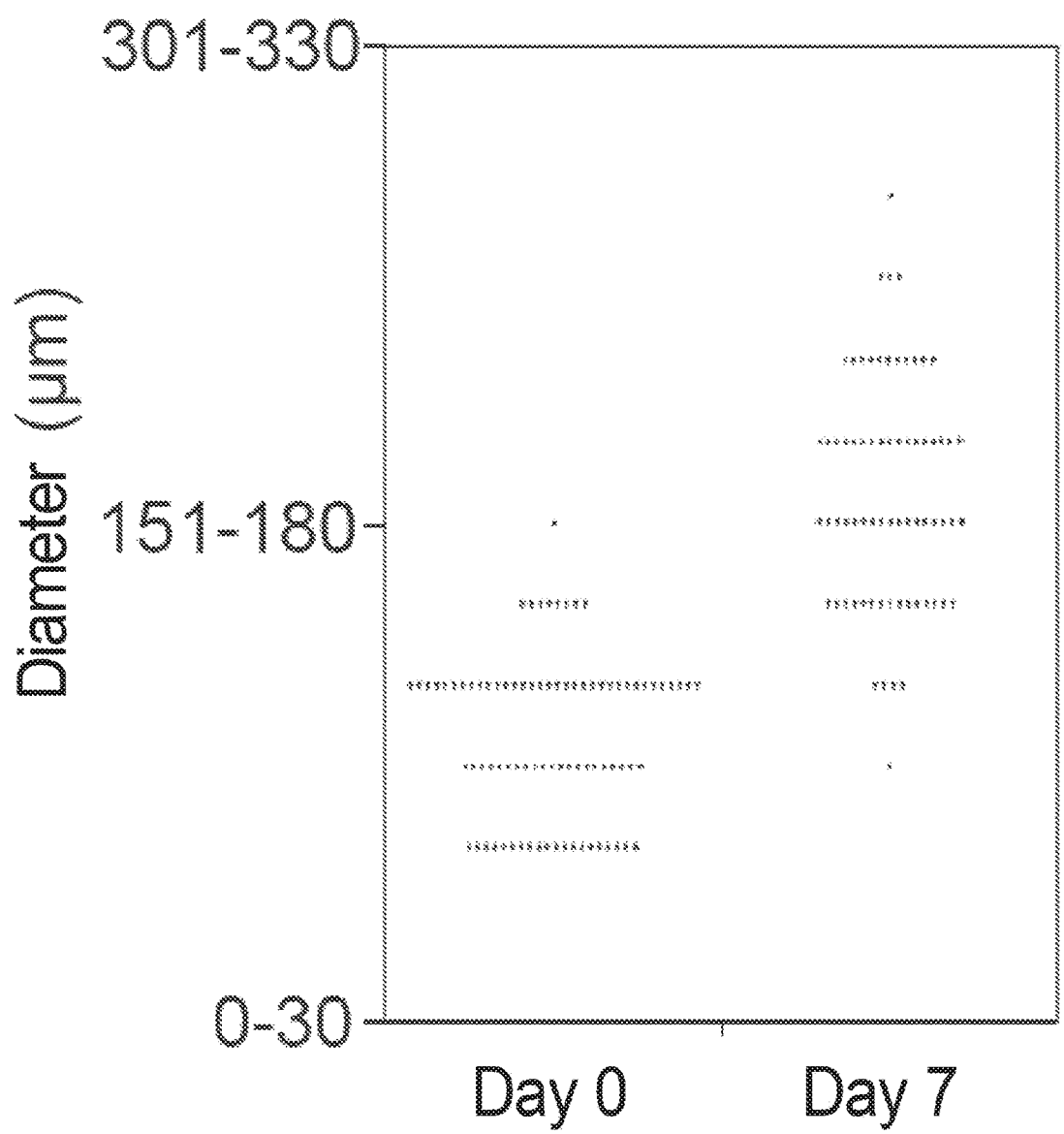

[Fig. 33]
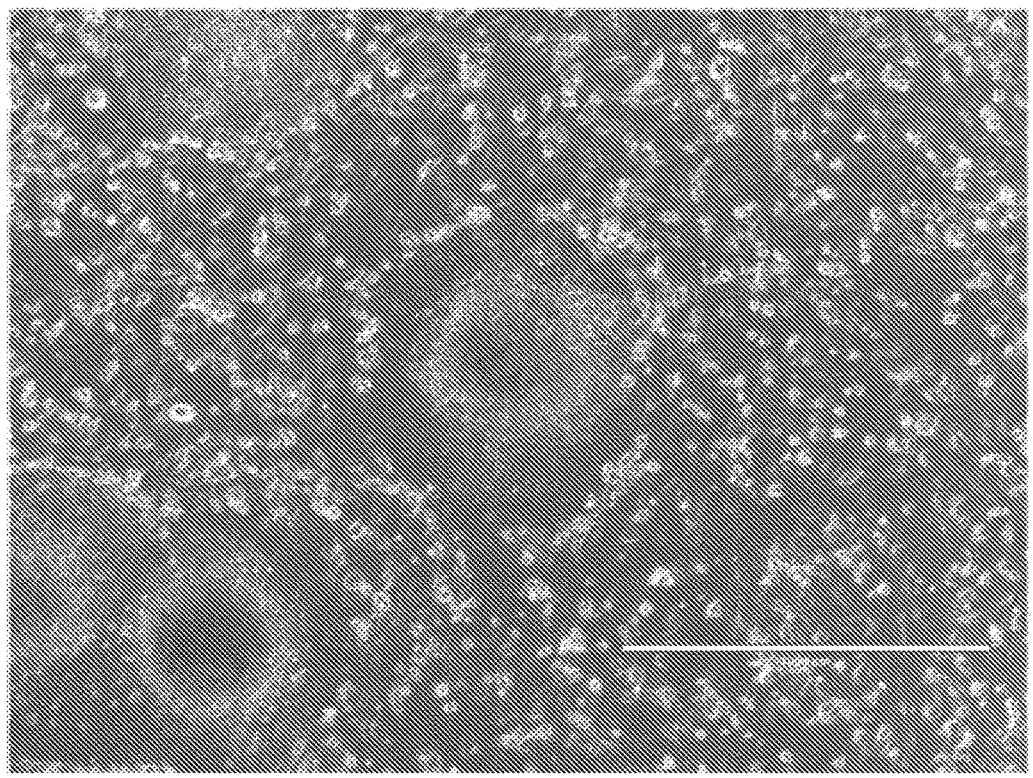
Colonies 3 days after reseeding onto feeder cells

[Fig. 34]
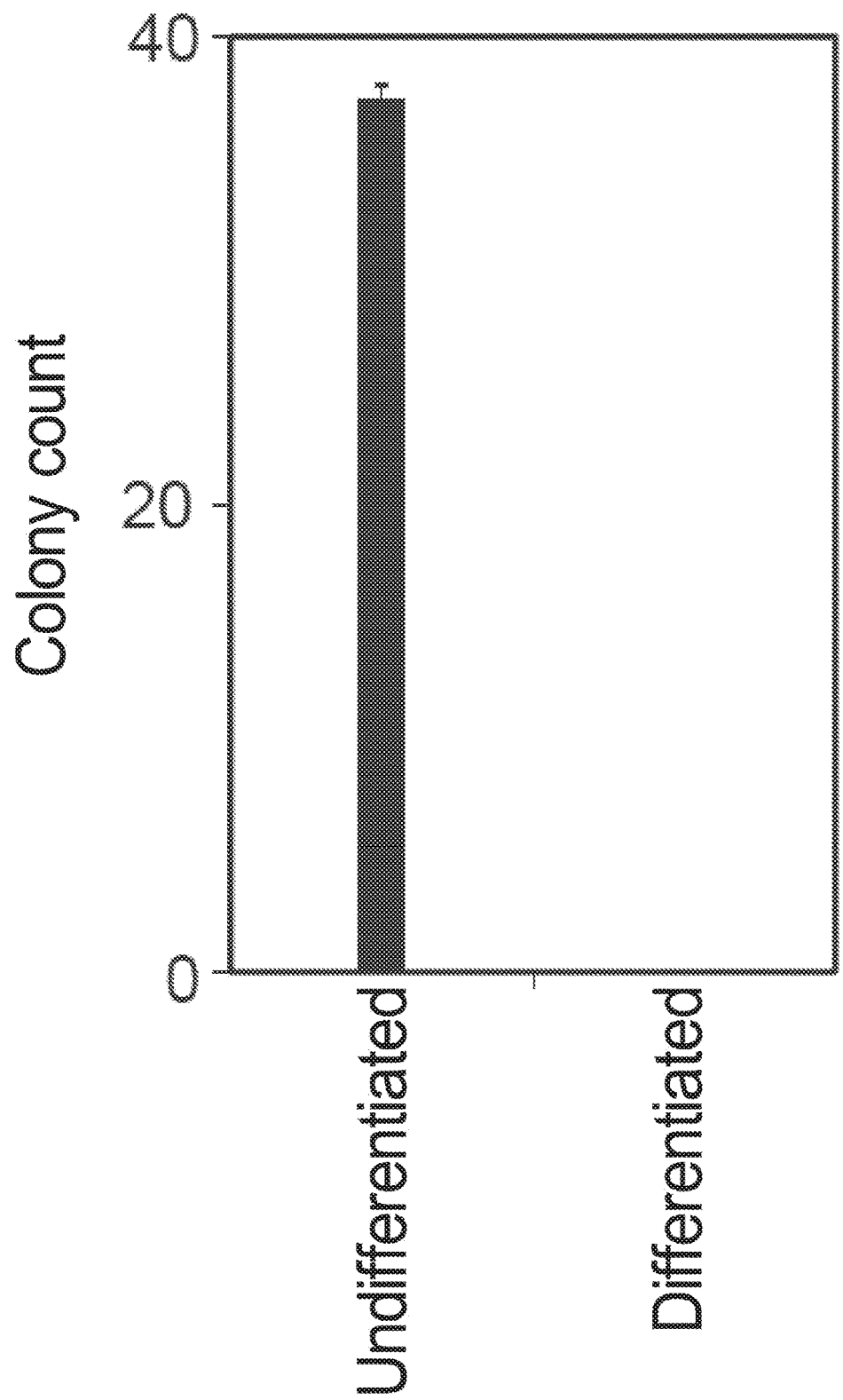

[Fig. 35]
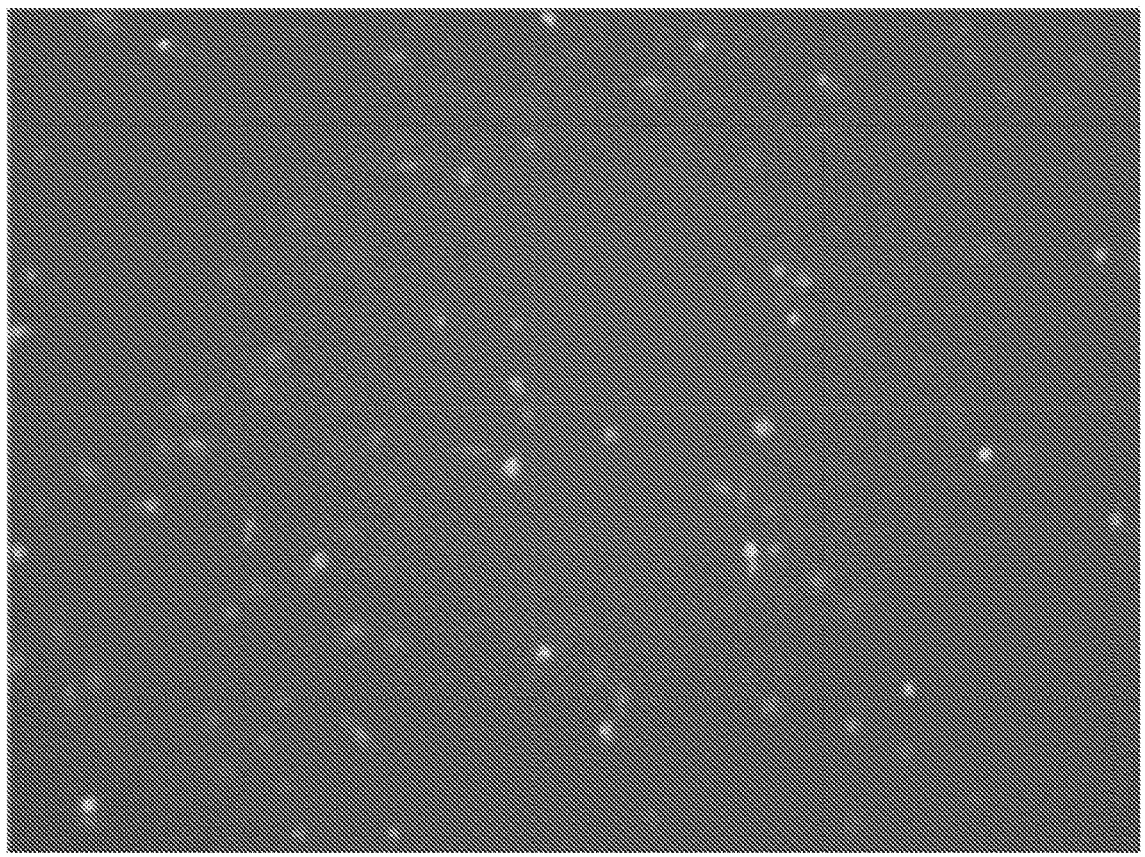

[Fig. 36]
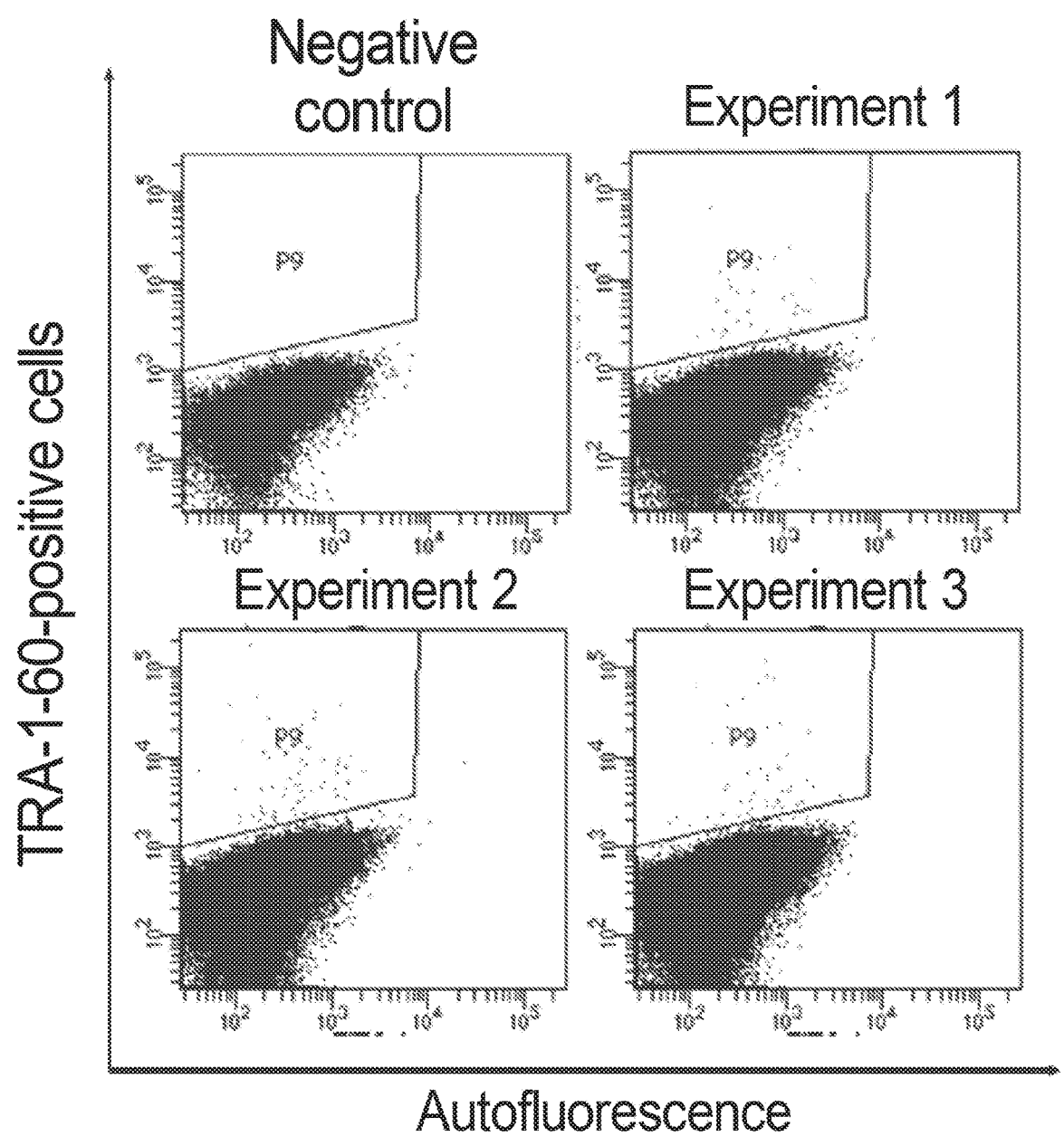

[Fig. 37]
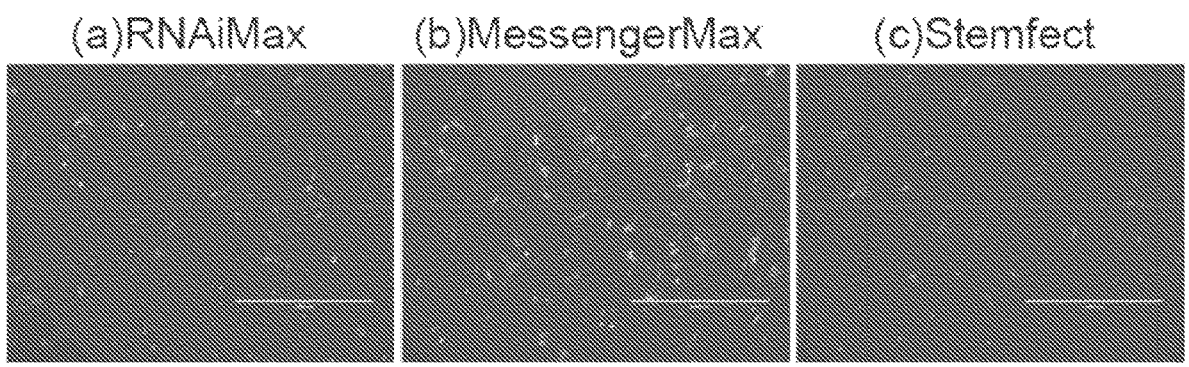

[Fig. 38]
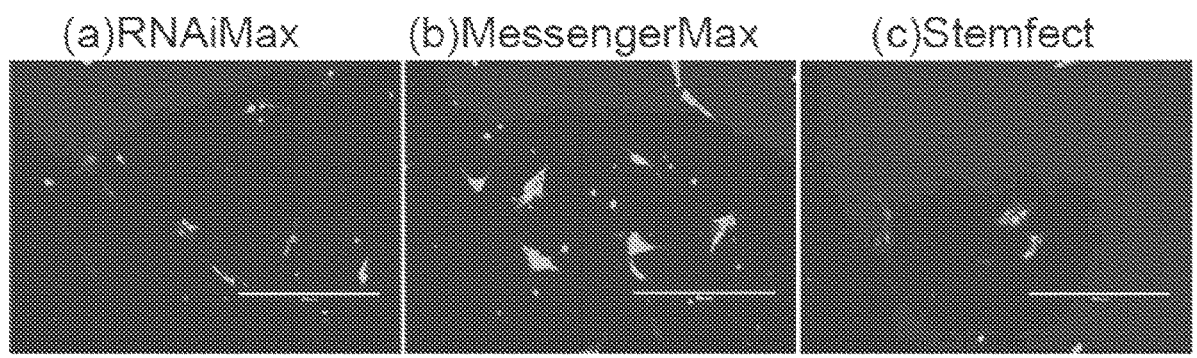

[Fig. 39]
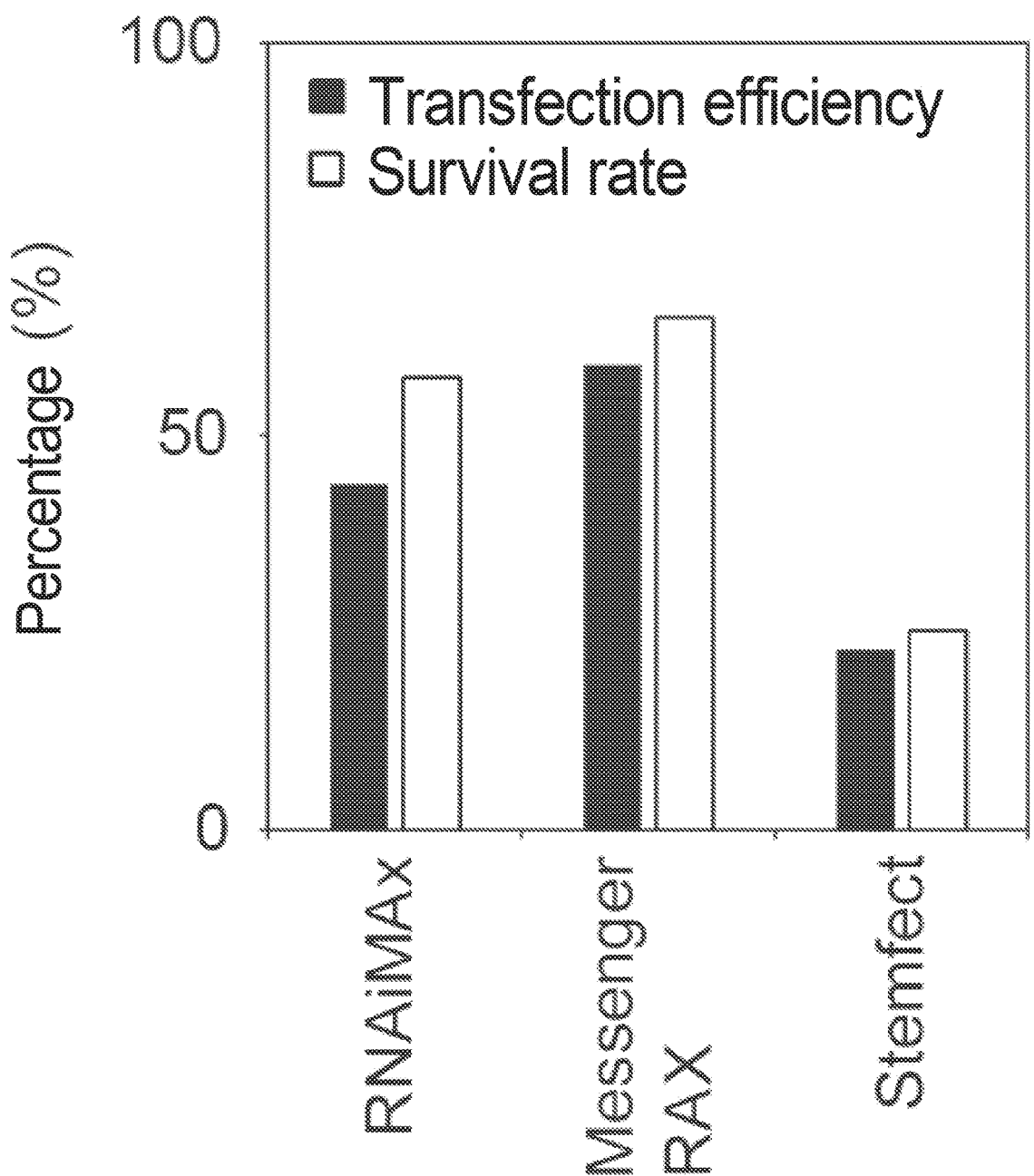

[Fig. 40]
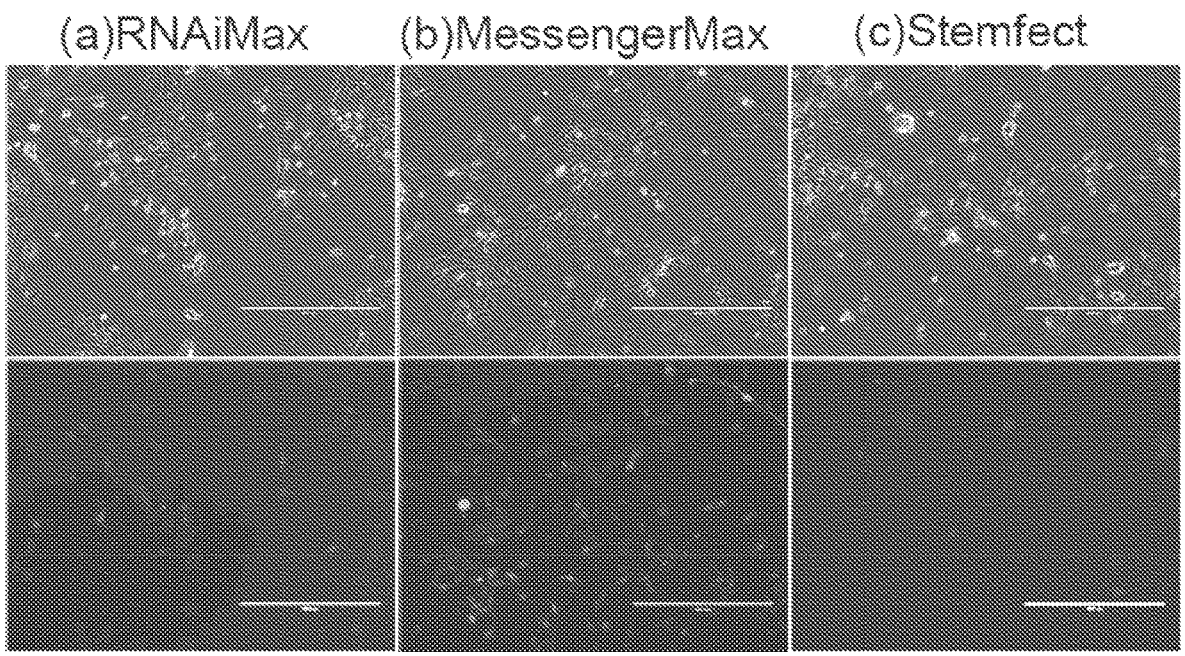

[Fig.41]
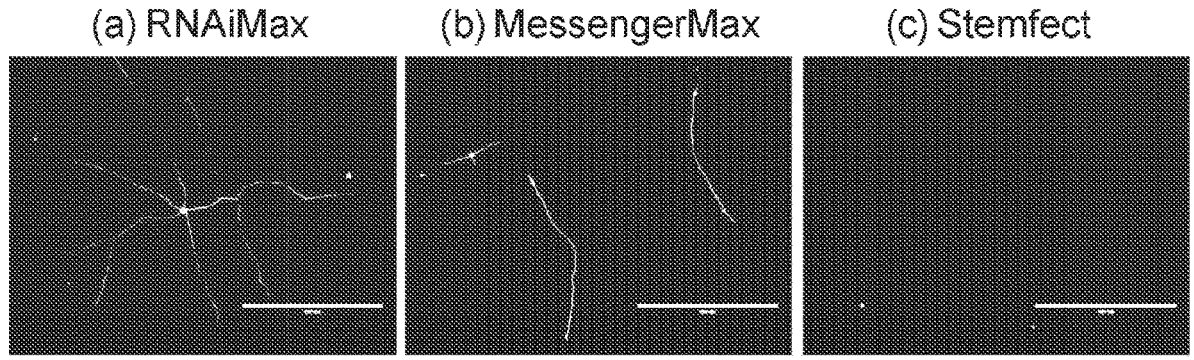

[Fig. 42]
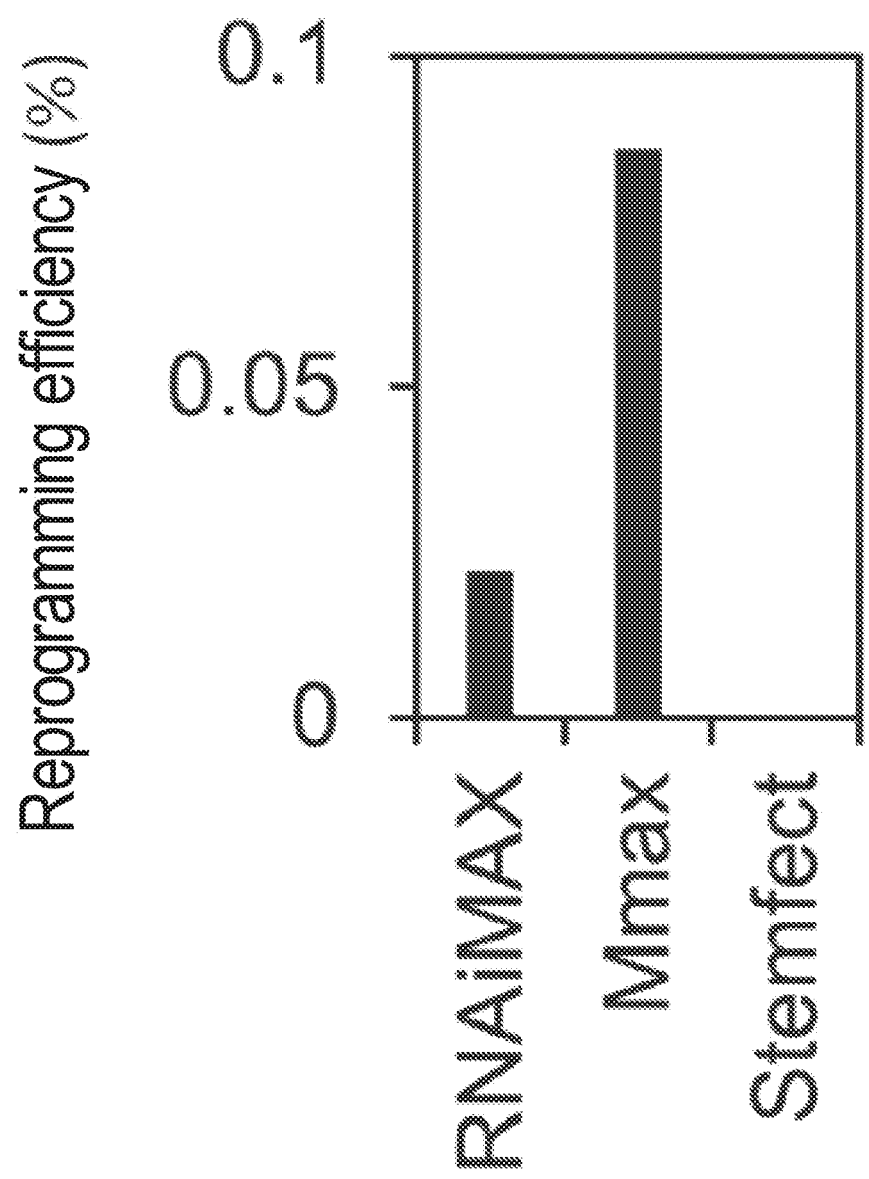

[Fig.43]
Map2
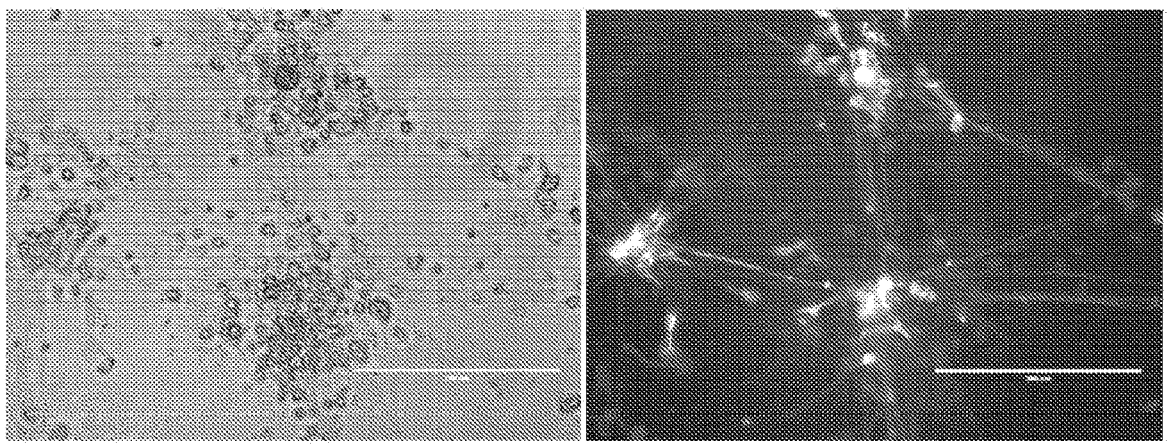
VGlut                    Map2 + VGlut
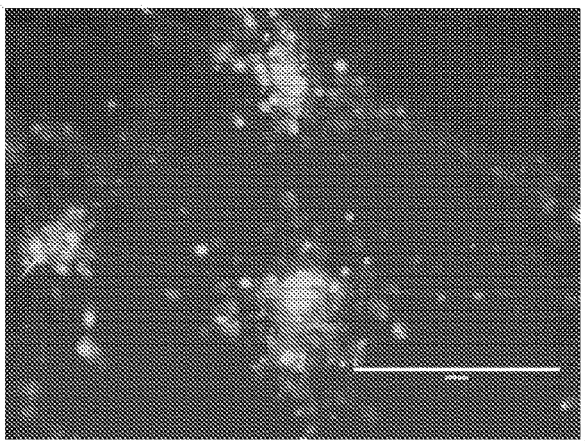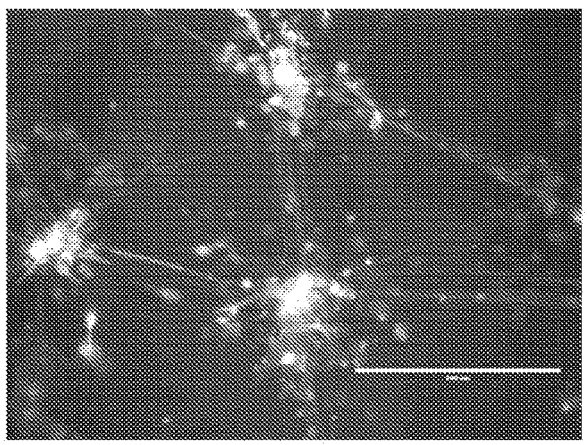

[Fig.44]
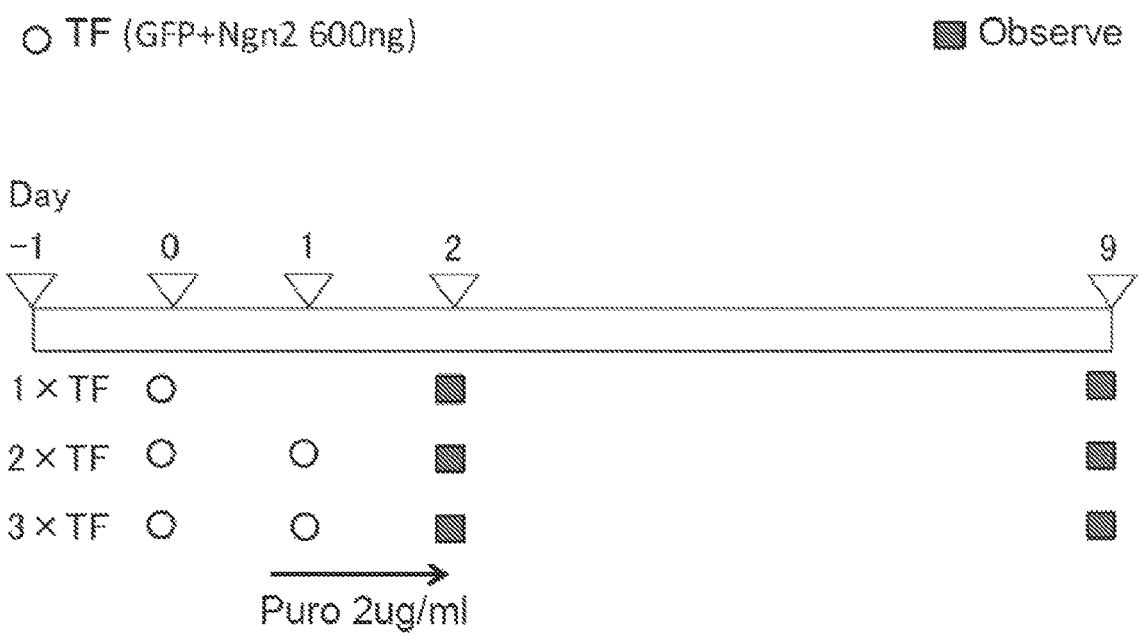

[Fig.45]
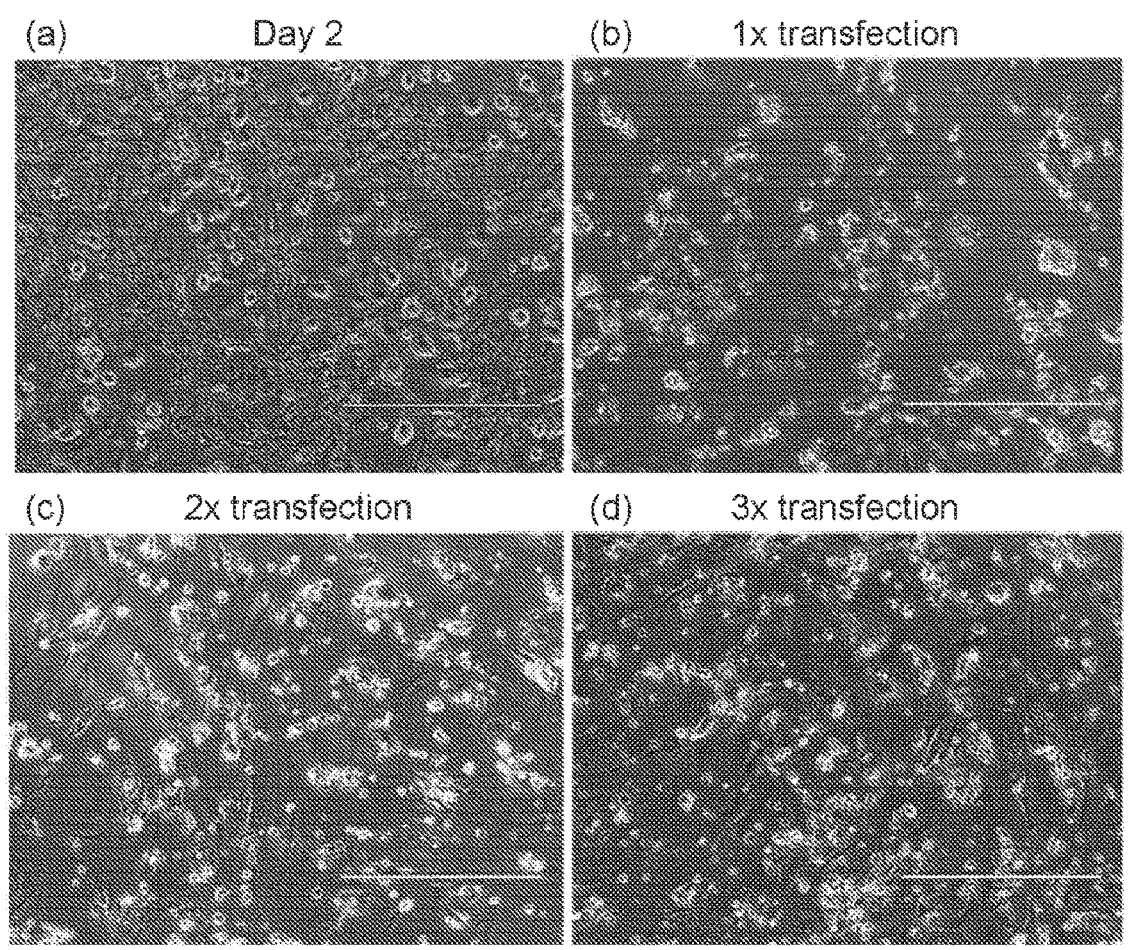

[Fig.46]
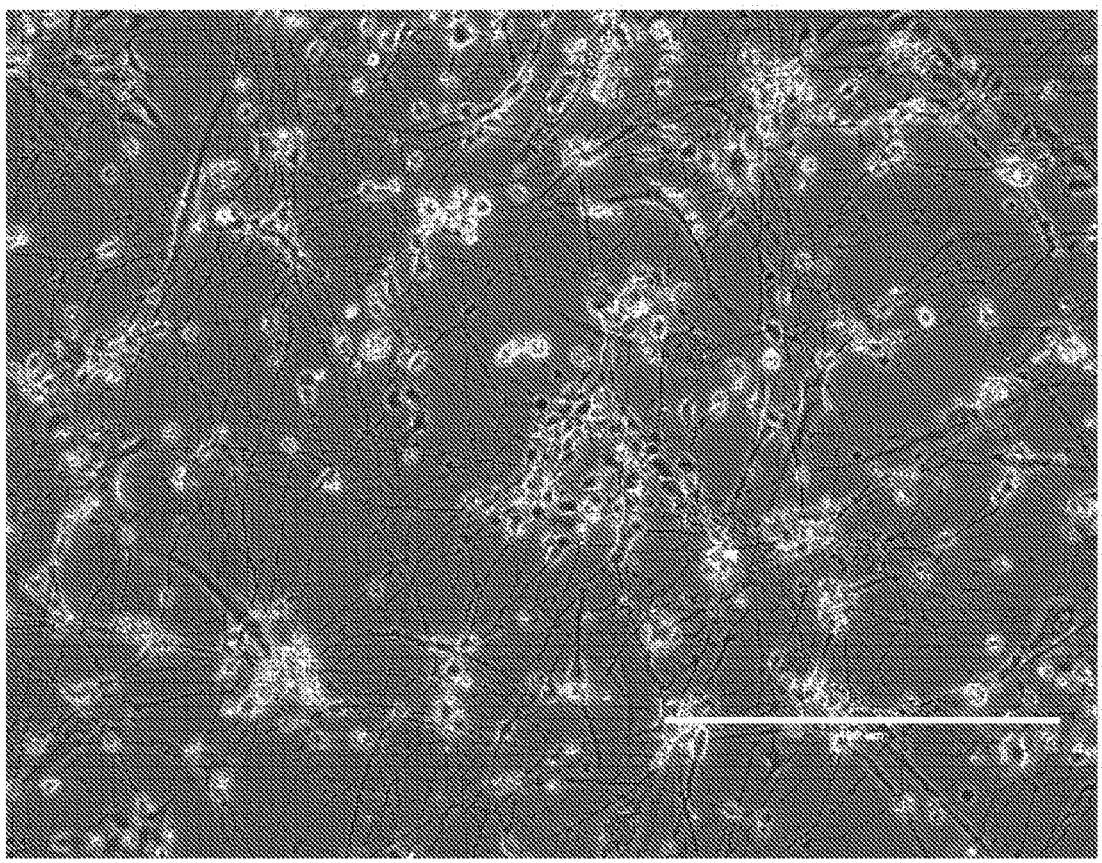
Day 7

PLURIPOTENT STEM CELL MANUFACTURING SYSTEM AND METHOD FOR PRODUCING INDUCED PLURIPOTENT STEM CELLS

TECHNICAL FIELD

The present invention relates to a cell technology and relates to a pluripotent stem cell manufacturing system, a method for inducing stem cells, a floating culture method for stem cells, a floating culture vessel for stem cells, a method for producing induced pluripotent stem cells, and a method for producing particular somatic cells from animal cells.

BACKGROUND ART

Embryonic stem cells (ES cells) are stem cells established from human or mouse early embryos. ES cells exhibit pluripotency that permits their differentiation into every cell in the organisms from which they were derived. Human ES cells are currently utilized in cell transplantation therapy to treat many diseases including: Parkinson's disease, juvenile diabetes, and leukemia. However, there are drawbacks associated with transplantation of ES cells. Notably, transplantation of ES cells can trigger immune rejection in a manner similar to the rejection which occurs subsequent to an unsuccessful organ transplantation. Moreover, the use of ES cells established by destroying human embryos has generated a large amount of ethically-based criticism and a high degree of opposition.

With these circumstances in the background, Shinya Yamanaka, a professor at Kyoto University, successfully established induced pluripotent stem cells (iPS cells) via the transfer of four genes: Oct3/4, Klf4, c-Myc, and Sox2, into somatic cells. For this, he was awarded the 2012 Nobel Prize in Physiology or Medicine (see e.g., Patent Literature 1). iPS cells are the ideal type of pluripotent cells because they escape both immune rejection and the ethical problems. Thus, it is expected that iPS cells will be used in cell transplantation therapy.

(Background Art of Method for Inducing Stem Cells, Floating Culture Method for Stem Cells, and Floating Culture Vessel for Stem Cells)

Induced pluripotent stem (iPS) cells have two characteristic potentials. The first is a potential for generating all somatic cells in the body. The second is the ability to proliferate semipermanently. Because iPS cells exhibit these two potentials, they can be used in transplantation therapy without rejection by producing iPS cells from an individual's own somatic cells and converting these cells to the somatic cells of interest. Therefore, iPS cells hold great promise in the field of regenerative medicine.

(Background Art of Method for Producing Induced Pluripotent Stem Cells)

Induced pluripotent stem (iPS) cells have two characteristic potentials. The first is a potential for generating all somatic cells in the body. The second is the ability to proliferate semipermanently. Because iPS cells exhibit these two potentials, they can be used in transplantation therapy without rejection. This can be accomplished by generating iPS cells from an individual's own somatic cells and converting these cells to the somatic cells of interest. Therefore, iPS cells hold great promise in the field of regenerative medicine.

Several methods for producing iPS cells have been established to date. Typical examples of methods for producing iPS cells include methods using retroviruses or lentiviruses, and methods using episomal vectors.

The methods using retroviruses or lentiviruses will be described. The retrovirus or the lentivirus can infect somatic cells so that genes encoding reprogramming factors are transferred into the cells. Furthermore, the retrovirus or the lentivirus can insert reprogramming factors into the genome of somatic cells to induce the stable expression of the reprogramming factors in the cells.

Methods which rely on the use of retroviruses or lentiviruses, however, are problematic. Firstly, the insertion of reprogramming factors into the genome of somatic cells damages existing genes or promoters and may therefore trigger oncogenesis of the cells. Secondly, the reprogramming factors inserted in the genome might be reactivated after conversion of the iPS cells to somatic cells. Therefore, iPS cell-derived cells for transplantation carry the risk of tumorigenesis. In fact, it has been confirmed that the transferred reprogramming factors are reactivated in the somatic cells of mouse models, and the cells become cancerous (see e.g., Non Patent Literature 1).

In addition, the iPS cells produced using retroviruses or lentiviruses may retain residual viruses. When such iPS cells are transplanted to a patient, the residual viruses might infect the patient. Therefore, these iPS cells cannot be used in transplantation. For reference, as a result of conducting gene therapy of X-linked combined immunodeficiency disease (X-SCID) in which a γc gene was transferred into hematopoietic stem cells through retrovirus vectors, the patients have been reported to develop leukemia due to the activation of the LMO2 gene by the insertion of the vectors (see e.g., Non Patent Literatures 2 and 3).

Thus, iPS cells produced using retroviruses or lentiviruses are problematic for utilization in clinical therapy.

Next, the methods using episomal vectors will be described. The methods for producing iPS cells using episomal vectors have been developed in order to overcome the problems of the gene transfer methods using retroviruses or lentiviruses (see e.g., Non Patent Literature 4). The episomal vectors are plasmids. The episomal vectors are replicated concurrently with cell division. Unlike retroviruses and lentiviruses, reprogramming factors are not inserted into the genes of somatic cells. Because of this characteristic, episomal vectors can achieve intracellular expression of reprogramming factors over a long period of time to generate iPS cells without inserting genes into the deoxyribonucleic acid (DNA) of the targeted somatic cells.

Methods which exploit the use of episomal vectors, however, are also problematic. Firstly, gene transfer into cells requires electroporation, which largely damages the cells; a high percentage of cells are damaged during even a single electroporation event. Secondly, electroporation cannot be performed repetitively. Furthermore, the gene transfer efficiency of the methods which dictate the use of episomal vectors is lower than that of retrovirus/lentivirus-based methods.

Recent research has revealed that the transfer of episomal vectors may result in fragments of the vector DNA being inserted into the genes of the target iPS cells. Therefore, even when episomal vectors are used, there is a high probability that the resulting iPS cells will contain vector fragments that have been inserted into their genome. Thus, the clinical application of such iPS cells remains controversial.

For these reasons, the iPS cells produced using episomal vectors are likewise difficult to utilize clinically.

Since both the methods using retroviruses or lentiviruses and those using episomal vectors are problematic as described above, a method for producing iPS cells using RNA has been proposed (see e.g., Non Patent Literature 6). However, there has been no report on the successful induction of iPS cells from adult human-derived somatic cells using RNA, though successful iPS cell induction has resulted from the use of fetal or newborn fibroblasts. Therefore, unless iPS cells can be produced from adult human-derived somatic cells, their clinical application is difficult.

Further, for collecting fibroblasts necessary for the production of iPS cells, a 1 cm squared piece of skin needs to be harvested. This puts a great deal of burden on the skin donor. After excision, the fibroblast cell culture line must be established by expansion culture. As these fibroblasts proliferate over the course of the expansion, there is a high likelihood that they will incur genomic damage and/or chromosomal aberrations.

(Background Art of Method for Producing Particular Somatic Cells from Animal Cells)

Induced pluripotent stem cells (iPS cells) can generate every somatic cell in the body. Therefore, iPS cells, which can be converted to various types of somatic cells or tissues, are expected to be utilized for cell transplantation therapy and drug discovery research. For example, retinal cells produced from iPS cells were used in transplantation therapy in 2014. Numerous projects are underway around the world to generate brain cells (and cells of various other organs) from iPS cells for subsequent use in transplantation therapy.

Heretofore, a wide range of methods for converting iPS cells to somatic cells has been developed. However, in order to use iPS cells for transplantation therapy, an efficient method to induce iPS cell differentiation is of significant importance. Specifically, it is necessary to develop an instrument for inducing the differentiation of iPS cells into somatic cells to improve the efficiency and accuracy of induced differentiation. This instrument should produce functional somatic cells which are amenable to transplantation therapy.

Conventional methods for inducing the differentiation of iPS and ES cells into somatic cells rely on various combinations and concentrations of growth factors, hormones, and/or small molecules to manipulate the cell's fate in an attempt to recapitulate the process of natural development. Natural development which occurs in vivo, however, is difficult to replicate in vitro and is relatively inefficient. Moreover, induced differentiation of iPS cells into human somatic cells takes longer in humans than in mice. For example, a minimum of three months is required for producing human mature neuronal cells. Furthermore, the efficiency of induced differentiation largely differs among ES/iPS cell lines, resulting in problems such as inhomogeneous properties of induced somatic cells. This phenomenon was evidenced when multiple ES clones from the same source, treated with identical chemicals, produced differing phenotypes. Some of these clones differentiated into spleen cells, while others became cardiac cells, indicating that the potentiality to differentiate differs among clones (see e.g., Non Patent Literature 6). Furthermore, when attempts were undertaken to differentiate large quantities of iPS and ES cell types into neuronal cells using a method called serum-free floating culture of embryoid body-like aggregates with quick reaggregation (SFEBq), it was found that though iPS cells and ES cells were cultured in a serum-free medium free of neural differentiating substances, some iPS and ES clones were difficult to successfully convert to neuronal cells (see e.g., Non Patent Literature 7).

Specifically, cells that were induced to differentiate from human ES/iPS cells, through methods using hormones or chemical substances, were confirmed to be analogous to fetal somatic cells at the initial stage. Furthermore, induced differentiation of ES/iPS cells into human mature somatic cells is very difficult and requires long-term culture over several months. However, for drug discovery or medical transplantation in individuals which have completed development, it is critical to produce somatic cells commensurate to the age of these individuals.

Neuronal cells include various subtypes of cells. Methods using hormones or chemical substances to induce the differentiation of ES/iPS cells into particular neuronal subtypes have failed to produce homogeneous cell populations. Therefore, drug discovery screening specific to a particular neuronal cell subtype cannot be achieved. Consequently, the effectiveness of drug discovery screening is low. Also, with regards to medical transplantation, distinct neuronal cell subtypes necessary for disease treatment cannot be enriched for transplantation.

By contrast, a method for producing somatic cells of interest, by directly transferring into ES/iPS cells, a gene containing the information to generate the properties of the particular somatic cells, using a virus, has been proposed. This method makes it possible to specifically produce mature neuronal cells in a much shorter time (two weeks) than the aforementioned methods which rely on the use of hormones or chemical substances. For example, a homogeneous population of excitatory neurons can be obtained by transfecting specific genes into ES/iPS cells. Therefore, it is considered that drug discovery screening specific for a particular neuronal cell subtype can be achieved. Likewise, for medical transplantation, specific neuronal cell subtypes can be enriched and transplanted to treat disease.

However, the method for inducing the differentiation of stem cells into somatic cells, using a virus for the expression of a particular gene, inserts that gene into the genome of ES/iPS cells and damages endogenous genes. As a result, disadvantageously, drug discovery screening is not necessarily accurate, and transplantation imparts the risk of tumorigenesis (see e.g., Non Patent Literatures 8 and 9).

CITATION LIST

Patent Literature

[Patent Literature 1] Japanese Patent No. 4183742

Non Patent Literature

[Non Patent Literature 1] Nature 448, 313-317
[Non Patent Literature 2] N Eng J Med, 346: 1185-1193, 2002
[Non Patent Literature 3] Science 302: 415-419, 2003
[Non Patent Literature 4] Science 324: 797-801, 2009
[Non Patent Literature 5] Proc Jpn Acad Ser B Phys Biol Sci. 2009; 85 (8): 348-62
[Non Patent Literature 6] Nature Biotechnol 26 (3): 313-315, 2008
[Non Patent Literature 7] PNAS, 111: 12426-12431, 2014
[Non Patent Literature 8] N Eng J Med, 346: 1185-1193, 2002
[Non Patent Literature 9] Science 302: 415-419, 2003

SUMMARY OF INVENTION

Technical Problem

Induced stem cells such as iPS cells are established by the transfer of inducers, such as genes, into cells. These are then expansion-cultured, and cryopreserved. However, production and industrialization of clinical iPS cells (e.g., GLP or GMP grade) present the following problems:

1) Cost

The clinical iPS cells need to be produced and preserved in a completely clean and sterile "clean room". It is very expensive, however, to maintain the required level of cleanliness. Therefore, the production of iPS cells is costly, which presents a significant hurdle to industrialization.

2) Quality

The procedures, from the establishment of stem cells to the preservation thereof, are complicated and require many manual techniques. In addition, the production of stem cells partly depends on operator skills. Therefore, the iPS cells may vary in quality depending on the producers, or the experimental batch.

3) Time

In order to prevent cross-contamination with iPS cells belonging to individuals other than the specified donor, iPS cells from only a single person are produced at any given time period within a clean room. Furthermore, both the establishment and quality evaluation of iPS cells take a long time. Since iPS cells are only produced for one individual at a time per room, the production of iPS cells for many individuals takes a very long time.

4) Human Resources

As mentioned above, the production of iPS cells largely depends on manual procedures at present. Meanwhile, only a small number of technicians have the necessary skills to produce clinical iPS cells.

The series of procedures from the establishment of stem cells to their preservation thereof is disadvantageously complicated. In response to this, an objective of the present invention is to provide a stem cell manufacturing system which makes it possible to manufacture stem cells.

(Objective as to Method for Inducing Stem Cells, Floating Culture Method for Stem Cells, and Floating Culture Vessel for Stem Cells)

The culture of iPS cells in an adherent culture system requires a culture dish and therefore requires a very large space, resulting in poor culture efficiency. After induction of iPS cells or during expansion culture thereof, the iPS cells must be detached from the culture dish. The process of detaching iPS cells from the culture dish, however, largely damages the iPS cells. In addition, these procedures are complicated and unsuitable for mechanization.

In the case of preparing mouse-derived feeder cells, producing and expansion-culturing iPS cells on a layer of feeder cells in a culture dish, the iPS cells are contaminated with animal-derived components. Therefore, the iPS cells cocultured with feeder cells are inappropriate for clinical utilization. Alternatively, the production and expansion culture of iPS cells without feeder cells (feeder-free conditions) stress the iPS cells. This stress makes it likely that the iPS cells develop karyotype abnormalities, or chromosomal damage. Moreover, when the feeder cells are not used, a special coating must be applied to the culture dish, which further complicates the procedures.

In the case of culturing iPS cells in an adherent culture system, the iPS cells can proliferate merely two-dimensionally and therefore disadvantageously exhibit poor growth efficiency.

By contrast, it may be possible to culture iPS cells in a three-dimensional culture (floating culture) system. In conventional floating culture systems, however, the culture solution must be continuously stirred to prevent the iPS cells from sinking down. However, when the culture solution is stirred, the iPS cells collide with each other, and are thus damaged. This disadvantageously causes cell death or karyotype abnormalities.

In conventional floating culture systems, iPS cells randomly aggregate and associate with each other to form cell clusters (colonies) of various sizes. Therefore, a uniform size distribution cannot be maintained among the colonies. If colonies become too large, nutrients or growth factors are unable to diffuse to the cells at the center of the colony, which results in differentiation or cell death of these innermost cells. Conversely, if colonies are too small, they are unsuitable for subculture.

iPS cells are derived from a single somatic cell. Therefore, each iPS cell line, to a small extent, may have distinctive properties. Thus, it is very important to independently culture each colony and establish separate iPS cell lines. In this regard, when culturing iPS cells in a floating culture system, it is necessary to ensure that colonies of the iPS cells grow independently and separate from one another.

In an adherent culture system, the iPS cells, each derived from a single somatic cell, independently form colonies. As mentioned above, however, in conventional floating culture systems, iPS cells randomly aggregate with each other to form colonies. Therefore, the clonality cannot be maintained for the colonies produced in conventional floating systems. As a result, no attempt at inducing and culturing iPS cells via conventional floating culture systems has yet successfully produced iPS colonies derived from an individual cell. Correspondingly, no method for conventional floating culture has been developed which makes it possible to establish independent iPS cell lines.

Thus, another objective of the present invention is to provide a method for inducing stem cells, a floating culture method for stem cells, and a floating culture vessel for stem cells which makes it possible to culture iPS cells with isolated and separate colonies.

(Objective as to Method for Producing Induced Pluripotent Stem Cells)

Another objective of the present invention is to provide a method for producing clinically available stem cells.

(Objective as to Method for Producing Particular Somatic Cells from Animal Cells)

Another objective of the present invention is to provide a method to efficiently produce, in a short period of time, and without incurring genetic damage, a particular type of somatic cell from another type of animal cell.

Solution to Problem

An aspect of the present invention provides a stem cell manufacturing system comprising: (a) a pre-transfer cell solution sending channel through which a solution containing cells flows; (b) an inducer solution sending mechanism which sends a pluripotency inducer into the pre-transfer cell solution sending channel; (c) an inducer transfer apparatus which is connected to the pre-transfer cell solution sending channel and transfers the pluripotency inducer into the cells to produce cells harboring the inducer; (d) a cell cluster production apparatus which cultures the cells harboring the inducer to produce a plurality of cell clusters consisting of stem cells; (e) a packaging apparatus which sequentially packages the plurality of cell clusters; and (f) a container which houses the pre-transfer cell solution sending channel, the inducer solution sending mechanism, the inducer transfer apparatus, the cell cluster production apparatus, and the packaging apparatus.

The above stem cell manufacturing system may further comprise a separation apparatus which separates cells from blood, wherein a solution containing the cells separated by the separation apparatus may flow through the pre-transfer cell solution sending channel.

In the above stem cell manufacturing system, the cell cluster production apparatus may comprise: a reprogramming culture apparatus which cultures the cells harboring the inducer produced by the inducer transfer apparatus; a first division mechanism which divides cell clusters consisting of stem cells established by the reprogramming culture apparatus into a plurality of cell clusters; an expansion culture apparatus which expansion-cultures the plurality of cell clusters divided by the first division mechanism; a second division mechanism which divides cell clusters consisting of stem cells expansion-cultured by the expansion culture apparatus into a plurality of cell clusters; and a cell cluster delivery mechanism which sequentially sends the plurality of cell clusters into the packaging apparatus.

The reprogramming culture apparatus may comprise a first culture solution replenishment apparatus which replenishes the cells harboring the inducer with a culture solution, and the expansion culture apparatus may comprise a second culture solution replenishment apparatus which replenishes the plurality of cell clusters with a culture solution.

The above stem cell manufacturing system may further comprise: a reprogramming culture photography apparatus which photographs the cells cultured by the reprogramming culture apparatus; and an expansion culture photography apparatus which photographs the cells cultured by the expansion culture apparatus, wherein a colorless culture solution may be used in the reprogramming culture apparatus and the expansion culture apparatus.

In the above stem cell manufacturing system, the inside wall of the pre-transfer cell solution sending channel may not be adhesive to cells.

In the above stem cell manufacturing system, the pre-transfer cell solution sending channel and the inducer solution sending mechanism may be disposed on a substrate.

In the above stem cell manufacturing system, the packaging apparatus may freeze the cell clusters using a Peltier device or liquid nitrogen. Alternatively, the packaging apparatus may freeze the cell clusters by a freezing method such as vapor compression or vapor absorption.

The above stem cell manufacturing system may further comprise an air cleaning apparatus which cleans gas in the container.

The above stem cell manufacturing system may further comprise a temperature control apparatus which controls the temperature of gas in the container.

The above stem cell manufacturing system may further comprise a carbon dioxide concentration control apparatus which controls the carbon dioxide concentration of gas in the container.

The above stem cell manufacturing system may further comprise a sterilization apparatus which performs dry heat sterilization or gas sterilization of the inside of the container.

In the above stem cell manufacturing system, the inducer solution sending mechanism, the inducer transfer apparatus, the cell cluster production apparatus, and the packaging apparatus may be regulated on the basis of an operating procedure by a server, and the server may monitor whether or not the inducer solution sending mechanism, the inducer transfer apparatus, the cell cluster production apparatus, and the packaging apparatus are operated on the basis of the operating procedure, and make an operation record.

The above stem cell manufacturing system may further comprise an apparatus which transfers the inducer into the stem cells to differentiate the stem cells into somatic cells.

An aspect of the present invention provides a method for inducing stem cells, comprising inducing stem cells from somatic cells floating-cultured in a gel medium.

In the above method for inducing stem cells, the gel medium may not be stirred. The gel medium may be a medium gelled with deacetylated gellan gum.

In the above method for inducing stem cells, the gel medium may be free from a growth factor. Alternatively, the gel medium may contain a growth factor at a concentration of 40% by weight or lower.

In the above method for inducing stem cells, the gel medium may be free from bFGF. The gel medium may comprise a human ES/iPS culture medium.

An aspect of the present invention also provides a floating culture method for stem cells, comprising floating-culturing stem cells in a gel medium without a growth factor.

An aspect of the present invention also provides a floating culture method for stem cells, comprising floating-culturing stem cells in a gel medium with a growth factor at a concentration of 40% by weight or lower.

An aspect of the present invention also provides a floating culture method for stem cells, comprising floating-culturing stem cells in a gel medium without bFGF.

An aspect of the present invention also provides a floating culture method for stem cells, comprising floating-culturing stem cells in a gel medium with bFGF at a concentration of 400 μg/L or lower.

In the above floating culture method for stem cells, the gel medium may not be stirred. The gel medium may be a medium gelled with deacetylated gellan gum. The gel medium may contain a ROCK inhibitor. The concentration of the stem cells in the gel medium may be $0.1 \times 10^5$ cells/mL or higher.

The above floating culture method for stem cells may further comprise, before the floating culture, dissociating the stem cells into single cells, and placing the stem cells dissociated into single cells in the gel medium.

In the floating culture in the above floating culture method for stem cells, the single cells may form colonies while maintaining their clonality.

The above floating culture method for stem cells may further comprise, before the floating culture, hanging drop-culturing the stem cells using a grating plate to form colonies, and placing the formed colonies in the gel medium.

In the above floating culture method for stem cells, the stem cells may proliferate while maintaining their undifferentiated states.

An aspect of the present invention also provides a floating culture vessel for stem cells comprising: a dialysis tube which accommodates stem cells and a gel medium; and a container which accommodates the dialysis tube, wherein a gel medium is placed around the dialysis tube.

In the above floating culture vessel for stem cells, the molecular weight cut off of the dialysis tube may be 0.1 kDa or larger. The dialysis tube may be made of at least one member selected from cellulose ester, cellulose ester derivatives, regenerated cellulose, and cellulose acetate.

An aspect of the present invention also provides a floating culture method for stem cells comprising: placing stem cells and a gel medium in a dialysis tube; placing the dialysis tube in a container; placing a gel medium around the dialysis tube in the container; and floating-culturing the stem cells in the gel medium in the dialysis tube. The orders of placing the stem cells and the gel medium in the dialysis tube, placing the dialysis tube in the container, and placing the gel medium around the dialysis tube in the container are not particularly limited. For example, a dialysis tube may be placed in a container, and then, the stem cells and the gel medium may be placed in the dialysis tube.

In the above floating culture method for stem cells, a molecular weight cutoff of the dialysis tube may be 0.1 kDa or larger. The dialysis tube may be made of at least one member selected from cellulose ester, cellulose ester derivatives, regenerated cellulose, and cellulose acetate.

In the above floating culture method for stem cells, the gel medium around the dialysis tube may be supplemented with a ROCK inhibitor. The gel medium may not be stirred. The gel medium may be a medium gelled with deacetylated gellan gum.

In the above floating culture method for stem cells, the gel medium may be free from a growth factor. Alternatively, the gel medium may contain a growth factor at a concentration of 40% by weight or lower.

In the above floating culture method for stem cells, the gel medium may be free from bFGF.

In the above floating culture method for stem cells, the concentration of the stem cells in the gel medium may be $0.1 \times 10^5$ cells/mL or higher.

The above floating culture method for stem cells may further comprise, before the floating culture, dissociating the stem cells into single cells, and placing the stem cells dissociated into single cells in the gel medium.

In the floating culture in the above floating culture method for stem cells, the single cells may form colonies while maintaining their clonality.

The above floating culture method for stem cells may further comprise, before the floating culture, hanging drop-culturing the stem cells using a grating plate to form colonies, and placing the formed colonies in the gel medium.

In the above floating culture method for stem cells, the stem cells may proliferate while maintaining their undifferentiated states.

The above floating culture method for stem cells may further comprise replacing the gel medium around the dialysis tube in the container with a fresh gel medium.

The above floating culture method for stem cells may further comprise supplementing the gel medium around the dialysis tube in the container with a fresh gel medium.

In the above floating culture method for stem cells, the gel medium in the dialysis tube may not be replaced. The gel medium may comprise a human ES/iPS culture medium.

An aspect of the present invention also provides a method for inducing stem cells by floating, comprising: placing somatic cells and a gel medium in a dialysis tube; placing the dialysis tube in a container; placing a gel medium around the dialysis tube in the container; and inducing stem cells from the somatic cells floating in the gel medium in the dialysis tube. The orders of placing the somatic cells and the gel medium in the dialysis tube, placing the dialysis tube in the container, and placing the gel medium around the dialysis tube in the container are not particularly limited. For example, the dialysis tube may be placed in the container, and then, the somatic cells and the gel medium may be placed in the dialysis tube.

In the above method for inducing stem cells by floating, a molecular weight cutoff of the dialysis tube may be 0.1 kDa or larger. The dialysis tube may be made of at least one member selected from cellulose ester, cellulose ester derivatives, regenerated cellulose, and cellulose acetate.

In the above method for inducing stem cells by floating, the gel medium may not be stirred. The gel medium may be a medium gelled with deacetylated gellan gum.

In the above method for inducing stem cells by floating, the gel medium may be free from a growth factor.

In the above method for inducing stem cells by floating, the gel medium may be free from bFGF.

The above method for inducing stem cells by floating may further comprise, before the floating culture, dissociating the somatic cells into single cells, and placing the somatic cells dissociated into single cells in the gel medium.

In the floating culture in the above method for inducing stem cells by floating, the single cells may form colonies while maintaining their clonality.

The above method for inducing stem cells by floating may further comprise replacing the gel medium around the dialysis tube in the container with a fresh gel medium.

The above method for inducing stem cells by floating may further comprise supplementing the gel medium around the dialysis tube in the container with a fresh gel medium.

In the above method for inducing stem cells by floating, the gel medium in the dialysis tube may not be replaced. The gel medium may comprise a human ES/iPS culture medium.

An aspect of the present invention also provides a method for producing induced pluripotent stem cells, comprising: preparing somatic cells; and transferring reprogramming factor RNAs into the somatic cells by a lipofection method.

In the above method for producing induced pluripotent stem cells, the somatic cells may be blood cells. The blood cells may be monocytes. The blood cells may be hematopoietic stem/progenitor cells. The blood cells may be CD34-positive. The blood cells may be blood cells separated on condition that the cells are CD34-positive. The blood cells may be CD3-positive. The blood cells may be separated on condition that the cells are CD3-positive.

In the above method for producing induced pluripotent stem cells, the reprogramming factor RNAs may comprise Oct3/4 mRNA, Sox2 mRNA, Klf4 mRNA, and c-Myc mRNA. The reprogramming factor RNAs may further comprise at least one member selected from the group consisting of GLIS1 mRNA, FOXH1 mRNA, L-MYC mRNA, and p53-dn mRNA. The reprogramming factor RNAs may further comprise LIN28A mRNA or LIN28B mRNA.

In the above method for producing induced pluripotent stem cells, an siRNA lipofection reagent or an mRNA lipofection reagent may be used in the lipofection with the reprogramming factor RNAs.

In the above method for producing induced pluripotent stem cells, at least one member selected from Lipofectamine® RNAiMAX transfection reagent, Lipofectamine® MessengerMAX transfection reagent, Stemfect® RNA transfection reagent, and ReproRNA® transfection reagent may be used in the lipofection with the reprogramming factor RNAs.

In the above method for producing induced pluripotent stem cells, the number of the blood cells for the lipofection with the reprogramming factor RNAs may be 1 to $1 \times 10^8$ cells. The amounts of the reprogramming factor RNAs for the lipofection with the reprogramming factor RNAs may be 5 ng to 50 µg per run. The amount of the lipofection reagent for the lipofection with the reprogramming factor RNAs may be 0.1 µL to 500 µL per run. The lipofection with the reprogramming factor RNAs may be performed for 0.1 hours or longer and 24 hours or shorter per run. The lipofection with the reprogramming factor RNAs may be performed a plurality of times.

In the above method for producing induced pluripotent stem cells, the medium used in the lipofection with the reprogramming factor RNAs may be Opti-MEM®.

The above method for producing induced pluripotent stem cells may further comprise separating the monocytes from blood using a filter.

An aspect of the present invention also provides a method for producing particular somatic cells from animal cells, comprising: preparing animal cells; and transferring an inducer RNA into the animal cells by lipofection, to differentiate the animal cells into somatic cells.

In the above method for producing particular somatic cells from animal cells, the animal cells may be stem cells. The stem cells may be induced pluripotent stem cells. The stem cells may be iPS cells. The stem cells may be embryonic stem cells.

In the above method for producing particular somatic cells from animal cells, the animal cells may be human fibroblasts. Alternatively, the animal cells may be blood cells.

In the above method for producing particular somatic cells from animal cells, the inducer RNA may comprise an mRNA corresponding to a drug resistance gene.

The above method for producing particular somatic cells from animal cells may further comprise selecting cells that exhibit drug resistance after the lipofection.

The above method for producing particular somatic cells from animal cells, the inducer RNA may comprise an mRNA corresponding to puromycin resistance gene.

The above method for producing particular somatic cells from animal cells may further comprise selecting cells that exhibit puromycin resistance after the lipofection.

In the above method for producing particular somatic cells from animal cells, the somatic cells may be neuronal cells. The inducer RNA may comprise Ngn2 mRNA. The induced neuronal cells may be Ngn2-positive. The induced neuronal cells may be β-III Tubulin-, MAP2-, PsA-NCAM-, or vGlut-positive.

In the above method for producing particular somatic cells from animal cells, MessengerMAX® may be used in the lipofection with the inducer RNA.

In the above method for producing particular somatic cells from animal cells, the number of the cells for the lipofection with the inducer RNA may be $1\times10^4$ to $1\times10^8$ cells. The amount of the inducer RNA for the lipofection with the inducer RNA may be 200 ng to 5000 ng per run. The amount of the lipofection reagent for the lipofection with the inducer RNA may be 0.1 μL to 100 μL per run.

In the above method for producing particular somatic cells from animal cells, the medium used in the lipofection with the inducer RNA may be Opti-MEM®.

In the above method for producing particular somatic cells from animal cells, the animal cells may be differentiated into the somatic cells within ten days from the lipofection with the inducer RNA.

In the above method for producing particular somatic cells from animal cells, the transfer of the inducer RNA into the animal cells by lipofection may be repeated a plurality of times.

In the above method for producing particular somatic cells from animal cells, the animal cells may be cultured on a substrate coated with basement membrane matrix.

In the above method for producing particular somatic cells from animal cells, the animal cells may be cultured in a medium with B18R. Alternatively, the animal cells may be cultured in a medium without B18R.

Advantageous Effects of Invention

The present invention makes it possible to provide a stem cell manufacturing system which enables the manufacture of stem cells.

(Advantageous Effects of Method for Inducing Stem Cells, Floating Culture Method for Stem Cells, and Floating Culture Vessel for Stem Cells)

The present invention makes it possible to provide a method for inducing stem cells, a floating culture method for stem cells, and a floating culture vessel for stem cells which enables iPS cells to be cultured with their colonies separated.

(Advantageous Effects of Method for Producing Induced Pluripotent Stem Cells)

The present invention makes it possible to provide a method for producing clinically available induced pluripotent stem cells.

(Advantageous Effects of Method for Producing Particular Somatic Cells from Animal Cells)

The present invention makes it possible to provide a method for producing particular somatic cells from animal cells which enables the efficient production of the particular somatic cells in a short period without damaging the genes of the animal cells.

BRIEF DESCRIPTION OF DRAWINGS

FIG. 1 is a schematic view of the stem cell manufacturing system according to an embodiment of the present invention.

FIG. 2 is a schematic cross-sectional view of one example of a post-transfer cell solution sending channel in the stem cell manufacturing system according to an embodiment of the present invention.

FIG. 3 is a schematic cross-sectional view of one example of a post-transfer cell solution sending channel in the stem cell manufacturing system according to an embodiment of the present invention.

FIG. 4 is a schematic view of a culture bag used in the stem cell manufacturing system according to an embodiment of the present invention.

FIG. 5 is a schematic view showing the floating culture vessel for stem cells according to a second embodiment of the present invention.

FIG. 6 is a photograph of the colonies of iPS cells according to Example 1.

FIG. 7 is a photograph of the colonies of iPS cells according to Example 1.

FIG. 8 is a photograph of the colonies of iPS cells according to Example 1.

FIG. 9 is a graph showing the status of differentiation of the colonies of iPS cells according to Example 1.

FIG. 10 is a photograph of the colonies of iPS cells according to Example 2.

FIG. 11 is a photograph of the colonies of iPS cells according to Example 3.

FIG. 12 is a photograph of the colonies of iPS cells according to Example 3.

FIG. 13 is a photograph of iPS cells according to Example 4.

FIG. 14 is a graph showing the number of colonies of iPS cells according to Example 4.

FIG. 15 is a photograph of the colonies of iPS cells according to Example 4.

FIG. 16 is a photograph of the colonies of iPS cells according to Example 5.

FIG. 17 is a graph showing the rate of colony formation for each density of the iPS cells according to Example 5.

FIG. 18 is a graph showing the rate of colony formation for each amount of a medium according to Example 5.

FIG. 19 is a photograph of iPS cells according to Example 6.

FIG. 20 is a graph showing the number of colonies of iPS cells according to Example 6.

FIG. 21 is a photograph of the colonies of iPS cells according to Example 7.

FIG. 22 is a graph showing the number of colonies of iPS cells for each culture condition according to Example 7.

FIG. 23 is a photograph of the colonies of iPS cells for each medium according to Example 7.

FIG. 24 is a graph showing the status of differentiation of the colonies of iPS cells according to Example 7.

FIG. 25 is a photograph of iPS cells according to Example 8.

FIG. 26 is a graph showing the rate of colony formation for each amount of a medium according to Example 8.

FIG. 27 is a photograph of a gel medium according to Example 9.

FIG. 28 is a photograph of the colonies of iPS cells according to Example 9.

FIG. 29 is a photograph of the colonies of iPS cells according to Example 10.

FIG. 30 is a photograph of the colonies of iPS cells according to Example 11.

FIG. 31 is a photograph of the colonies of iPS cells according to Example 12.

FIG. 32 is a graph showing the size of the colonies of iPS cells according to Example 12.

FIG. 33 is a photograph of the colonies of iPS cells according to Example 12.

FIG. 34 is a graph showing the status of differentiation of the colonies of iPS cells according to Example 12.

FIG. 35 is a fluorescence microscope photograph according to Example 13.

FIG. 36 is a graph showing analysis results using a fluorescence-activated flow cytometer according to Example 13.

FIG. 37 is a photograph of cells according to Example 14.

FIG. 38 is a photograph of cells according to Example 14.

FIG. 39 is a graph showing the percentages of transfection efficiency and survival rate according to Example 14.

FIG. 40 is a photograph of cells according to Example 15.

FIG. 41 is a photograph taken by the observation under a fluorescence microscope of cells according to Example 15.

FIG. 42 is a graph showing the percentage of TUJ-1-positive cells according to Example 15.

FIG. 43 shows photographs of cells according to Example 15.

FIG. 44 is a schematic view of a method for transfection according to Example 16.

FIG. 45 is a photograph of cells according to Example 16.

FIG. 46 shows photographs of cells according to Example 16.

DESCRIPTION OF EMBODIMENTS

Hereinafter, embodiments of the present invention will be described. In the following description of the drawings, the same or similar reference signs will be used to designate the same or similar portions. However, the drawings are schematic. Thus, specific dimensions, etc., should be judged in light of the description below. Also, it should be understood that dimensional relationships or ratios may differ among the drawings.

First Embodiment

The stem cell manufacturing system according to the first embodiment of the present invention, as shown in FIG. 1, comprises: a separation apparatus 10 which separates cells from blood; a pre-transfer cell solution sending channel 20 through which a solution containing the cells separated by the separation apparatus 10 flows; an inducer solution sending mechanism 21 which sends a pluripotency inducer into the pre-transfer cell solution sending channel 20; an inducer transfer apparatus 30 which is connected to the pre-transfer cell solution sending channel 20 and transfers the pluripotency inducer into the cells to produce cells harboring the inducer; a cell cluster production apparatus 40 which cultures the cells harboring the inducer to produce a plurality of cell clusters consisting of stem cells; and a packaging apparatus 100 which sequentially packages the plurality of cell clusters.

The stem cell manufacturing system further comprises a container 200 which houses the separation apparatus 10, the pre-transfer cell solution sending channel 20, the inducer solution sending mechanism 21, the inducer transfer apparatus 30, the cell cluster production apparatus 40, and the packaging apparatus 100.

The stem cell manufacturing system may further comprise: an air cleaning apparatus which cleans gas in the container 200; a temperature control apparatus which controls the temperature of gas in the container 200; and a carbon dioxide concentration control apparatus which controls the carbon dioxide ($CO_2$) concentration of gas in the container 200. The air cleaning apparatus may comprise a cleanliness sensor which monitors the cleanliness of gas in the container 200. The air cleaning apparatus cleans air in the container 200 using, for example, a HEPA (high efficiency particulate air) filter. The air cleaning apparatus maintains the cleanliness of air in the container 200 at a cleanliness of between ISO 1 and ISO 6 according to the ISO Standard 14644-1, for example. The temperature control apparatus may comprise a temperature sensor which monitors the temperature of gas in the container 200. The $CO_2$ concentration control apparatus may comprise a $CO_2$ concentration sensor which monitors the $CO_2$ concentration of gas in the container 200.

The container 200 is provided with, for example, a door. In a state where the door is closed, the inside is completely sealed so that the cleanliness, temperature, and $CO_2$ concentration of inside air can be kept constant. The container 200 is preferably transparent so that the internal state of the apparatus can be observed from the outside. The container 200 may be a glove box integrally comprising gloves such as rubber gloves.

The separation apparatus 10 receives, for example, a vial containing human blood. The separation apparatus 10 comprises, for example, an anticoagulant tank which stores an anticoagulant such as ethylenediamine tetraacetic acid (EDTA), heparin, and Acid Citrate Dextrose Formula A solution (ACD-A solution, Terumo Corp.). The separation apparatus 10 adds the anticoagulant from the anticoagulant tank to the human blood using a pump or the like.

The separation apparatus 10 comprises, for example, a reagent tank for separation which stores a reagent for monocyte separation such as Ficoll-Paque PREMIUM® (GE Healthcare Japan Corp.). The separation apparatus 10 dispenses the reagent for monocyte separation at 5 mL/tube to, for example, two 15-mL tubes from the reagent tank for separation using a pump or the like. Note that a resin bag may be used instead of the tube.

The separation apparatus 10 further comprises a buffer solution tank which stores a buffer solution such as phosphate-buffered saline (PBS). The separation apparatus 10 dilutes, for example, 5 mL of the human blood by adding 5 mL of the buffer solution from the buffer solution tank using a pump or the like. In addition, the separation apparatus 10 adds 5 mL of the diluted human blood onto the reagent for monocyte separation in each tube using a pump or the like.

The separation apparatus 10 further comprises a centrifuge in which the temperature can be set. The centrifuge temperature is set to, for example, 18° C. The separation apparatus 10 places each tube containing the reagent for monocyte separation and the human blood, etc., in a holder of the centrifuge using a transportation apparatus or the like. The centrifuge centrifuges the solution in the tube, for example, at 400×g for 30 minutes. A resin bag may be centrifuged instead of the tube.

After the centrifugation, the separation apparatus 10 recovers a white cloudy intermediate layer composed of the monocytes in the solution in the tube using a pump or the like. The separation apparatus 10 sends the recovered monocyte suspension into the pre-transfer cell solution sending channel 20 using a pump or the like. Alternatively, the separation apparatus 10 further adds, for example, 12 mL of PBS to 2 mL of the recovered monocyte solution and places the tube in a holder of the centrifuge. The centrifuge centrifuges the solution in the tube, for example, at 200×g for ten minutes.

After the centrifugation, the separation apparatus 10 removes the supernatant of the solution in the tube by aspiration using a pump or the like, and suspends the monocyte solution in the tube by adding 3 mL of a monocyte culture medium such as X-VIVO 10® (Lonza Japan Ltd.). The separation apparatus 10 sends the monocyte suspension into the pre-transfer cell solution sending channel 20 using a pump or the like. The separation apparatus 10 may separate the monocytes from the blood using a dialysis membrane. Alternatively, in the case of using somatic cells, such as fibroblasts, separated in advance from the skin or the like, the separation apparatus 10 may be unnecessary.

The separation apparatus 10 may separate cells suitable for induction by a method other than centrifugal separation. When the cells to be separated are, for example, T cells, cells positive for any of CD3, CD4, and CD8 may be separated by panning. When the cells to be separated are vascular endothelial progenitor cells, cells positive for CD34 may be separated by panning. When the cells to be separated are B cells, cells positive for any of CD10, CD19, and CD20 may be separated by panning. The separation approach is not limited to panning, and the cells may be separated by a magnetic cell separation method, flow cytometry, or other methods. Alternatively, the separation apparatus 10 may separate cells suitable for induction by methods described in embodiments mentioned later. For example, as described in the fifth embodiment, the cells suitable for induction may be separated using a magnetic separation apparatus on the basis of a cell surface marker. Alternatively, the cells suitable for induction may be separated using a filter. The cells to be induced are not limited to blood cells and may be fibroblasts or the like.

The inducer solution sending mechanism 21 comprises an inducer transfer reagent tank which stores an inducer transfer reagent solution or the like. The inducer transfer reagent solution such as a gene transfer reagent solution contains, for example, an electroporation solution such as Human T Cell Nucleofector® (Lonza Japan Ltd.) solution, a supplement solution, and a plasmid set. The plasmid set contains, for example, 0.83 μg of pCXLE-hOCT3/4-shp53-F, 0.83 μg of pCXLE-hSK, 0.83 μg of pCE-hUL, and 0.5 μg of pCXWB-EBNA1. Alternatively, the inducer transfer reagent solution may contain reagents or the like described in the fourth and fifth embodiments mentioned later. For example, as described in the fifth embodiment, an RNA encoding reprogramming factors may be transferred into the cells by a lipofection method. The inducer solution sending mechanism 21 sends the inducer transfer reagent solution into the pre-transfer cell solution sending channel 20 using a micropump or the like such that the monocyte suspension is suspended in the inducer transfer reagent solution.

The inside wall of the pre-transfer cell solution sending channel 20 may not be adhesive to cells by coating with poly-HEMA (poly-2-hydroxyethyl methacrylate) so as to prevent cells from adhering thereto. Alternatively, a material that resists cell adhesion may be used as the material for the pre-transfer cell solution sending channel 20. Also, a $CO_2$-permeable material having a high thermometric conductivity may be used as the material for the pre-transfer cell solution sending channel 20 so that the internal conditions of the pre-transfer cell solution sending channel 20 are equivalent to the controlled temperature and $CO_2$ concentration in the container 200. The pre-transfer cell solution sending channel 20 may be further provided with a back-flow preventing valve from the viewpoint of preventing contamination.

The inducer transfer apparatus 30 connected to the pre-transfer cell solution sending channel 20 is, for example, an electroporator, which receives the mixed solution of the inducer transfer reagent solution and the monocyte suspension and carries out the electroporation of the monocytes with the plasmids. After the electroporation, the inducer transfer apparatus 30 adds a monocyte culture medium to a solution containing the monocytes electroporated with the plasmids. The inducer transfer apparatus 30 sends the solution containing the monocytes electroporated with the plasmids (hereinafter, referred to as "cells harboring the inducer") to a post-transfer cell solution sending channel 31 using a pump or the like. Note that the inducer transfer apparatus 30 is not limited to an electroporator. The inducer transfer apparatus 30 may transfer the inducer into the cells by methods described in the fourth and fifth embodiments mentioned later. The medium may be a gel medium. In this case, the gel medium may be free from, for example, a growth factor such as basic fibroblast growth factor (bFGF). Alternatively, the gel medium may contain a growth factor such as bFGF at a low concentration of 400 μg/L or lower, 40 μg/L or lower, or 10 μg/L or lower. The gel medium may be free from tgf-β or may contain tgf-β at a low concentration of 600 ng/L or lower, 300 ng/L or lower, or 100 ng/L or lower.

The inside wall of the post-transfer cell solution sending channel 31 may be rendered non-adhesive by coating with poly-HEMA so as to prevent cells from adhering thereto. Alternatively, a material that resists cell adhesion may be used as the material for the post-transfer cell solution sending channel 31. Also, a $CO_2$-permeable material having a high thermometric conductivity may be used as the material for the post-transfer cell solution sending channel 31 so that the internal conditions of the post-transfer cell solution sending channel 31 are equivalent to the controlled temperature and $CO_2$ concentration in the container 200. The post-transfer cell solution sending channel 31 may be further provided with a back-flow preventing valve from the viewpoint of preventing contamination. After the electroporation, many cells die, and dead cells may form cell clusters. Therefore, the post-transfer cell solution sending channel 31 may be provided with a filter which removes dead cell clusters. Alternatively, as shown in FIG. 2, one or more walls which intermittently change the inside diameter may be disposed in the inside of the post-transfer cell solution sending channel 31. Alternatively, as shown in FIG. 3, the inside diameter of the post-transfer cell solution sending channel 31 may be intermittently changed.

The cell cluster production apparatus 40 connected to the post-transfer cell solution sending channel 31 comprises: a reprogramming culture apparatus 50 which cultures the cells harboring the inducer produced by the inducer transfer apparatus 30; a first division mechanism 60 which divides cell clusters consisting of stem cells established by the reprogramming culture apparatus 50 into a plurality of cell clusters; an expansion culture apparatus 70 which expansion-cultures the plurality of cell clusters divided by the first division mechanism 60; a second division mechanism 80 which divides cell clusters consisting of stem cells expansion-cultured by the expansion culture apparatus 70 into a plurality of cell clusters; and a cell cluster delivery mechanism 90 which sequentially sends the plurality of cell clusters into the packaging apparatus 100.

The reprogramming culture apparatus 50 can house a well plate therein. The reprogramming culture apparatus 50 also comprises a pipetting machine. The reprogramming culture apparatus 50 receives a solution containing the cells harboring the inducer from the post-transfer cell solution sending channel 31 and distributes the solution to wells by the pipetting machine. The reprogramming culture apparatus 50 adds a stem cell culture medium such as StemFit® (Ajinomoto Co., Inc.), for example, three, five, and seven days after the cells harboring the inducer are distributed into wells. Basic fibroblast growth factor (basic FGF) may be added as a supplement to the medium. Note that sustained-release beads, such as StemBeads FGF2 (Funakoshi Co., Ltd.), which continuously supply FGF-2 (basic FGF, bFGF, or FGF-b) to the medium may be added to the medium. Since FGF is sometimes unstable, the FGF may be stabilized by coupling a heparin-mimicking polymer to the FGF. The reprogramming culture apparatus 50 further replaces the medium, for example, nine days after the cells harboring the inducer are distributed into wells and subsequently replaces the medium every two days until cell clusters (colonies) of iPS cells exceed 1 mm.

After formation of the cell clusters, the reprogramming culture apparatus 50 recovers the cell clusters by the pipetting machine and adds a recombinant enzyme alternative to trypsin, such as TrypLE Select® (Life Technologies Corp.), to the recovered cell clusters. The reprogramming culture apparatus 50 further places a container containing the recovered cell clusters in an incubator where the cell clusters react with the recombinant enzyme alternative to trypsin at 37° C. for ten minutes in a 5% $CO_2$ environment. Alternatively, the reprogramming culture apparatus 50 may disrupt the cell clusters by pipetting using the pipetting machine. As another alternative, the reprogramming culture apparatus 50 may disrupt the cell clusters by passing the cell clusters through a pipe provided with a filter or a pipe whose inside diameter intermittently changes, as with the post-transfer cell solution sending channel 31 shown in FIG. 2 or 3. Then, the reprogramming culture apparatus 50 adds a medium for pluripotent stem cells, such as StemFit® (Ajinomoto Co., Inc.), to a solution containing the disrupted cell clusters.

The culture in the reprogramming culture apparatus 50 may be performed in a $CO_2$-permeable bag rather than in the well plate. The culture may be an adherent culture or may be a floating culture. In the case of floating culture, stirring the culture may be performed. The medium may be in an agar form. Examples of the medium in an agar form include gellan gum polymer. When the medium in an agar form is used, even in the form of floating culture, stirring is not required and it possible to produce a single cell cluster derived from one cell because the cells neither sink down nor adhere. The culture in the reprogramming culture apparatus 50 may be a hanging drop culture.

The reprogramming culture apparatus 50 may comprise a first culture solution replenishment apparatus which replenishes the well plate or the $CO_2$-permeable bag with a culture solution. The first culture solution replenishment apparatus may recover the culture solution in the well plate or the $CO_2$-permeable bag, filter the culture solution using a filter or a dialysis membrane, and recycle the purified culture solution. In this case, a growth factor or the like may be added to the culture solution to be recycled. The reprogramming culture apparatus 50 may further comprise, for example, a temperature control apparatus which controls the temperature of the culture solution, and a humidity control apparatus which controls humidity near the culture solution.

In the reprogramming culture apparatus 50, for example, the cells may be placed in a culture solution-permeable bag 301, such as a dialysis membrane, as shown in FIG. 4, and the culture solution-permeable bag 301 may be placed in a culture solution-impermeable and $CO_2$-permeable bag 302, while a culture solution may be placed in the bags 301 and 302. A plurality of bags 302 containing a fresh culture solution may be prepared, and the reprogramming culture apparatus 50 may replace the bag 302 in which the bag 301 containing the cells is placed, with another bag 302 containing a fresh culture solution at a predetermined time interval. Note that the culture method in the reprogramming culture apparatus 50 is not limited to the methods described above, and the culture may be performed by methods described in the second and third embodiments mentioned later. For example, as described in the second embodiment, a gel medium may be used. In this case, the gel medium may be free from, for example, a growth factor such as basic fibroblast growth factor (bFGF). Alternatively, the gel medium may contain a growth factor such as bFGF at a low concentration of 400 μg/L or lower, 40 μg/L or lower, or 10 μg/L or lower. The gel medium may be free from tgf-β or may contain tgf-β at a low concentration of 600 ng/L or lower, 300 ng/L or lower, or 100 ng/L or lower. As described in the third embodiment, a floating culture vessel comprising: a dialysis tube which accommodates stem cells and a gel medium; and a container which accommodates the dialysis tube, wherein a gel medium is placed around the dialysis tube, may be used.

The stem cell manufacturing system may further comprise a reprogramming culture photography apparatus which photographs the culture in the reprogramming culture apparatus 50. Note that when a colorless culture solution is used as the culture solution for the reprogramming culture apparatus 50, it is possible to suppress diffuse reflection or autofluorescence that may occur when a colored culture solution is used. Since induced cells and uninduced cells differ in cell shape and size, etc., the stem cell manufacturing system may further comprise an induction status monitor apparatus which calculates the percentage of induced cells by photographing the cells in the reprogramming culture apparatus 50. Alternatively, the induction status monitor apparatus may identify the percentage of induced cells by an antibody immunostaining method or an RNA extraction method. The stem cell manufacturing system may further comprise an uninduced cell removal apparatus which removes uninduced cells by a magnetic cell separation method, flow cytometry, or the like.

A first cell cluster solution sending channel 51 is connected to the reprogramming culture apparatus 50. The reprogramming culture apparatus 50 sends a solution containing the recombinant enzyme alternative to trypsin and the cell clusters into the first cell cluster solution sending channel 51 using a pump or the like. When the cell clusters can be physically disrupted, the recombinant enzyme alternative to trypsin may be unnecessary. The first cell cluster solution sending channel 51 may be connected to a branched channel which has an inside diameter that permits passage of only induced cells having less than a predetermined size and removes uninduced cells having the predetermined size or larger.

The inside wall of the first cell cluster solution sending channel 51 may not be adhesive to cells by coating with poly-HEMA so as to prevent cells from adhering thereto. Alternatively, a material that resists cell adhesion may be used as the material for the first cell cluster solution sending channel 51. Also, a $CO_2$-permeable material having a high thermometric conductivity may be used as the material for the first cell cluster solution sending channel 51 so that the internal conditions of the first cell cluster solution sending channel 51 are equivalent to the controlled temperature and $CO_2$ concentration in the container 200. The first cell cluster solution sending channel 51 may be further provided with a back-flow preventing valve from the viewpoint of preventing contamination.

The first cell cluster solution sending channel 51 is connected to the first division mechanism 60. The first division mechanism 60 comprises, for example, a mesh. When passing through the mesh by hydraulic pressure, the cell clusters contained in the solution are divided into a plurality of cell clusters corresponding to the size of each pore of the mesh. For example, when the mesh has uniform sizes of pores, the sizes of the plurality of cell clusters thus divided are also almost uniform. Alternatively, the first division mechanism 60 may comprise a nozzle. For example, the inside of a substantially conical nozzle is microfabricated in a staircase pattern. When flowing through the nozzle, the cell clusters contained in the solution are divided into a plurality of cell clusters. The expansion culture apparatus 70 is connected to the first division mechanism 60. The solution containing the cell clusters divided by the first division mechanism 60 is sent to the expansion culture apparatus 70.

The expansion culture apparatus 70 can house a well plate therein. The expansion culture apparatus 70 also comprises a pipetting machine. The expansion culture apparatus 70 receives a solution containing the plurality of cell clusters from the first division mechanism 60 and distributes the solution into wells by the pipetting machine. After the cell clusters are distributed into wells, the expansion culture apparatus 70 cultures the cell clusters at 37° C., for example, for approximately eight days, in a 5% $CO_2$ environment. The expansion culture apparatus 70 replaces the medium as necessary.

Then, the expansion culture apparatus 70 adds a recombinant enzyme alternative to trypsin, such as TrypLE Select® (Life Technologies Corp.), to the cell clusters. The expansion culture apparatus 70 further places a container containing the cell clusters in an incubator where the cell clusters react with the recombinant enzyme alternative to trypsin at 37° C. for one minute in a 5% $CO_2$ environment. Then, the expansion culture apparatus 70 adds a medium such as a maintenance culture medium to the solution containing the cell clusters. The expansion culture apparatus 70 further detaches the cell clusters from the container using an automatic cell scraper or the like and sends a solution containing the cell clusters into the first division mechanism 60 via an expansion culture solution sending channel 71.

The culture in the expansion culture apparatus 70 may be performed in a $CO_2$-permeable bag, not in the well plate. The culture may be an adherent culture or may be a floating culture. Alternatively, the culture may be a hanging drop culture. In the case of floating culture, stirring culture may be performed. The medium may be in an agar form. Examples of the medium in an agar form include gellan gum polymer. When the medium in an agar form is used, even in the form of floating culture, stirring is not required because the cells neither sink down nor adhere.

The expansion culture apparatus 70 may comprise a second culture solution replenishment apparatus which replenishes the well plate or the $CO_2$-permeable bag with a culture solution. The second culture solution replenishment apparatus may recover the culture solution in the well plate or the $CO_2$-permeable bag, filter the culture solution using a filter or a dialysis membrane, and recycle the purified culture solution. In this case, a growth factor or the like may be added to the culture solution to be recycled. The expansion culture apparatus 70 may further comprise, for example, a temperature control apparatus which controls the temperature of the culture solution, and a humidity control apparatus which controls humidity near the culture solution.

In the expansion culture apparatus 70 as well, for example, the cells may be placed in a culture solution-permeable bag 301, such as a dialysis membrane, as shown in FIG. 4, and the culture solution-permeable bag 301 may be placed in a culture solution-impermeable and $CO_2$-permeable bag 302, while a culture solution may be placed in the bags 301 and 302. A plurality of bags 302 containing a fresh culture solution may be prepared, and the expansion culture apparatus 70 may replace the bag 302 in which the bag 301 containing the cells is placed, with another bag 302 containing a fresh culture solution at a predetermined time interval. The culture method in the expansion culture apparatus 70 is not limited to the methods described above, and the culture may be performed by methods described in the second and third embodiments mentioned later.

The stem cell manufacturing system may further comprise an expansion culture photography apparatus which photographs the culture in the expansion culture apparatus 70. Note that when a colorless culture solution is used as the culture solution used in the expansion culture apparatus 70, it is possible to suppress diffuse reflection or autofluorescence that may occur when a colored culture solution is used. Since induced cells and uninduced cells differ in cell shape and size, etc., the stem cell manufacturing system may further comprise an induction status monitor apparatus which calculates the percentage of induced cells by photographing the cells in the expansion culture apparatus 70. Alternatively, the induction status monitor apparatus may identify the percentage of induced cells by an antibody immunostaining method or an RNA extraction method. The stem cell manufacturing system may further comprise an uninduced cell removal apparatus which removes uninduced cells by a magnetic cell separation method, flow cytometry, or the like.

The cell clusters divided by the first division mechanism 60 are cultured again in the expansion culture apparatus 70. The division of the cell clusters in the first division mechanism 60 and the culture of the cell clusters in the expansion culture apparatus 70 are repeated until a necessary amount of cells is obtained.

A second cell cluster solution sending channel 72 is connected to the expansion culture apparatus 70. The expansion culture apparatus 70 sends a solution containing the expansion-cultured cell clusters detached from the container into the second cell cluster solution sending channel 72 using a pump or the like. The second cell cluster solution sending channel 72 may be connected to a branched channel which has an inside diameter that permits passage of only induced cells having less than a predetermined size and removes uninduced cells having the predetermined size or larger.

The inside wall of the second cell cluster solution sending channel 72 may not be adhesive to cells by coating with poly-HEMA so as to prevent cells from adhering thereto. Alternatively, a material that resists cell adhesion may be used as the material for the second cell cluster solution sending channel 72. Also, a $CO_2$-permeable material having a high thermometric conductivity may be used as the material for the second cell cluster solution sending channel 72 so that the internal conditions of the second cell cluster solution sending channel 72 are equivalent to the controlled temperature and $CO_2$ concentration in the container 200. The second cell cluster solution sending channel 72 may be further provided with a back-flow preventing valve from the viewpoint of preventing contamination.

The second cell cluster solution sending channel 72 is connected to the second division mechanism 80. The second division mechanism 80 comprises, for example, a mesh. When passing through the mesh by hydraulic pressure, the cell clusters contained in the solution are divided into a plurality of cell clusters corresponding to the size of each pore of the mesh. For example, when the mesh has uniform sizes of pores, the sizes of the plurality of cell clusters thus divided are also almost uniform. Alternatively, the second division mechanism 80 may comprise a nozzle. For example, the inside of a substantially conical nozzle is microfabricated in a staircase pattern. When flowing through the nozzle, the cell clusters contained in the solution are divided into a plurality of cell clusters.

The cell cluster delivery mechanism 90 which sequentially sends a plurality of cell clusters to the packaging apparatus 100 is connected to the second division mechanism 80. A pre-packaging cell channel 91 connects between the cell cluster delivery mechanism 90 and the packaging apparatus 100. The cell cluster delivery mechanism 90 sequentially sends the cell clusters divided by the second division mechanism 80 to the packaging apparatus 100 via the pre-packaging cell channel 91 using a pump or the like.

The pre-packaging cell channel 91 may be coated with poly-HEMA so as to prevent cells from adhering thereto. Alternatively, a material that resists cell adhesion may be used as the material for the pre-packaging cell channel 91. Also, a $CO_2$-permeable material having a high thermometric conductivity may be used as the material for the pre-packaging cell channel 91 so that the internal conditions of the pre-packaging cell channel 91 are equivalent to the controlled temperature and $CO_2$ concentration in the container 200. The pre-packaging cell channel 91 may be further provided with a back-flow preventing valve from the viewpoint of preventing contamination.

A cryopreservation solution sending mechanism 110 is connected to the pre-packaging cell channel 91. The cryopreservation solution sending mechanism 110 sends a cell cryopreservation solution into the pre-packaging cell channel 91. As a result, the cell clusters are suspended in the cell cryopreservation solution in the pre-packaging cell channel 91.

The packaging apparatus 100 sequentially freezes the plurality of cell clusters sent via the pre-packaging cell channel 91. For example, every time a cell cluster is received, the packaging apparatus 100 places the cell cluster in a CryoTube and instantly freezes the cell cluster solution, for example, at $-80°$ C. or lower. If a CryoTube having a small surface area per volume is used, freezing tends to be time-consuming. Therefore, it is preferred to use a CryoTube having a large surface area per volume. It is possible to increase the survival rate of cells after thawing by using a CryoTube having a large surface area per volume. Examples of the shape of the CryoTube include, but are not limited to, capillary and spherical shapes. Depending on the required survival rate of cells after thawing, the instant freezing is not necessarily required.

For example, a vitrification method is used in the freezing. In this case, DAP213 (Cosmo Bio Co., Ltd.) or Freezing Medium (ReproCELL Inc.) can be used as the cell cryopreservation solution. The freezing may be performed by an ordinary method other than the vitrification method. In this case, CryoDefend-Stem Cell (R&D Systems, Inc.), STEM-CELLBANKER® (Nippon Zenyaku Kogyo Co., Ltd.), or the like can be used as the cell cryopreservation solution. The freezing may be performed using liquid nitrogen or may be performed using a Peltier device. By using the Peltier device, it is possible to regulate the change in temperature and suppress temperature variations. The packaging apparatus 100 exports the CryoTube to the outside of the container 200. In the case of clinically using the frozen cells, the CryoTube is preferably a completely sealed system. However, the packaging apparatus 100 may package the stem cells in the CryoTube without freezing the stem cells.

The stem cell manufacturing system may further comprise a packaging step photography apparatus which photographs the packaging step in the packaging apparatus 100.

The stem cell manufacturing system may further comprise a sterilization apparatus which sterilizes the inside of the container 200. The sterilization apparatus may be a dry heat sterilization apparatus. Note that the wiring of apparatuses, such as the separation apparatus 10, the pre-transfer cell solution sending channel 20, the inducer solution sending mechanism 21, the inducer transfer apparatus 30, the cell cluster production apparatus 40, and the packaging apparatus 100, which employ electricity is preferably wiring having heat resistance. Alternatively, the sterilization apparatus may sterilize the inside of the container 200 by emitting sterilization gas such as ozone gas, hydrogen peroxide gas, or formalin gas into the container 200.

The stem cell manufacturing system may transmit operation records of the separation apparatus 10, the pre-transfer cell solution sending channel 20, the inducer solution sending mechanism 21, the inducer transfer apparatus 30, the cell cluster production apparatus 40, and the packaging apparatus 100, etc., and images taken by the photography apparatuses to an external server by wire or wirelessly. The external server may analyze, for example, the association of conditions (e.g., inducer transfer conditions, culture conditions, and freezing conditions) with results (e.g., the incomplete reprogramming of stem cells, the failure of stem cell differentiation and proliferation, and chromosomal aberration) using a neural network to extract a condition leading to the results or predict the results. The external server may further regulate the separation apparatus 10, the inducer solution sending mechanism 21, the inducer transfer apparatus 30, the cell cluster production apparatus 40, and packaging apparatus 100, etc. in the stem cell manufacturing system on the basis of a standard operating procedure (SOP), monitor whether or not each apparatus is operated on the basis of SOP, and automatically make an operation record of each apparatus.

The stem cell manufacturing system described above makes it possible to achieve the induction, establishment, expansion culture, and cryopreservation of stem cells such as iPS cells in a lump with full automation.

Other Embodiments

For example, the inducer transfer apparatus 30 may induce cells by RNA transfection, not by electroporation. Alternatively, the cells may be induced by virus (e.g., retrovirus, lentivirus, and Sendai virus) vectors or plasmids. The pre-transfer cell solution sending channel 20, the post-transfer cell solution sending channel 31, the cell cluster solution sending channel 51, the expansion culture solution sending channel 71, the cell cluster solution sending channel 72, and the pre-packaging cell channel 91 may be disposed on a substrate by a microfluidics technique. An apparatus which transfers an inducer ribonucleic acid (RNA) into induced stem cells by lipofection to differentiate the stem cells into somatic cells may be connected to the stem cell manufacturing system. For example, a method described in the sixth embodiment described later can be used as a method for transferring an inducer ribonucleic acid (RNA) into induced stem cells by lipofection to differentiate the stem cells into somatic cells. The somatic cells may be, for example, neuronal cells.

Second Embodiment

The floating culture method for stem cells according to the second embodiment of the present invention comprises floating-culturing stem cells in a gel medium. The stem cells are, for example, induced pluripotent stem (iPS) cells or embryonic stem cells (ES cells). The gel medium is not stirred. The gel medium is free from feeder cells. The stem cells proliferate in the gel medium while remaining in their undifferentiated states.

For example, before the floating culture, the stem cells are dissociated into single cells, and the stem cells dissociated into single cells are placed in the gel medium. The single cells proliferate while maintaining their clonality to form colonies in the gel medium.

The gel medium is prepared, for example, by adding deacetylated gellan gum at a final concentration of 0.5% by weight to 0.001% by weight, 0.1% by weight to 0.005% by weight, or 0.05% by weight to 0.01% by weight to a medium for stem cells.

The gel medium may contain at least one polymer compound selected from the group consisting of gellan gum, hyaluronic acid, rhamsan gum, diutan gum, xanthan gum, carrageenan, fucoidan, pectin, pectic acid, pectinic acid, heparan sulfate, heparin, heparitin sulfate, keratosulfate, chondroitin sulfate, dermatan sulfate, rhamnan sulfate, and salts thereof. The gel medium may contain methylcellulose. Methylcellulose contained therein suppresses the aggregation among the cells.

Alternatively, the gel medium may contain at least one temperature-sensitive gel selected from poly(glycerol monomethacrylate) (PGMA), poly(2-hydroxypropyl methacrylate) (PHPMA), poly(N-isopropylacrylamide) (PNIPAM), amine terminated, carboxylic acid terminated, maleimide terminated, N-hydroxysuccinimide (NHS) ester terminated, triethoxysilane terminated, poly(N-isopropylacrylamide-co-acrylamide), poly(N-isopropylacrylamide-co-acrylic acid), poly(N-isopropylacrylamide-co-butylacrylate), poly(N-isopropylacrylamide-co-methacrylic acid), poly(N-isopropylacrylamide-co-methacrylic acid-co-octadecyl acrylate), and N-isopropylacrylamide.

A human ES/iPS culture medium, for example, Primate ES Cell Medium (ReproCELL Inc.), can be used as the medium for stem cells.

However, the medium for stem cells is not limited thereto, and various stem cell culture media can be used. For example, Primate ES Cell Medium, Reprostem, ReproFF, ReproFF2, ReproXF (ReproCELL Inc.), mTeSR1, TeSR2, TeSRE8, ReproTeSR (STEMCELL Technologies Inc.), PluriSTEM® Human ES/iPS Medium (Merck KGaA), NutriStem® XF/FF Culture Medium for Human iPS and ES Cells, Pluriton reprogramming medium (Stemgent Inc.), PluriSTEM®, StemFit AK02N, StemFit AK03 (Ajinomoto Co., Inc.), ESC-Sure® serum and feeder free medium for hESC/iPS (Applied StemCell, Inc.), and L7® hPSC Culture System (Lonza Japan Ltd.) may be used.

For example, a ROCK inhibitor is added at a final concentration of 1000 µmol/L or higher and 0.1 µmol/L or lower, 100 µmol/L or higher and 1 µmol/L or lower, or 5 µmol/L or higher and 20 µmol/L or lower to the gel medium every day. The ROCK inhibitor added to the gel medium promotes the formation of colonies by the stem cells.

The gel medium may be free from, for example, a growth factor such as basic fibroblast growth factor (bFGF). Alternatively, the gel medium may contain a growth factor such as bFGF at a low concentration of 400 µg/L or lower, 40 µg/L or lower, or 10 µg/L or lower. The gel medium without a growth factor such as bFGF or the gel medium with a growth factor such as bFGF at a low concentration tends to promote the formation of colonies by the stem cells, as compared with a gel medium with a growth factor such as bFGF at a high concentration.

The gel medium may be free from tgf-β or may contain tgf-β at a low concentration of 600 ng/L or lower, 300 ng/L or lower, or 100 ng/L or lower.

The concentration of the stem cells in the gel medium may be, for example, $2\times10^5$ cells/mL or higher, $2.25\times10^5$ cells/mL or higher, or $2.5\times10^5$ cells/mL or higher. If the concentration of the stem cells in the gel medium is lower than $2\times10^5$ cells/mL, the rate of colony formation tends to be decreased.

The floating culture method for stem cells according to the second embodiment of the present invention makes it possible to form stem cell colonies from single cells. Although this method is a floating culture method, the stem cells do not collide with each other because the floating culture method for stem cells does not require stirring the medium. Therefore, it is possible to maintain the clonality of the colonies. Thus, when the stem cells are, for example, iPS cells, it is possible to ensure the clonality of iPS cells derived from one somatic cell. Further, since the stem cells do not collide with each other, the stem cell colonies can maintain homogeneous sizes. Moreover, the floating culture method makes it possible to culture a large number of colonies in a small space as compared with the adherent culture method. Note that stem cell clusters may be maintenance-cultured in the floating culture.

A growth factor such as bFGF or Tgf-β has been thought to be essential for the culture of ES/iPS cells since the discovery of ES/iPS cells. However, a growth factor such as bFGF is rapidly decomposed under a culture condition of approximately 37° C. Therefore, it is necessary to replace a culture solution with bFGF or Tgf-β with a fresh one every day or to add bFGF or Tgf-β, etc. thereto every day. The bFGF used for culture is usually a recombinant protein. A recombinant protein at a clinical grade needs to be produced according to very strict rules.

When the concentration of bFGF is, for example, a low concentration of 10 ng/mL, it has been considered that mouse-derived fibroblasts need to be used as feeder cells. However, stem cells cocultured with feeder cells derived from an animal such as a mouse cannot be used in transplantation or regenerative medicine. This has been a bottleneck in the clinical utilization of stem cells.

Although a feeder-free culture solution for stem cells, which does not employ feeder cells, has also been developed, the feeder-free culture solution usually contains bFGF in 25 times the amount of that contained in a culture solution using feeder cells and contains bFGF at a very high concentration such as 100 ng/mL. However, it is difficult to culture ES/iPS cells without karyotype abnormalities using a feeder-free culture solution containing a high concentration of bFGF. Thus, many iPS cells are destroyed. ES/iPS cells cultured in the feeder-free culture solution containing a high concentration of bFGF tend to be less likely to differentiate into particular somatic cells. Therefore, the feeder-free culture solution is partly responsible for decreasing the efficiency of production of somatic cells necessary for transplantation from stem cells.

By contrast, the floating culture method for stem cells according to the second embodiment of the present invention makes it possible to culture and proliferate the stem cells without the use of feeder cells while maintaining their undifferentiated states. Even though feeder cells are not used, the floating culture method for stem cells according to the second embodiment of the present invention makes it possible to culture and proliferate the stem cells without the use of a growth factor such as bFGF or with the use of a growth factor such as bFGF at a low concentration while maintaining their undifferentiated states.

Third Embodiment

The floating culture vessel for stem cells according to the third embodiment of the present invention, as shown in FIG. 5, comprises: a dialysis tube which accommodates stem cells and a gel medium; and a container which accommodates the dialysis tube, wherein a gel medium is placed around the dialysis tube.

The dialysis tube is permeable to, for example, a ROCK inhibitor. A molecular weight cutoff of the dialysis tube is 0.1 kDa or larger, 10 kDa or larger, or 50 kDa or larger. The dialysis tube is made of, for example, cellulose ester, ethylcellulose, cellulose ester derivatives, regenerated cellulose, polysulfone, polyacrylonitrile, polymethyl methacrylate, an ethylene-vinyl alcohol copolymer, a polyester-based polymer alloy, polycarbonate, polyamide, cellulose acetate, cellulose diacetate, cellulose triacetate, cuprammonium rayon, saponified cellulose, a hemophan membrane, a phosphatidylcholine membrane, or a vitamin E-coated membrane. A conical tube such as a centrifugal tube can be used as the container. The container is made of, for example, polypropylene.

The stem cells to be placed in the dialysis tube are the same as in the second embodiment. Likewise, the gel medium to be placed in the dialysis tube is the same as in the second embodiment. However, the gel medium to be placed in the dialysis tube may be free from a ROCK inhibitor. The gel medium to be placed around the dialysis tube in the container is the same as in the second embodiment. The gel medium to be placed around the dialysis tube in the container contains a ROCK inhibitor.

During the floating culture of the stem cells in the dialysis tube, the gel medium around the dialysis tube in the container is replaced or supplemented with a fresh gel medium. However, the replacement of the gel medium in the dialysis tube may be unnecessary.

For a conventional floating culture system, it may be difficult to replace a medium without aspirating the cells. However, waste products may accumulate unless the medium is replaced with a fresh medium. Furthermore, the medium may be short of a medium component unless the medium is replaced or supplemented with a fresh medium.

By contrast, by using the floating culture vessel for stem cells according to the third embodiment of the present invention, it is possible to avoid aspirating the stem cells even if the medium around the dialysis tube is replaced with a fresh medium, because the stem cells are in the dialysis tube. In addition, the amount of the medium in the dialysis tube is hardly changed even when the medium around the dialysis tube is replaced with a fresh medium. Therefore, the density of the stem cells in the dialysis tube is not changed. A high concentration of waste products in the dialysis tube moves to the outside of the dialysis tube. The medium component moves from the outside medium of the dialysis tube into the dialysis tube with decrease in the concentration of the medium component of the medium in the dialysis tube. Therefore, it is possible to keep the medium around the stem cells fresh.

Fourth Embodiment

The method for inducing stem cells according to the fourth embodiment of the present invention comprises inducing stem cells from somatic cells floating-cultured in a gel medium. The somatic cells are, for example, fibroblasts. The stem cells are, for example, iPS cells. The gel medium is not stirred. The gel medium is free from feeder cells.

The gel medium is prepared, for example, by adding deacetylated gellan gum at a final concentration of 0.5% by weight to 0.001% by weight, 0.1% by weight to 0.005% by weight, or 0.05% by weight to 0.01% by weight to a medium for stem cells.

The gel medium may contain at least one polymer compound selected from the group consisting of gellan gum, hyaluronic acid, rhamsan gum, diutan gum, xanthan gum, carrageenan, fucoidan, pectin, pectic acid, pectinic acid, heparan sulfate, heparin, heparitin sulfate, keratosulfate, chondroitin sulfate, dermatan sulfate, rhamnan sulfate, and salts thereof. The gel medium may contain methylcellulose. Methylcellulose contained therein suppresses the aggregation among the cells.

Alternatively, the gel medium may contain at least one temperature-sensitive gel selected from poly(glycerol monomethacrylate) (PGMA), poly(2-hydroxypropyl methacrylate) (PHPMA), poly(N-isopropylacrylamide) (PNIPAM), amine terminated, carboxylic acid terminated, maleimide terminated, N-hydroxysuccinimide (NHS) ester terminated, triethoxysilane terminated, poly(N-isopropylacrylamide-co-acrylamide), poly(N-isopropylacrylamide-co-acrylic acid), poly(N-isopropylacrylamide-co-butylacrylate), poly(N-isopropylacrylamide-co-methacrylic acid), poly(N-isopropylacrylamide-co-methacrylic acid-co-octadecyl acrylate), and N-isopropylacrylamide.

A human ES/iPS culture medium, for example, Primate ES Cell Medium (ReproCELL Inc.), can be used as the medium for stem cells.

However, the medium for stem cells is not limited thereto, and various stem cell culture media can be used. For example, Primate ES Cell Medium, Reprostem, ReproFF, ReproFF2, ReproXF (ReproCELL Inc.), mTeSR1, TeSR2, TeSRE8, ReproTeSR (STEMCELL Technologies Inc.), PluriSTEM® Human ES/iPS Medium (Merck KGaA), NutriStem® XF/FF Culture Medium for Human iPS and ES Cells, Pluriton reprogramming medium (Stemgent Inc.), PluriSTEM®, StemFit AK02N, StemFit AK03 (Ajinomoto Co., Inc.), ESC-Sure® serum and feeder free medium for hESC/iPS (Applied StemCell, Inc.), and L7® hPSC Culture System (Lonza Japan Ltd.) may be used. The gel medium is placed in, for example, a tube.

The gel medium may be free from, for example, a growth factor such as basic fibroblast growth factor (bFGF). Alternatively, the gel medium may contain a growth factor such as bFGF at a low concentration of 400 µg/L or lower, 40 µg/L or lower, or 10 µg/L or lower.

The gel medium may be free from tgf-β or may contain tgf-β at a low concentration of 600 ng/L or lower, 300 ng/L or lower, or 100 ng/L or lower.

Example 1

500 mL of Primate ES Cell Medium (ReproCELL Inc.) and 0.2 mL of bFGF (Gibco PHG0266) having a concentration of 10 µg/mL were mixed to prepare a human iPS medium with bFGF.

Deacetylated gellan gum (Nissan Chemical Industries Ltd.) was added at a concentration of 0.02% by weight to the human iPS medium with bFGF to prepare a human iPS gel medium with bFGF. Further, 5 mL of trypsin having a concentration of 2.5% by weight, 5 mL of collagenase IV having a concentration of 1 mg/mL, 0.5 mL of $CaCl_2$ having a concentration of 0.1 mol/L, 10 mL of KnockOut Serum Replacement® (Invitrogen 10828-028), and 30 mL of purified water were mixed to prepare a dissociation solution generally called a CTK solution.

The CTK solution was added at 300 µL/well to a 6-well dish (Thermo Fisher Scientific 12-556-004) containing iPS cells in the process of culture on feeder cells, and the 6-well dish was incubated for three minutes in a $CO_2$ incubator. Three minutes later, the dish was taken out of the incubator. After confirmation that only the feeder cells were detached from the dish, the CTK solution was removed using an aspirator. After the removal of the CTK solution, the iPS cells were washed by the addition of PBS (Santa Cruz Biotech sc-362183) at 500 µL/well to the 6-well dish, followed by the removal of PBS from the 6-well dish. A dissociation solution (Accutase®) was added at 0.3 mL/well to the 6-well dish, which was then placed in a $CO_2$ incubator and incubated for five minutes. Then, the iPS medium with bFGF was added at 0.7 mL/well to the 6-well dish so that the iPS cells were suspended until becoming single cells.

After the suspension of the iPS cells, 4 mL of the human iPS medium with bFGF was added to a 15-mL centrifugal tube, and the iPS cell suspension was centrifuged at 270 g using a centrifuge. After the centrifugation, the supernatant was removed, and 1 mL of the human iPS medium with bFGF was added to the 15-mL centrifugal tube. The number of the cells was calculated using a hemocytometer. After the cell counting, $5 \times 10^5$ iPS cells were seeded to 15-mL Falcon Tube® (Corning 352096) or a non-adherent dish and subsequently floating-cultured without stirring.

In the 15-mL tube, 2 mL of the human iPS gel medium with bFGF was used. In the non-adherent dish, 2 mL of the human iPS medium with bFGF and without gellan gum was used. A ROCK inhibitor (Selleck Chemicals 51049) was added at 10 µmol/L to each medium. Then, 500 µL of the human iPS gel medium with bFGF was added to the 15-mL tube and the non-adherent dish every day, and 500 µL of the human iPS medium with bFGF was added to the non-adherent dish every day. Also, the ROCK inhibitor was added at a final concentration of 10 µmol/L to the 15-mL tube and the non-adherent dish every day, and the floating culture was continued for seven days.

The results are shown in FIG. 6. As shown in FIG. 6(b), aggregation among iPS cell colonies was notably observed when the iPS cells were cultured using the human iPS medium with bFGF and without gellan gum in the non-adherent dish. By contrast, as shown in FIG. 6(a), conspicuous aggregation was not observed when the iPS cells were cultured using the human iPS gel medium with bFGF in the 15-mL tube. FIG. 7(a) is a photograph taken at day 1 when the iPS cells were cultured using the human iPS gel medium with bFGF in the 15-mL tube. FIG. 7(b) is a photograph taken at day 9 when the iPS cells were cultured using the human iPS gel medium with bFGF in the 15-mL tube. From the photographs of FIGS. 7(a) and 7(b), the iPS cells of different lines were confirmed to form their respective colonies without being aggregated with each other.

FIG. 8(a) is a photograph taken immediately before the colonies of the iPS cells floating-cultured for seven days in the gel medium were reseeded over feeder cells. FIG. 8(b) is a photograph taken three days later when the colonies were morphologically confirmed. As a result, as shown in FIG. 9, 95% more of the colonies were confirmed to be undifferentiated. These results demonstrated that iPS cells can be cultured in a gel medium while maintaining their undifferentiated states.

Example 2

The same human iPS medium with bFGF and human iPS gel medium with bFGF as in Example 1 were prepared. The CTK solution was added at 300 µL/well to a 6-well dish containing iPS cells in the process of culture on feeder cells, and the 6-well dish was incubated for three minutes in a $CO_2$ incubator. Three minutes later, the dish was taken out of the incubator. After confirmation that only the feeder cells were detached from the dish, the CTK solution was removed using an aspirator. After the removal of the CTK solution, the iPS cells were washed by the addition of PBS at 500 µL/well to the dish, followed by the removal of PBS from the dish. Accumax was added at 0.3 mL/well to the dish, which was then placed in a $CO_2$ incubator and incubated for five minutes. Then, the iPS medium with bFGF was added at 0.7 mL/well to the dish so that the iPS cells were suspended until becoming single cells.

After the suspension of the iPS cells, 4 mL of the human iPS medium with bFGF was added to a 15-mL centrifugal tube, and the iPS cell suspension was centrifuged at 270 g using a centrifuge. After the centrifugation, the supernatant was removed, and 1 mL of the human iPS medium with bFGF was added to the 15-mL centrifugal tube. The number of the cells was calculated using a hemocytometer. After the cell counting, $5\times10^5$ iPS cells were seeded to a 15-mL tube and subsequently floating-cultured without stirring.

In the 15-mL tube, 2 mL of the human iPS gel medium with bFGF was used. A ROCK inhibitor was added at 10 μmol/L to each medium. Then, 500 μL of the human iPS gel medium with bFGF was added to the 15-mL tube every day. This gel medium (500 μL) contained 0.5 μL of the ROCK inhibitor. As a control, iPS cells were floating-cultured for seven days under the same conditions as above except that the ROCK inhibitor was not added.

As shown in FIG. 10(a), the iPS cells formed no colonies when the ROCK inhibitor was not added to the human iPS medium with bFGF. By contrast, as shown in FIG. 10(b), the iPS cells formed colonies when the ROCK inhibitor was added to the human iPS medium with bFGF. These results demonstrated that a ROCK inhibitor is effective for the floating culture of iPS cells from single cells.

Example 3

A human iPS gel medium with bFGF was prepared in the same way as in Example 1. Also, a human iPS medium without bFGF which was the same as the human iPS medium with bFGF except for being free from bFGF was prepared. Further, a human iPS gel medium without bFGF which was the same as the human iPS gel medium with bFGF except for being free from bFGF was prepared. In addition, deacylated gellan gum (Nissan Chemical Industries Ltd.) was added at a concentration of 0.02% by weight to a commercially available serum-free, xeno-free, and feeder-free medium for reprogramming to prepare a gel medium for comparison.

Here, the human iPS gel medium with bFGF contained bFGF only at approximately ½s of the concentration of that in the gel medium for comparison.

The CTK solution was added at 300 μL/well to a 6-well dish containing iPS cells in the process of culture on feeder cells, and the 6-well dish was incubated for three minutes in a $CO_2$ incubator. Three minutes later, the dish was taken out of the incubator. After confirmation that only the feeder cells were detached from the dish, the CTK solution was removed using an aspirator. After the removal of the CTK solution, the iPS cells were washed once with PBS. 1 mL of the human iPS medium without bFGF was added thereto, and the iPS cells were scraped up using a scraper and suspended approximately ten times in a 15-mL centrifugal tube so as not to become single cells. Then, 2 mL of the human iPS medium without bFGF was added thereto, and the mixture was divided into 1 mL each of three equal portions, which were centrifuged at 270 g using a centrifuge.

After the centrifugation, the supernatant was removed from the 15-mL centrifugal tube, and 2 mL of the gel medium for comparison, the human iPS gel medium with bFGF, or the human iPS gel medium without bFGF was added to the 15-mL centrifugal tube. From the next day, 500 μL of the same gel medium as the initial one was added to the centrifugal tube every day, and the iPS cells were floating-cultured for seven days.

FIG. 11(a) shows a typical example of colonies of the iPS cells floating-cultured for seven days in the gel medium for comparison prepared from the commercially available feeder-free medium. FIG. 11(b) shows a typical example of colonies of the iPS cells floating-cultured for seven days in the human iPS gel medium with bFGF. FIG. 11(c) shows a typical example of colonies of the iPS cells floating-cultured for seven days in the human iPS gel medium without bFGF.

The iPS cells could be cultured even in the human iPS gel medium without bFGF and the human iPS gel medium with bFGF, which contained bFGF only at approximately ½s of the concentration of that of the gel medium for comparison.

In order to confirm whether or not the colonies of the iPS cells floating-cultured for seven days were undifferentiated, the iPS cells were reseeded over feeder cells, and their colonies were morphologically observed. The upper photographs of FIG. 12 each show the colonies in the gel medium. The middle photographs of FIG. 12 each show the colonies two days after the reseeding of the iPS cells floating-cultured for seven days over feeder cells. In each case, undifferentiated colonies were confirmed to occupy 90% or more. These results demonstrated that iPS cells can be floating-cultured while maintaining their differentiated states even when a gel medium without bFGF or a gel medium having 25 or more times lower than the bFGF concentration of the gel medium for comparison is used.

The lower photographs of FIG. 12 show the colonies seven days after the reseeding of the iPS cells floating-cultured for seven days over feeder cells. These results demonstrated that iPS cells are not differentiated even if floating-cultured in a gel medium and then cultured on feeder cells for a long period (seven days).

Example 4

The same human iPS medium without bFGF, human iPS gel medium with bFGF, and human iPS gel medium without bFGF as in Example 3 were prepared. Also, deacylated gellan gum (Nissan Chemical Industries Ltd.) was added at a concentration of 0.02% by weight to a commercially available serum-free and feeder-free medium to prepare a gel medium for comparison. A ROCK inhibitor was added at a concentration of 10 μmol/L to all of the gel media.

The CTK solution was added at 300 μL/well to a 6-well dish containing iPS cells in the process of culture on feeder cells, and the 6-well dish was incubated for three minutes in a $CO_2$ incubator. Three minutes later, the dish was taken out of the incubator. After confirmation that only the feeder cells were detached from the dish, the CTK solution was removed using an aspirator. After the removal of the CTK solution, the iPS cells were washed by the addition of PBS at 500 μL/well to the 6-well dish, followed by the removal of PBS from the 6-well dish. Accumax was added at 0.3 mL/well to the 6-well dish, which was then placed in a $CO_2$ incubator and incubated for five minutes. Then, the iPS medium with bFGF was added at 0.7 mL/well to the 6-well dish so that the iPS cells were suspended until becoming single cells.

After the suspension of the iPS cells, 4 mL of the human iPS medium without bFGF was added to a 15-mL centrifugal tube, and the iPS cell suspension was centrifuged at 270 g using a centrifuge. After the centrifugation, the supernatant was removed, and 1 mL of the human iPS medium without bFGF was added to the centrifugal tube. The number of the cells was calculated using a hemocytometer.

Then, $5\times10^5$ iPS cells were placed per centrifugal tube, and 2 mL of the human iPS gel medium with bFGF, the human iPS gel medium without bFGF, or the gel medium for comparison was added to the centrifugal tube. From the next day, 500 μL of the same gel medium as the initial one was added to the centrifugal tube every day, and the iPS cells were floating-cultured for seven days.

As a result, as shown in FIG. 13(c), the iPS cells derived from the single cells were unable to be cultured in the gel medium for comparison. By contrast, as shown in FIGS. 13(a) and 13(b), the iPS cells derived from single cells could be cultured in the human iPS gel medium with bFGF and the human iPS gel medium without bFGF. The human iPS gel medium with bFGF had a bFGF concentration of 4 µg/mL, and the gel medium for comparison had a bFGF concentration of 100 µg/mL.

As a result of determining the number of the colonies, as shown in FIG. 14, the iPS cells floating-cultured in the human iPS gel medium without bFGF formed colonies at twice or more the number of the colonies of the iPS cells floating-cultured in the human iPS gel medium with bFGF. These results demonstrated that a low bFGF concentration or the absence of bFGF is preferred for a gel medium.

In addition, iPS cells were dissociated into single cells and cultured for seven days using a medium in which a ROCK inhibitor was added at 10 µmol/L to the human iPS medium with bFGF or the human iPS medium without bFGF supplemented with deacylated gellan gum at 0.02% by weight. In this operation, $5 \times 10^5$ cells were suspended in 1.5 mL of each gel medium, and 1.5 mL of the medium in which a ROCK inhibitor was added at 10 µmol/L to each gel medium was added thereto every day.

A 10-fold amount of PBS was added to the iPS cells cultured for seven days. After centrifugation at 270 g using a centrifuge, the supernatant was discarded, and 0.3 mL of Accumax was added to the culture vessel, which was then placed in a $CO_2$ incubator and incubated for five minutes. Then, 0.7 mL of the human iPS medium with bFGF was added thereto so that the iPS cells were suspended until becoming single cells. After the suspension, 1.5 mL of the human iPS medium (the medium with bFGF for the cells cultured in the medium with bFGF, or the medium without bFGF for the cells cultured in the medium without bFGF) was added thereto, and the iPS cells were cultured for another seven days using a centrifuge in the same way as in the previous seven days. After the culture, an aliquot was reseeded over feeder cells. After three more days, the cells were stained with antibodies against NANOG and OCT3/4 and observed. The results are shown in FIG. 15. The iPS cells cultured in the gel medium for a total of 14 days were positive for the undifferentiation markers NANOG and OCT3/4. These results demonstrated that iPS cells can be cultured by long-term culture in a gel medium while maintaining their undifferentiated states, even when the gel medium without bFGF is used.

Example 5

The same human iPS medium without bFGF and human iPS gel medium without bFGF as in Example 3 were prepared. A ROCK inhibitor was added at a concentration of 10 µmol/L to both of the gel media.

The CTK solution was added at 300 µL/well to a 6-well dish containing iPS cells in the process of culture on feeder cells, and the 6-well dish was incubated for three minutes in a $CO_2$ incubator. Three minutes later, the dish was taken out of the incubator. After confirmation that only the feeder cells were detached from the dish, the CTK solution was removed using an aspirator. After the removal of the CTK solution, the cells were washed by the addition of PBS at 500 µL/well to the 6-well dish, followed by the removal of PBS. Accutase was added at 0.3 mL/well to the 6-well dish, which was then placed in a $CO_2$ incubator and incubated for five minutes. Then, the human iPS medium without bFGF was added at 0.7 mL/well to the 6-well dish so that the iPS cells were suspended until becoming single cells.

After the suspension of the iPS cells, 4 mL of the human iPS medium without bFGF was added to a centrifugal tube, and the iPS cell suspension was centrifuged at 270 g using a centrifuge. After the centrifugation, the supernatant was removed, and 1 mL of the human iPS medium without bFGF was added to the centrifugal tube. The number of the cells was calculated using a hemocytometer.

Then, $1 \times 10^5$, $2.5 \times 10^5$, or $5 \times 10^5$ iPS cells were placed per centrifugal tube, and 2 mL of the human iPS gel medium without bFGF was added thereto. From the next day, 500 µL of the gel medium was added to the centrifugal tube every day, and the iPS cells were floating-cultured for seven days.

FIG. 16 shows a photograph of the colonies at each of the number of the seeding cells. FIG. 17 shows results of determining the ratio of the number of the iPS cells that formed colonies to the number of the seeded iPS cells. The iPS cells seeded at $5 \times 10^5$ cells formed colonies at 10 or more times the number of the colonies of the iPS cells seeded at $1 \times 10^5$ or $2.5 \times 10^5$ cells. These results demonstrated that iPS cells seeded at a low concentration form no colonies.

$1 \times 10^5$ iPS cells were placed per centrifugal tube, and 200 µL, 400 µL, 1000 µL, or 2000 µL of the human iPS gel medium without bFGF was added to the centrifugal tube. From the next day, 100 µL, 200 µL, 5000 µL, or 1000 µL of the gel medium was added to the centrifugal tube every day, and the iPS cells were floating-cultured for seven days.

FIG. 18 shows results of determining the ratio of the number of the iPS cells that formed colonies to the number of the seeded iPS cells. These results demonstrated that iPS cells are less likely to form colonies with increase in the amount of a gel medium, in other words, with decrease in the seeding concentration of the iPS cells.

Example 6

The same human iPS medium without bFGF and human iPS gel medium without bFGF as in Example 3 were prepared.

The CTK solution was added at 300 µL/well to a 6-well dish containing iPS cells in the process of culture on feeder cells, and the 6-well dish was incubated for three minutes in a $CO_2$ incubator. Three minutes later, the dish was taken out of the incubator. After confirmation that only the feeder cells were detached from the dish, the CTK solution was removed using an aspirator. After the removal of the CTK solution, the cells were washed by the addition of PBS at 500 µL/well to the 6-well dish, followed by the removal of PBS. Accumax was added at 0.3 mL/well to the 6-well dish, which was then placed in a $CO_2$ incubator and incubated for five minutes. Then, the human iPS medium without bFGF was added at 0.7 mL/well to the 6-well dish so that the iPS cells were suspended until becoming single cells.

After the suspension of the iPS cells, 4 mL of the human iPS medium without bFGF was added to a 15-mL centrifugal tube, and the iPS cell suspension was centrifuged at 270 g using a centrifuge. After the centrifugation, the supernatant was removed, and 1 mL of the human iPS medium without bFGF was added to the 15-mL centrifugal tube. The number of the cells was calculated using a hemocytometer.

Then, 2 mL of the human iPS gel medium without bFGF containing $5 \times 10^5$ iPS cells was placed in a dialysis module (Spectrum Laboratories G235035) equipped with a dialysis tube having a molecular weight cutoff of 100 kDa. No ROCK inhibitor was placed in the dialysis tube. As shown in FIG. 5, the dialysis module was further placed in a 50-mL centrifugal tube, and 20 mL of the human iPS gel medium without bFGF was placed around the dialysis tube in the centrifugal tube. A ROCK inhibitor was further added at a final concentration of 10 µmol/L to the human iPS gel medium without bFGF around the dialysis tube. As a control, the ROCK inhibitor was not added to some centrifugal tubes. Then, 10 mL of the human iPS gel medium without bFGF around the dialysis tube was replaced with a fresh gel medium every two days, and the floating culture was continued for seven days. The fresh human iPS gel medium without bFGF to be placed for the replacement contained the ROCK inhibitor at a concentration of 10 µmol/L.

As shown in FIG. 20, the iPS cells significantly formed colonies by the culture as shown in FIG. 19(b) when the human iPS gel medium without bFGF supplemented with the ROCK inhibitor was placed around the dialysis tube, as compared with the culture as shown in FIG. 19(a) when the human iPS gel medium without bFGF and the ROCK inhibitor was placed around the dialysis tube.

These results demonstrated that a low molecule such as a ROCK inhibitor passes through the membrane of a dialysis tube. These results also demonstrated that iPS cells can be cultured while the concentration of a medium component in a dialysis tube is maintained.

Example 7

The same human iPS medium without bFGF and human iPS gel medium without bFGF as in Example 3 were prepared.

The CTK solution was added at 300 µL/well to a 6-well dish containing iPS cells in the process of culture on feeder cells, and the 6-well dish was incubated for three minutes in a $CO_2$ incubator. Three minutes later, the dish was taken out of the incubator. After confirmation that only the feeder cells were detached from the dish, the CTK solution was removed using an aspirator. After the removal of the CTK solution, the cells were washed by the addition of PBS at 500 µL/well to the 6-well dish, followed by the removal of PBS from the 6-well dish. Accumax was added at 0.3 mL/well to the 6-well dish, which was then placed in a $CO_2$ incubator and incubated for five minutes. Then, the human iPS medium without bFGF was added at 0.7 mL/well to the 6-well dish so that the iPS cells were suspended until becoming single cells.

After the suspension of the iPS cells, 4 mL of the human iPS medium without bFGF was added to a 15-mL centrifugal tube, and the iPS cell suspension was centrifuged at 270 g using a centrifuge. After the centrifugation, the supernatant was removed, and 1 mL of the human iPS medium without bFGF was added to the centrifugal tube. The number of the cells was calculated using a hemocytometer.

Then, 2 mL of the human iPS gel medium without bFGF containing $5 \times 10^5$ iPS cells was placed in a dialysis tube of a dialysis module. The dialysis module was further placed in a 50-mL centrifugal tube (Corning 352070), and 20 mL of the human iPS gel medium without bFGF was placed around the dialysis tube in the centrifugal tube. A ROCK inhibitor was further added at 10 µmol/L to the human iPS gel medium without bFGF around the dialysis tube. Then, 10 mL of the human iPS gel medium without bFGF around the dialysis tube was replaced with a fresh gel medium every two days, and the floating culture was continued for seven days. The fresh human iPS gel medium without bFGF to be placed for the replacement contained the ROCK inhibitor at a concentration of 10 µmol/L. As a control, the floating-culture was continued for seven days in some centrifugal tubes without replacing the human iPS gel medium without bFGF around the dialysis tube.

As shown in FIG. 22, the individual colonies formed by the iPS cells were found to be large in the case where the human iPS gel medium without bFGF around the dialysis tube was replaced with a fresh gel medium as shown in FIG. 21(a), as compared with the case where the human iPS gel medium without bFGF around the dialysis tube was not replaced as shown in FIG. 21(b). These results demonstrated that the replacement of the human iPS gel medium without bFGF around the dialysis tube promotes the ability of iPS cells to proliferate.

The colonies of the iPS cells floating-cultured for seven days were further reseeded over feeder cells, and the maintenance of the undifferentiated states of the iPS cells was confirmed from the morphology of the colonies. As shown in FIGS. 23 and 24, 80% or more of the colonies maintained their undifferentiated states even if the human iPS gel medium without bFGF around the dialysis tube was or was not replaced.

Example 8

The same human iPS medium without bFGF and human iPS gel medium without bFGF as in Example 3 were prepared.

The CTK solution was added at 300 µL/well to a 6-well dish containing iPS cells in the process of culture on feeder cells, and the dish was incubated for three minutes in a $CO_2$ incubator. Three minutes later, the dish was taken out of the incubator. After confirmation that only the feeder cells were detached from the dish, the CTK solution was removed using an aspirator. After the removal of the CTK solution, the cells were washed by the addition of PBS at 500 µL/well to the 6-well dish, followed by the removal of PBS. Accumax was added at 0.3 mL/well to the 6-well dish, which was then placed in a $CO_2$ incubator and incubated for five minutes. Then, the human iPS medium without bFGF was added at 0.7 mL/well to the 6-well dish so that the iPS cells were suspended until becoming single cells.

After the suspension of the iPS cells, 4 mL of the human iPS medium without bFGF was added to a 15-mL centrifugal tube, and the iPS cell suspension was centrifuged at 270 g using a centrifuge. After the centrifugation, the supernatant was removed, and 1 mL of the human iPS medium without bFGF was added to the centrifugal tube. The number of the cells was calculated using a hemocytometer.

Then, 2 mL of the human iPS gel medium without bFGF containing $5 \times 10^5$ iPS cells was placed in a dialysis tube of a dialysis module. The dialysis module was further placed in a 50-mL centrifugal tube, and 20 mL of the human iPS gel medium without bFGF was placed around the dialysis tube in the centrifugal tube. A ROCK inhibitor was further added at 10 µmol/L to the human iPS gel medium without bFGF around the dialysis tube. Then, 10 mL of the human iPS gel medium without bFGF around the dialysis tube was replaced with a fresh gel medium every two days, and the floating culture was continued for seven days. The fresh human iPS gel medium without bFGF to be placed for the replacement contained the ROCK inhibitor at a concentration of 10 µmol/L.

As a first control, 2 mL of the human iPS gel medium without bFGF containing $5 \times 10^5$ iPS cells was placed in a dialysis tube of a dialysis module. The dialysis tube was further placed in a 50-mL centrifugal tube, and 20 mL of the human iPS medium without bFGF and gellan gum was placed around the dialysis tube in the centrifugal tube. A ROCK inhibitor was further added at 10 µmol/L to the human iPS medium without bFGF and gellan gum around the dialysis tube. Then, 10 mL of the human iPS medium without bFGF and gellan gum around the dialysis tube was replaced with a fresh medium every two days, and the floating culture was continued for seven days.

As a second control, 2 mL of the human iPS gel medium without bFGF containing $5\times10^5$ iPS cells was placed in a 50-mL centrifugal tube without the use of the dialysis tube. Then, 500 μL of the human iPS gel medium without bFGF was added to the 50-mL centrifugal tube once a day, and the floating culture was continued for seven days.

As a result, as shown in FIGS. 25 and 26, the number of the colonies of the iPS cells was increased with the use of dialysis tube as compared without the use of the dialysis tube. Furthermore, the number of the colonies the iPS cells was increased with the use of the human iPS gel medium without bFGF around the dialysis tube as compared with the use of the human iPS medium without bFGF and gellan gum around the dialysis tube.

Example 9: Induction of iPS Cells in Polymer Medium 500 mL of Primate ES Cell Medium (ReproCELL Inc.) and 0.2 mL of bFGF (Gibco PHG0266) having a concentration of 10 μg/mL were mixed to prepare a human iPS medium with bFGF. Also, a human iPS medium without bFGF was prepared from 500 mL of Primate ES Cell Medium (ReproCELL Inc.) without mixing with bFGF (Gibco PHG0266). Further, a commercially available serum-free and feeder-free medium was prepared.

Deacetylated gellan gum (Nissan Chemical Industries Ltd.) was added at a concentration of 0.02% by weight to the human iPS medium without bFGF, the human iPS medium with bFGF, and the commercially available serum-free and feeder-free medium to prepare a human iPS gel medium without bFGF, a human iPS gel medium with bFGF, and a gel medium for comparison.

OCT3/4, SOX2, KLF4, and c-MYC were transferred to human fibroblasts using retrovirus. After floating culture for seven days, $1\times10^5$ cells were suspended in the human iPS gel medium without bFGF and cultured in the human iPS gel medium without bFGF, the human iPS gel medium with bFGF, or the gel medium for comparison. As a result, iPS cells were produced. The diagrams are shown in FIG. 27. Thus, the iPS cells produced in the human iPS gel medium without bFGF were reseeded over feeders. Two days later, their colonies were morphologically confirmed and consequently were, as shown in FIG. 28(*a*), undifferentiated iPS cell colonies. As a result of further staining the iPS cells with antibodies against OCT3/4 and NANOG, as shown in FIGS. 28(*b*) and 28(*c*), the iPS cells were positive therefor. These results demonstrated that iPS cells can be induced in a polymer medium.

Example 10: Clonality of iPS Cells Induced in Polymer Medium

300 μL of the CTK solution was added to a 6-cm dish containing the iPS cells induced in the polymer medium in the process of culture, and the dish was incubated for three minutes in a $CO_2$ incubator. Three minutes later, the dish was taken out of the incubator. After confirmation that only the feeder cells were detached from the dish, the CTK solution was removed using an aspirator. After the removal of the CTK solution, the iPS cells were washed by the addition of 500 μL of PBS to the dish, followed by the removal of PBS. 0.3 mL of a dissociation solution (Accumax) was added to the dish, which was then placed in a $CO_2$ incubator and incubated for five minutes. Then, 0.7 mL of the iPS medium without bFGF was added to the dish so that the iPS cells were suspended until becoming single cells.

After the suspension of the iPS cells, 4 mL of the iPS medium without bFGF was added to a centrifugal tube, and the iPS cell suspension was centrifuged at 270 g using a centrifuge. After the centrifugation, the supernatant was removed, and 1 mL of the iPS medium without bFGF was added thereto. The number of the cells was calculated using a hemocytometer. After the cell counting, $2.5\times10^5$ iPS cells were stained using Cell explorer live cell labeling kit Red and cell explorer live cell labeling kit Green (AAT BioQuest, Inc.). After the staining, the stained cells were mixed, and $5\times10^5$ iPS cells were seeded to a non-adherent dish or a 15-mL tube and subsequently floating-cultured without stirring. In the 15-mL tube, 2 mL of the human iPS gel medium without bFGF was used. In the non-adherent dish, 2 mL of the human iPS medium without bFGF and gellan gum was used. A ROCK inhibitor (Selleck Chemicals 51049) was added at a concentration of 10 μmol/L to each medium. Then, 500 μL of the human iPS medium without bFGF was added to the 15-mL tube and the non-adherent dish every day. The fresh human iPS gel medium without bFGF to be placed for the replacement contained the ROCK inhibitor at a concentration of 10 μmol/L. The ROCK inhibitor was added at a final concentration of 10 μmol/L to the 15-mL tube and the non-adherent dish every day, and the floating culture was continued for seven days.

As a result, as shown in FIG. 29(*a*), aggregation among distinctively stained iPS cell colonies was notably observed when the iPS cells were cultured using the medium without gellan gum in the non-adherent dish. As a result of quantification, 40% or more of the cells were aggregated. By contrast, as shown in FIG. 29(*b*), such aggregation was not observed when the iPS cells were cultured using the human iPS gel medium without bFGF in the 15-mL tube.

Example 11

After the suspension of iPS cells, 4 mL of the human iPS medium with bFGF was added to a 15-mL centrifugal tube, and the iPS cell suspension was centrifuged at 270 g using a centrifuge. After the centrifugation, the supernatant was removed, and 1 mL of the human iPS medium with bFGF was added to the 15-mL centrifugal tube. The number of the cells was calculated using a hemocytometer. After the cell counting, $5\times10^5$ iPS cells were seeded to 15-mL Falcon Tube® (Corning 352096) or a non-adherent dish and subsequently floating-cultured without stirring.

The medium used was 2 mL of the human iPS gel medium with bFGF or the human iPS medium with bFGF and without gellan gum, and the iPS cells were cultured in the tube or the non-adherent dish for five days to seven days. A ROCK inhibitor (Selleck Chemicals 51049) was added at 10 μmol/L to each medium. Then, 500 μL of the human iPS medium with bFGF and the gellan gum or the human iPS medium with bFGF and without gellan gum was added to the 15-mL tube and the non-adherent dish every day. The ROCK inhibitor was added at a final concentration of 10 μmol/L to the 15-mL tube and the non-adherent dish every day, and the floating culture was continued for five days to seven days.

FIG. 30(*a*) is a photograph showing the iPS cells cultured in the human iPS medium with bFGF and without gellan gum in the tube. In this case, the iPS cells were precipitated and were thus unable to be cultured. FIG. 30(*b*) is a photograph showing the iPS cells cultured in the human iPS medium with bFGF and the gellan gum in the tube. In this case, the iPS cells were neither precipitated nor aggregated. FIG. 30(c) is a photograph showing the iPS cells cultured in the human iPS medium with bFGF and without gellan gum in the dish. In this case, the iPS cells were aggregated and were thus unable to be cultured. FIG. 30(d) is a photograph showing the iPS cells cultured in the human iPS medium with bFGF and the gellan gum in the dish. In this case, the iPS cells were aggregated and were thus unable to be cultured.

Example 12

The same human iPS medium without bFGF and human iPS gel medium without bFGF as in Example 3 were prepared. Also, a commercially available serum-free and feeder-free medium was prepared.

Grating plates (Spheroid Generator MPs 500 and MPc 500, Kuraray Co., Ltd.) provided with a plurality of through-holes in a grid pattern having an upper opening diameter of 0.8 mm and a lower opening diameter of 0.5 mm, were prepared.

The CTK solution was added at 300 μL/well to a 6-well dish containing iPS cells in the process of culture on feeder cells, and the 6-well dish was incubated for three minutes in a $CO_2$ incubator. Three minutes later, the dish was taken out of the incubator. After confirmation that only the feeder cells were detached from the dish, the CTK solution was removed using an aspirator. After the removal of the CTK solution, the cells were washed by the addition of PBS at 500 μL/well to the dish, followed by the removal of PBS. Accumax was added at 0.3 mL/well to the dish, which was then placed in a $CO_2$ incubator and incubated for five minutes. Then, the human iPS medium without bFGF was added at 0.7 mL/well to the dish so that the iPS cells were suspended until becoming single cells.

Then, 4 mL of the human iPS medium without bFGF was added to a 15-mL centrifugal tube, and the iPS cell suspension was centrifuged at 270 g using a centrifuge. After the centrifugation, the supernatant was removed, and 1 mL of the human iPS medium without bFGF was added to the centrifugal tube. The number of the cells was calculated using a hemocytometer.

Then, $2.5 \times 10^5$ iPS cells were seeded to each grating plate and hanging drop-cultured for two days using each through-hole of the grating plate to form colonies having uniform sizes as shown in FIG. 31(a). Next, the colonies having uniform sizes were placed in 2 mL of the human iPS gel medium without bFGF, and the human iPS gel medium without bFGF containing the colonies was placed in a dialysis tube of a dialysis module. The dialysis module was further placed in a 50-mL centrifugal tube, and 20 mL of the commercially available serum-free and feeder-free medium without gellan gum was placed around the dialysis tube in the centrifugal tube. Then, 10 mL of the commercially available serum-free and feeder-free medium without gellan gum around the dialysis tube was replaced with a fresh medium every two days, and the floating culture was continued for seven days. The fresh medium to be placed for the replacement contained a ROCK inhibitor at a concentration of 10 μmol/L.

After the floating culture for seven days, as shown in FIGS. 31(b) and 32, increase in size of the iPS cell colonies was observed. These results demonstrated that iPS cells proliferate in their colonies.

The floating-cultured iPS cell colonies were further reseeded over feeder cells. Three days later, the maintenance of the undifferentiated states of the iPS cells was confirmed from the morphology of the colonies. As a result, as shown in FIGS. 33 and 34, all of the colonies were undifferentiated. These results demonstrated that the sizes of iPS cell colonies can be rendered uniform in a grating plate, and then, the iPS cells can be cultured in a polymer medium while maintaining their undifferentiated states.

Fifth Embodiment

The method for producing induced pluripotent stem (iPS) cells according to an embodiment of the present invention comprises: preparing somatic cells; and transferring RNAs encoding reprogramming factors into the somatic cells by a lipofection method.

The somatic cells are, for example, blood cells. The blood cells are separated from blood. The blood is, for example, peripheral blood or umbilical cord blood, though the blood is not limited thereto. The blood may be collected from an adult or may be collected from a minor. For the blood collection, an anticoagulant such as ethylenediamine tetraacetic acid (EDTA), heparin, or Acid Citrate Dextrose Formula A solution (ACD-A solution) is used.

The blood cells are, for example, nucleated cells such as monocytes, neutrophils, basophils, or lymphocytes and exclude erythrocytes, granulocytes, and platelets. The blood cells may be, for example, vascular endothelial progenitor cells, hematopoietic stem/progenitor cells, T cells, or B cells. The T cells are, for example, αβT cells.

The monocytes are separated from blood using a medium for blood cell separation and a centrifugal separation apparatus, etc. In the case of using Ficoll (GE Healthcare Japan Corp.) as the medium for blood cell separation, the method for separating the monocytes is as follows.

Monocyte separation accuracy tends to be deteriorated at a low temperature. Therefore, a centrifuge is set to 4° C. to 42° C., preferably 18° C. 10 μL to 50 mL of blood is collected from an adult or minor human, and a chelating agent containing EDTA is added to the blood so as not to clot the blood, followed by gentle mixing. A medium for human lymphocyte separation (Ficoll-Paque PREMIUM, GE Healthcare Japan Corp.) is dispensed at 5 mL/tube to two 15-mL tubes. 5 mL of PBS is added to 5 mL of the blood for dilution, and 5 mL of the diluted blood is layered on the medium for human lymphocyte separation in each tube. At this time, the diluted blood is slowly added onto the medium such that the blood runs down the wall of the tube so as not to disturb the interface.

The solution in each tube is centrifuged at 10×g to 1000×g, preferably 400×g, at 4° C. to 42° C., preferably 18° C., for five minutes to two hours, preferably 30 minutes. After the centrifugation, a white cloudy intermediate layer appears in the tube. This white cloudy intermediate layer contains monocytes. The white cloudy intermediate layer in the tube is gradually recovered with Pipetman and transferred to a new 15-mL tube. In this operation, it is necessary to avoid sucking out the lower layer. The white cloudy intermediate layer can be recovered in an amount of approximately 1 mL from one tube. The intermediate layers from the two tubes are transferred together to one tube.

1 mL to 48 mL, preferably 12 mL, of PBS is added to the recovered monocytes, and the solution is further centrifuged at 10×g to 1000×g, preferably 200×g, at 4° C. to 42° C., preferably 18° C., for one minute to 60 minutes, preferably ten minutes. Then, the supernatant of the solution is removed by aspiration using an aspirator, and the monocytes are suspended by the addition of 1 mL to 12 mL, preferably 3 mL, of a serum-free hematopoietic cell culture medium (X-VIVO® 10, Lonza Japan Ltd.) having known compositions to obtain a monocyte suspension. A 10 μL aliquot of the monocyte suspension is stained with Trypan Blue and counted using a hemocytometer.

In the case of using Vacutainer® (Becton, Dickinson and Company) as a blood collection tube, the method for separating the monocytes is as follows.

Monocyte separation accuracy tends to be deteriorated at a low temperature. Therefore, a centrifuge is set to 4° C. to 42° C., preferably 18° C. 8 mL of blood is collected from an adult or minor human using a blood collection tube (Vacutainer®, Becton, Dickinson and Company) and mixed with an anticoagulant by inversion. Then, the balance is adjusted, and the solution is centrifuged at 100×g to 3000×g, preferably 1500×g to 1800×g, at 4° C. to 42° C., preferably 18° C., for one minute to 60 minutes, preferably 20 minutes using a swing rotor. After the centrifugation, the upper layer, which is a plasma layer, is removed, and the monocyte layer and hemocytes sticking to the gel are suspended by pipetting to obtain a suspension. The obtained suspension is transferred to another 15-mL tube.

1 mL to 14 mL, preferably 12 mL, of PBS is added to the suspension in the 15-mL tube, and the suspension is centrifuged at 100×g to 3000×g, preferably 200×g, at 4° C. to 42° C., preferably 18° C., for one minute to 60 minutes, preferably five minutes. After the centrifugation, the supernatant is removed using an aspirator. A hematopoietic agent (PharmLyse®, ×10 concentrate, Becton, Dickinson and Company) is diluted to ×1 concentration with sterilized water. The pellets in the 15-mL tube are dissociated by tapping, and 1 mL to 14 mL, preferably 1 mL, of the hematopoietic agent is added thereto. Then, the solution is left standing at room temperature in the dark for one minute to 60 minutes, preferably one minute.

Next, 1 mL to 14 mL, preferably 12 mL, of PBS is added to the 15-mL tube, and the solution is centrifuged at 100×g to 3000×g, preferably 200×g, at 4° C. to 42° C., preferably room temperature, for one minute to 60 minutes, preferably five minutes. After the centrifugation, the supernatant is removed using an aspirator, and the monocytes are suspended by the addition of 1 mL to 15 mL, preferably 3 mL, of a serum-free hematopoietic cell culture medium (X-VIVO® 10, Lonza Japan Ltd.) having known compositions to obtain a monocyte suspension. A 10 μL aliquot of the monocyte suspension is stained with Trypan Blue and counted using a hemocytometer.

The method for separating the monocytes from blood is not limited to the methods described above, and, for example, the monocytes may be separated from blood using a dialysis membrane. Also, PurecellSelect System® for Whole Blood MNC Enrichment (Pall Corp.), a purifier for hemocyte removal (Cellsorba E®, Asahi Kasei Corp.), and a leukocyte removal filter made for platelet concentrates (Sepacell PL®, PLX-5B-SCD, Asahi Kasei Corp.), or the like can be used.

CTL-UP1 distributed from Cellular Technology Limited, PBMC-001 from Sanguine Biosciences, Inc., or the like may be used as the monocytes.

Alternatively, blood cells cryopreserved using a cell cryopreservation solution such as Cellbanker 1, Stem-Cellbanker GMP grade, or Stem-Cellbanker DMSO-free GMP grade (Nippon Zenyaku Kogyo Co., Ltd) may be thawed and used as the blood cells.

In order to thaw monocytes, first, 1 mL to 15 mL, preferably 8 mL, of a serum-free hematopoietic cell culture medium (X-VIVO® 10, Lonza Japan Ltd.) having known compositions is placed in advance in a 15-mL tube, and a tube containing frozen monocytes is placed in a warm bath of 4° C. to 42° C., preferably 37° C., to start the thawing of the monocytes. Then, the tube containing the monocytes with a small amount of ice still remaining is taken out of the warm bath, and the monocytes are transferred to the tube containing the serum-free hematopoietic cell culture medium having known compositions. A 10 μL aliquot of the monocyte suspension is stained with Trypan Blue and counted using a hemocytometer.

The blood cells may be separated on the basis of their cells surface markers. Hematopoietic stem/progenitor cells are positive for CD34. T cells are positive for any of CD3, CD4, and CD8. B cells are positive for any of CD10, CD19, and CD20. The hematopoietic stem/progenitor cells, the T cells, or the B cells are separated from blood cells using, for example, an automatic magnetic cell separation apparatus. Alternatively, monocytes separated in advance may be prepared. However, the reprogramming factor RNAs may be transferred to blood cells that have not been separated on the basis of cell surface markers.

CD34-positive cells are stem/progenitor cells and tend to be reprogrammed. When iPS cells are produced using T cells, which are CD3-positive cells, the iPS cells derived from the T cells retain a TCR recombination system and therefore tend to be efficiently induced to differentiate into T cells.

The method for separating the CD34-positive cells is as follows.

10 μL of IL-6 (100 μg/mL), 10 μL of SCF (300 μg/mL), 10 μL of TPO (300 μg/mL), 10 μL of Flt3 ligand (300 μg/mL), and 10 μL of IL-3 (10 μg/mL) are added to 10 mL of a serum-free medium (StemSpan H3000, STEMCELL Technologies Inc.) to prepare a hemocyte culture medium (hematopoietic stem/progenitor cell culture medium).

1 mL to 6 mL, preferably 2 mL, of the hemocyte culture medium is placed in one well of a 6-well plate. In order to prevent the evaporation of the medium, 1 mL to 6 mL, preferably 2 mL, of PBS is placed in each of the remaining five wells. Then, the 6-well plate is placed in an incubator of 4° C. to 42° C., preferably 37° C., and incubated.

A column buffer containing 10 μL to 1 mL, preferably 80 μL, of EDTA (500 mmol/L) and 10 μL to 1 mL, preferably 200 μL, or FBS added to 20 mL of PBS is prepared. A monocyte suspension containing $1\times10^4$ to $1\times10^9$, preferably $2\times10^7$ monocytes is dispensed to 15-mL tubes, and the monocyte suspension is centrifuged at 100×g to 3000×g, preferably 300×g, at 4° C. to 42° C., preferably 4° C., for ten minutes. After the centrifugation, the supernatant is removed, and the monocytes are suspended in 100 μL to 1 mL, preferably 300 μL, of the column buffer.

10 μL to 1 mL, preferably 100 μL, of FcR Blocking Reagent (Miltenyi Biotec K.K.) and 10 μL to 1 mL, preferably 100 μL, of CD34 MicroBead Kit (Miltenyi Biotec K.K.) are added to the monocyte suspension in the 15-mL tube. The FcR Blocking Reagent is used for enhancing the specificity of MicroBead labeling. Then, the monocyte suspension is mixed and left standing at 4° C. to 42° C., preferably 4° C., for one minute to two hours, preferably 30 minutes.

Next, the monocyte suspension in the 15-mL tube is diluted by the addition of 1 mL to 15 mL, preferably 10 mL, of the column buffer and centrifuged at 100×g to 1000×g, preferably 300×g, at 4° C. to 42° C., preferably 4° C., for one minute to two hours, preferably ten minutes. After the centrifugation, the supernatant in the 15-mL tube is removed using an aspirator, and the monocytes are resuspended by the addition of 10 μL to 10 mL, preferably 500 μL, of the column buffer.

A column for automatic magnetic cell separation apparatuses (MS column, Miltenyi Biotec K.K.) is attached to an automatic magnetic cell separation apparatus (MiniMACS Separation Unit, Miltenyi Biotec K.K.), and the column is washed by the addition of 10 μL to 10 mL, preferably 500 μL, of the column buffer. Next, the monocytes are placed in the column. 10 μL to 10 mL, preferably 500 μL, of the column buffer is further placed in the column, and the column is washed once to ten times, preferably three times. Then, the column is detached from the automatic magnetic cell separation apparatus and placed in a 15-mL tube. Next, 10 μL to 10 mL, preferably 1000 μL, of the column buffer is placed in the column, and a syringe is immediately pushed to elute CD34-positive cells into the 15-mL tube.

10 μL of the CD34-positive cell suspension is stained with Trypan Blue, and the number of the cells is counted using a hemocytometer. The CD34-positive cell suspension in the 15-mL tube is centrifuged at 100×g to 1000×g, preferably 300×g, at 4° C. to 42° C., preferably 4° C., for one minute to two hours, preferably ten minutes. After the centrifugation, the supernatant is removed using an aspirator. Further, the CD34-positive cells are resuspended in the hemocyte culture medium warmed in advance, and the CD34-positive cells are seeded over a culture plate. Then, the CD34-positive cells are cultured at 4° C. to 42° C., preferably 37° C., in a 1% to 20%, preferably 5% $CO_2$ environment for six days. During this culture, medium replacement may be unnecessary.

The method for isolating cells on the basis of a marker other than CD34 is the same as the method for isolating the CD34-positive cells.

The blood cells to which the reprogramming factor RNAs are to be transferred are cultured in, for example, a T cell culture medium or a hematopoietic stem/progenitor cell culture medium. In the case of producing T cell-derived iPS cells, the T cell culture medium is used. In the case of producing iPS cells from CD34-positive cells, the hematopoietic stem/progenitor cell culture medium is used. The culture conditions involve, for example, a $CO_2$ concentration of 5%, an oxygen concentration of 25% or lower, and a temperature of 37° C. or lower.

The blood cells to which the reprogramming factor RNAs are to be transferred are cultured in a feeder-free manner using a basement membrane matrix such as Matrigel (Corning Inc.), CELLstart® (Thermo Fisher Scientific, Inc.), or Laminin 511 (Nippi, Inc.).

A culture solution such as Primate ES Cell Medium, Reprostem, ReproFF, ReproFF2, ReproXF (ReproCELL Inc.), mTeSR1, TeSR2, TeSRE8, ReproTeSR (STEMCELL Technologies Inc.), PluriSTEM® Human ES/iPS Medium (Merck KGaA), NutriStem® XF/FF Culture Medium for Human iPS and ES Cells, Pluriton reprogramming medium (Stemgent Inc.), PluriSTEM®, StemFit AK02N, StemFit AK03 (Ajinomoto Co., Inc.), ESC-Sure® serum and feeder free medium for hESC/iPS (Applied StemCell, Inc.), and L7® hPSC Culture System (Lonza Japan Ltd.) may be used.

For floating culture, the blood cells are placed in a spinner flask and cultured with stirring. Alternatively, the blood cells may be placed in a 0.001% to 10% gellan gum solution, at least one polymer compound selected from the group consisting of deacetylated gellan gum, hyaluronic acid, rhamsan gum, diutan gum, xanthan gum, carrageenan, fucoidan, pectin, pectic acid, pectinic acid, heparan sulfate, heparin, heparitin sulfate, keratosulfate, chondroitin sulfate, dermatan sulfate, rhamnan sulfate, and salts thereof, or a temperature-sensitive gel and cultured. The gel medium may contain methylcellulose. Methylcellulose contained therein suppresses the aggregation among the cells.

The temperature-sensitive gel may contain at least one member selected from poly(glycerol monomethacrylate) (PGMA), poly(2-hydroxypropyl methacrylate) (PHPMA), polyisopropylacrylamide, poly(N-isopropylacrylamide) (PNIPAM), amine terminated, carboxylic acid terminated, maleimide terminated, N-hydroxysuccinimide (NHS) ester terminated, triethoxysilane terminated, poly(N-isopropylacrylamide-co-acrylamide), poly(N-isopropylacrylamide-co-acrylic acid), poly(N-isopropylacrylamide-co-butylacrylate), poly(N-isopropylacrylamide-co-methacrylic acid), poly(N-isopropylacrylamide-co-methacrylic acid-co-octadecyl acrylate), and N-isopropylacrylamide.

The medium may contain at least one substance selected from the group consisting of cadherin, laminin, fibronectin, and vitronectin.

The reprogramming factor RNAs are transferred to the blood cells. The reprogramming factor RNAs comprise, for example, Oct3/4 mRNA, Sox2 mRNA, Klf4 mRNA, and c-Myc mRNA. The reprogramming factor RNAs may further comprise an mRNA of at least one factor selected from the group consisting of LIN28A, LIN28B, GLIS1, FOXH1, p53-dominant negative, p53-P275S, L-MYC, NANOG, DPPA2, DPPA4, DPPA5, ZIC3, BCL-2, E-RAS, TPT1, SALL2, NAC1, DAX1, TERT, ZNF206, FOXD3, REX1, UTF1, KLF2, KLF5, ESRRB, miR-291-3p, miR-294, miR-295, NR5A1, NR5A2, TBX3, MBD3sh, TH2A, and TH2B. These mRNAs are available from TriLink BioTechnologies, Inc.

Each mRNA may be modified with at least one member selected from the group consisting of pseudouridine (Ψ), 5-methyluridine (5meU), N1-methylpseudouridine (me1Ψ), 5-methoxyuridine (5moU), 5-hydroxymethyluridine (5hmU), 5-formyluridine (5fU), 5-carboxymethyl ester uridine (5camU), thienoguanosine (thG), N4-methylcytidine (me4C), 5-methylcytidine (m5C), 5-methoxycytidine (5moC), 5-hydroxymethylcytidine (5hmC), 5-hydroxycytidine (5hoC), 5-formylcytidine (5fC), 5-carboxycytidine (5caC), N6-methyl-2-aminoadenosine (m6DAP), diaminopurine (DAP), 5-methyluridine (m5U), 2'-O-methyluridine (Um or m2'-OU), 2-thiouridine (s2U), and N6-methyladenosine (m6A).

The mRNA may be polyadenylated.

The mRNA may be prepared by the polyadenylation of an in vitro transcribed (IVT) RNA. The mRNA may be polyadenylated during IVT by using a DNA template encoding poly(A) tail. The mRNA may be capped. For maximizing the efficiency of expression in cells, it is preferred that a great majority of mRNA molecules should contain caps. The mRNA may have a 5'cap[m7G(5')ppp(5')G] structure. This sequence stabilizes mRNA and promotes mRNA transcription. From an mRNA having 5' triphosphate, the 5' triphosphate may be removed by dephosphorylation treatment. The mRNA may have [3'O-Me-m7G(5')ppp(5')G] as an anti-reverse cap analog (ARCA). ARCA is a sequence that is inserted upstream of a transcription start point and doubles the efficiency of mRNA transcription. The mRNA may have poly(A) tail.

The mRNA may be a replicative RNA having the ability to self-propagate. The replicative RNA is an RNA having the ability to self-propagate and, unlike usual RNA, also has the ability to express proteins necessary for RNA replication.

The replicative RNA is derived from Venezuelan equine encephalitis (VEE) viruses, which are Alphaviruses. Upon lipofection of cells with the replicative RNA, RNA continuously yielding reprogramming factors can be expressed in the cells. Therefore, it is possible to eliminate the need of adding RNA every day.

The sequence of the replicative RNA may comprise a sequence obtained from Alphavirus replicon RNA or Alphavirus selected from the group consisting of eastern equine encephalitis (EEE) virus, Venezuelan equine encephalitis (VEE) virus, Everglades virus, Mucambo virus, Pixuna virus, and western equine encephalitis (WEE) virus.

The replicative RNA may also comprise a sequence obtained from Alphavirus selected from the group consisting of Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, and Buggy Creek virus.

The replicative RNA contains (VEE RNA replicase)-(promoter)-(RF1)-(self-cleavable peptide)-(RF2)-(self-cleavable peptide)-(RF3)-(IRES or core promoter)-(RF4)-(IRES or any promoter)-(any selectable marker)-(VEE 3'UTR and poly(A) tail)-(any selectable marker)-promoter in the direction of 5'→3'. The RF1-4 is a factor that induces the dedifferentiation of somatic cells into pluripotent cells. The RF2-3, the RF3-4, and the RF4 are arbitrarily selected. The RF1 to RF4 may be selected from the group consisting of Oct-4, Klf4, Sox-2, c-Myc, LIN28A, LIN28B, GLIS1, FOXH1, p53-dominant negative, p53-P275S, L-MYC, NANOG, DPPA2, DPPA4, DPPA5, ZIC3, BCL-2, E-RAS, TPT1, SALL2, NAC1, DAX1, TERT, ZNF206, FOXD3, REX1, UTF1, KLF2, KLF5, ESRRB, miR-291-3p, miR-294, miR-295, NR5A1, NR5A2, TBX3, MBD3sh, TH2A, and TH2B.

The reprogramming factor RNAs are transferred into the blood cells by, for example, a lipofection method. The lipofection method is a method which involves forming a complex of nucleic acids (negatively charged substances) and positively charged lipids through electrical interaction, and taking up the complex into cells by endocytosis or membrane fusion. The lipofection method has advantages such as little damage on cells, excellent transfer efficiency, convenient operation, and a short duration.

For example, a short interfering RNA (siRNA) or a lipofection reagent is used in the lipofection with the reprogramming factor RNAs. An siRNA lipofection reagent and an mRNA lipofection reagent can be used as the RNA lipofection reagent. More specifically, for example, Lipofectamine® RNAiMAX (Thermo Fisher Scientific, Inc.), Lipofectamine® MessengerMAX (Thermo Fisher Scientific, Inc.), Lipofectamine® 2000, Lipofectamine® 3000, Neon Transfection System (Thermo Fisher Scientific, Inc.), Stemfect RNA transfection reagent (STEMGENT), Next-Fect® RNA Transfection Reagent (Bioo Scientific Corp.), Amaxa® Human T cell Nucleofector® kit (Lonza Japan Ltd., VAPA-1002), Amaxa® Human CD34 cell Nucleofector® kit (Lonza Japan Ltd., VAPA-1003), and ReproRNA® transfection reagent (STEMCELL Technologies Inc.) can be used as the RNA lipofection reagent.

The number of the blood cells for the lipofection with the reprogramming factor RNAs is, for example, 1 to $1 \times 10^8$ cells, $1 \times 10^4$ cells to $5 \times 10^6$ cells, or $5 \times 10^5$ cells to $5 \times 10^6$ cells. The amounts of the reprogramming factor RNAs for the lipofection per mL of a culture solution are, for example, 5 ng to 50 µg, 50 ng to 10 µg, or 600 ng to 3 µg per run. The amount of the lipofection reagent for the lipofection is, for example, 0.1 µL to 500 µL, 1 µL to 100 µL, or 1 µL to 40 µL per run. The lipofection with the reprogramming factors is performed for 0.1 hours or longer and 24 hours or shorter, two hours or longer and 21 hours or shorter, 12 hours and 30 minutes or longer and 18 hours and 30 minutes or shorter, or 18 hours per run. For example, when a 12-well plate is used and the number of the cells is $4 \times 10^5$, 6 µL of RNAiMAX or 3 µL of MessengerMAX is used.

The lipofection for reprogramming is repetitively performed, for example, once two days or once a day or for five days or longer and nine days or shorter, six days or longer and eight days or shorter, or seven days. However, when the mRNA is a replicative RNA, the lipofection may be performed once. The medium used in the lipofection with the reprogramming factor RNAs is, for example, a low-serum medium such as Opti-MEM® (Gibco).

Whether or not induced pluripotent stem cells are induced from the blood cells or whether or not the blood cells are reprogrammed into induced pluripotent stem cells is confirmed, for example, by analyzing whether or not to be positive for at least one surface marker selected from TRA-1-60, TRA-1-81, SSEA-1, and SSEA5, which are cell surface markers exhibiting undifferentiation, using a flow cytometer. TRA-1-60 is an antigen specific for iPS/ES cells and is not detected in somatic cells. Since iPS cells can be obtained from only a TRA-1-60-positive fraction, TRA-1-60-positive cells are considered as a species of iPS cells.

In the method for producing induced pluripotent stem cells according to the embodiment of the present invention described above, the induced pluripotent stem cells are produced by transferring RNA that permits expression of reprogramming factors into the somatic cells e.g., blood cells, and expressing the reprogramming factors. Therefore, it is possible to produce the induced pluripotent stem cells without the integration of the reprogramming factors into the DNA of the somatic cells.

In a conventional method for producing induced pluripotent stem cells, the reprogramming factors are inserted into somatic cell DNA. This damages the genome and triggers oncogenesis of the cells. By contrast, in the method for producing induced pluripotent stem cells according to the embodiment of the present invention, it is possible to produce induced pluripotent stem cells without the insertion of the genes into the genome and without the possibility of associated tumorigenesis, because RNA encoding the reprogramming factors is employed. Therefore, the induced pluripotent stem cells produced by the production method according to the embodiment of the present invention makes it possible to satisfy the good manufacturing practice of clinically available cells.

In conventional methods for producing induced pluripotent stem cells using retroviruses or lentiviruses, the viruses remain in the produced induced pluripotent stem cells. By contrast, in the method for producing induced pluripotent stem cells according to the embodiment of the present invention, no virus is required because the reprogramming factor RNAs are transferred by lipofection. Therefore, no virus remains in the produced induced pluripotent stem cells. In this regard as well, the induced pluripotent stem cells produced by the production method according to the embodiment of the present invention makes it possible to satisfy the good manufacturing practice of clinically available cells.

A conventional method for producing induced pluripotent stem cells using electroporation largely damages cells and destroys a large number of cells before induction. By contrast, the lipofection used in the method for producing induced pluripotent stem cells according to the embodiment of the present invention has little damage on cells and does not destroy a large number of cells before induction. Furthermore, the lipofection does not require expensive equipment and is performed by a convenient process.

For producing induced pluripotent stem cells from fibroblasts, it is necessary to collect skin cells by highly invasive biopsy. By contrast, the method for producing induced pluripotent stem cells according to the embodiment of the present invention makes it possible to collect blood cells by low invasive blood collection. In general, a sufficient number of blood cells necessary for the production of induced pluripotent stem cells can be obtained from blood collection. Therefore, unlike fibroblasts, blood cells do not have to proliferate before induction of induced pluripotent stem cells. In addition, blood cells are free from the risk of DNA injury that may occur during culture for the proliferation. Moreover, unlike skin cells, blood cells can be collected without being aired out. Therefore, induced pluripotent stem cells can be induced from the blood cells in a clean sealed system from the stage of blood collection. In this regard as well, the blood cells are suitable for clinical utilization.

Example 13

(Preparation)

Human blood cells were obtained from a healthy adult human male. Also, modified mRNAs (TriLink BioTechnologies, Inc.), a non-adherent dish, a 15-mL tube, a 50-mL tube, Ficoll, a flow cytometer (Becton, Dickinson and Company), an antibody against CD34 (Miltenyi Biotec K.K.), an antibody against CD3 (Miltenyi Biotec K.K.), MACS® buffer (Miltenyi Biotec K.K.), a T cell culture medium, a low-serum medium (Opti-MEM®, Gibco), an siRNA transfer reagent (Lipofectamine® RNAiMAX, Thermo Fisher Science, Inc.), and an antibody against TRA-1-60 (Becton, Dickinson and Company) were prepared.

The T cell (CD3-positive cell) culture medium was a mixed solution of the following A medium and B medium. The A medium was a mixed solution of 15 mL of X vivo-10 (Lonza Japan Ltd., 04-743Q) and IL-2 (10 µg/mL). The B medium was prepared by mixing X vivo-10 and 50 µL of Dynabeads CD3/CD28 (Life Technologies Corp., 111-31D) into a 1.5-mL tube, vortexing the tube for five seconds, then spinning down the tube, leaving the tube standing on DynaMag-2 (Thermo Fisher Science, Inc.), and after the 1-minute standing, removing the supernatant.

10 µL of IL-6 (100 µg/mL), 10 µL of SCF (300 µg/mL), 10 µL of TPO (300 µg/mL), 10 µL of Flt3 ligand (300 µg/mL), and 10 µL of IL-3 (10 µg/mL) were added to 10 mL of a serum-free medium (StemSpan H3000, STEMCELL Technologies Inc.) to prepare a hemocyte culture medium (hematopoietic stem/progenitor cell culture medium).

Further, an OCT3/4 mRNA-containing solution, a SOX2 mRNA-containing solution, a KLF4 mRNA-containing solution, a c-MYC mRNA-containing solution, a LIN28A mRNA-containing solution, and a green fluorescence protein (GFP) mRNA-containing solution were prepared to have their respective concentrations of 100 ng/µL. Next, 385 µL of the OCT3/4 mRNA-containing solution, 119 µL of the SOX2 mRNA-containing solution, 156 µL of the KLF4 mRNA-containing solution, 148 µL of the c-MYC mRNA-containing solution, 83 µL of the LIN28A mRNA-containing solution, and 110 µL of the GFP mRNA-containing solution were mixed to obtain a reprogramming factor mixed solution. The obtained reprogramming factor mixed solution was dispensed at 50 µL/tube to 1.5-mL RNase-Free tubes (Eppendorf® tubes, Eppendorf AG) and stored in a freezer of −80° C.

(Preparation of Monocytes)

A centrifuge was set to 18° C. 5 mL to 50 mL of blood was collected, and EDTA was added to the blood, followed by gentle mixing. A medium for human lymphocyte separation (Ficoll-Paque PREMIUM, GE Healthcare Japan Corp.) was dispensed at 5 mL/tube to two 15-mL tubes. 5 mL of PBS was added to the blood for dilution, and 5 mL of the diluted blood was layered on the medium for human lymphocyte separation in each tube. At this time, the diluted blood was slowly added onto the medium such that the blood ran down the wall of the tube so as not to disturb the interface.

The solution in the tube was centrifuged at 400×g at 18° C. for 30 minutes. In this operation, both acceleration and deceleration were slowly performed. After the centrifugation, a white cloudy intermediate layer appeared in the tube. This white cloudy intermediate layer contained monocytes. The white cloudy intermediate layer in the tube was gradually recovered with Pipetman and transferred to a new 15-mL tube. In this operation, attention was paid to avoid sucking out the lower layer. The white cloudy intermediate layer could be recovered in an amount of approximately 1 mL from one tube. The intermediate layers from the two tubes were transferred together to one tube.

12 mL of PBS was added to the recovered monocytes, and the solution was further centrifuged at 200×g at 18° C. for ten minutes. Then, the supernatant of the solution was removed by aspiration using an aspirator, and the monocytes were suspended by the addition of 3 mL of a serum-free hematopoietic cell culture medium (X-VIVO® 10, Lonza Japan Ltd.) having known compositions to obtain a monocyte suspension. A 10 µL aliquot of the monocyte suspension was stained with Trypan Blue and counted using a hemocytometer.

(Separation of CD34- or CD3-Positive Cells)

$1 \times 10^7$ monocytes were made to react with the antibodies against CD34 or the antibodies against CD3 in 100 µL of a solution of 4° C. for 15 minutes. After the reaction, 5 mL of MACS® buffer (Miltenyi Biotec K.K.) was added to the solution, and the mixture was centrifuged at 270 g. After the centrifugation, the supernatant was removed, and 1 mL of MACS buffer was added to the cells. Then, CD34-positive cells or CD3-positive cells among the monocytes were separated by using the separation program of an automatic magnetic cell separation apparatus (autoMACS, Miltenyi Biotec K.K.).

(Culture of Separated Cells)

$5 \times 10^6$ separated monocytes were suspended in 1 mL of the T cell culture medium or the hematopoietic stem/progenitor cell culture medium, seeded to a 12-well plate, and cultured. The culture conditions involved a $CO_2$ concentration of 5%, an oxygen concentration of 19%, and a temperature of 37° C.

(Lipofection with Reprogramming Factors)

100 µL of a low-serum medium (Opti-MEM®, Gibco) and 25 µL of the reprogramming factor mixed solution were mixed to prepare a first mixed solution. Also, 112.5 µL of a low-serum medium (Opti-MEM®, Gibco) and 12.5 µL of an siRNA transfer reagent (Lipofectamine® RNAiMAX, Thermo Fisher Science, Inc.) were mixed to prepare a second mixed solution. Then, the first mixed solution and the second mixed solution were mixed and left standing at room temperature for 15 minutes to prepare a lipofection reaction solution.

The obtained lipofection reaction solution was gently added at 60 μL/well to the 12-well plate containing the monocytes in the process of culture, and the monocytes were subsequently cultured in a feeder-free manner at 37° C. for 18 hours. The culture conditions involved a $CO_2$ concentration of 5%, an oxygen concentration of 19%, and a temperature of 37° C. The density of the monocytes was $3\times10^6$ cells when the lipofection reaction solution was added. 18 hours later, the monocytes were recovered into a 15-mL tube and centrifuged at 300 g, followed by the removal of the supernatant. Then, 1.25 mL of the hemocyte culture medium for CD34 was added to the 15-mL tube. The monocyte suspension was brought back to the same 12-well plate as above. The monocytes were cultured overnight in a feeder-free manner at 37° C. The culture conditions involved a $CO_2$ concentration of 5% and an oxygen concentration of 19%. These steps were repeated every two days for seven days.

(Confirmation of GFP Expression)

At day 7 after the start of lipofection, the density of the cells lipofected a total of four times was $3\times10^6$ cells. An aliquot of the cells was taken out of the 12-well plate, and the expression of GFP was confirmed under a fluorescence microscope. As a result, as shown in FIG. 35, the expression of GFP was confirmed. From these results, the proteins were confirmed to be synthesized from the mRNA harbored by the monocytes transfected with the mRNA.

(Confirmation of TRA-1-60 Expression)

At day 7 after the start of lipofection, an aliquot of the cells was taken out of the 12-well plate, and the cells thus taken out were stained with an allophycocyanin (APC) fluorescent dye-labeled antibody against TRA-1-60 (surface antigen that is specifically expressed on cells in which reprogramming has been initiated). Then, the percentage of TRA-1-60-positive cells was confirmed using a fluorescence-activated cell sorter (FACS®, Becton, Dickinson and Company) to confirm that the reprogramming was started in the cells so that iPS cell genes were expressed to generate iPS cells.

As shown in FIG. 36, a dot plot was prepared with autofluorescence intensity on the x-axis against the fluorescence intensity of the fluorescently labeled anti-TRA-1-60 antibody on the y-axis. The TRA-1-60-positive cells were not detected in a negative control that did not harbor the genes. By contrast, the TRA-1-60-positive cells were detected in Experiments 1, 2, and 3. Experiment 1 depicts the results of inducing iPS cells from the whole of the monocytes that were not separated on the basis of a marker. Experiment 2 depicts the results of inducing iPS cells from the CD3-positive separated cells. Experiment 3 depicts the result of inducing iPS cells from the CD34-positive separated cells. These results demonstrated that it is possible to transfer the reprogramming factors into blood-derived cells by using lipofection with the reprogramming factor RNAs to induce iPS cells.

Sixth Embodiment

The method for producing somatic cells from animal cells according to an embodiment of the present invention comprises: preparing animal cells; and transferring an inducer ribonucleic acid (RNA) into the animal cells by lipofection to differentiate the animal cells into somatic cells.

The animal cells include stem cells. Both induced pluripotent stem cells (iPS cells) and embryonic stem cells (ES cells) can be used as the stem cells. The animal cells may be human fibroblasts or human blood cells.

A culture solution such as Primate ES Cell Medium, mTeSR1, TeSR2, or TeSRE8 (STEMCELL Technologies Inc.) may be used for culturing the stem cells.

The medium for culturing the stem cells may contain a gel. The gel may contain at least one polymer compound selected from the group consisting of deacylated gellan gum, gellan gum, hyaluronic acid, rhamsan gum, diutan gum, xanthan gum, carrageenan, fucoidan, pectin, pectic acid, pectinic acid, heparan sulfate, heparin, heparitin sulfate, keratosulfate, chondroitin sulfate, dermatan sulfate, rhamnan sulfate, and salts thereof. The gel medium may contain methylcellulose. Methylcellulose contained therein suppresses the aggregation among the cells.

The gel may be a temperature-sensitive gel. The temperature-sensitive gel may be at least one member selected from poly(glycerol monomethacrylate) (PGMA), poly(2-hydroxypropyl methacrylate) (PHPMA), poly(N-isopropylacrylamide) (PNIPAM), amine terminated, carboxylic acid terminated, maleimide terminated, N-hydroxysuccinimide (NHS) ester terminated, triethoxysilane terminated, poly(N-isopropylacrylamide-co-acrylamide), poly(N-isopropylacrylamide-co-acrylic acid), poly(N-isopropylacrylamide-co-butylacrylate), poly(N-isopropylacrylamide-co-methacrylic acid), poly(N-isopropylacrylamide-co-methacrylic acid-co-octadecyl acrylate), and N-isopropylacrylamide.

The medium for culturing the stem cells may contain at least one substance selected from the group consisting of cadherin, laminin, fibronectin, and vitronectin.

The somatic cells produced from the animal cells are, for example, neuronal cells, though the somatic cells are not limited thereto. For example, somatic cells such as myocardial cells, hepatic cells, retinal cells, corneal cells, and blood cells may be produced. In the case of producing neuronal cells, the inducer RNA to be transferred into the animal cells comprises, for example, neurogenin 2 (Ngn2) mRNA. The Ngn2 is a switch protein necessary for differentiation into neuronal cells. The inducer RNA may comprise an mRNA corresponding to a drug resistance gene. The drug is, for example, an antibiotic such as puromycin, neomycin, blasticidin, G418, hygromycin, or Zeocin. The cells harboring the inducer RNA exhibit the drug resistance.

Each mRNA comprised in the inducer RNA may be modified with at least one member selected from the group consisting of pseudouridine (Ψ), 5-methyluridine (5meU), N1-methylpseudouridine (me1Ψ), 5-methoxyuridine (5moU), 5-hydroxymethyluridine (5hmU), 5-formyluridine (5fU), 5-carboxymethyl ester uridine (5camU), thienoguanosine (thG), N4-methylcytidine (me4C), 5-methylcytidine (m5C), 5-methoxycytidine (5moC), 5-hydroxymethylcytidine (5hmC), 5-hydroxycytidine (5hoC), 5-formylcytidine (5fC), 5-carboxycytidine (5caC), N6-methyl-2-aminoadenosine (m6DAP), diaminopurine (DAP), 5-methyluridine (m5U), 2T-O-methyluridine (Um or m2'-OU), 2-thiouridine (s2U), and N6-methyladenosine (m6A).

The mRNA may polyadenylated. The mRNA may be prepared by the polyadenylation of an in vitro transcribed (IVT) RNA. The mRNA may be polyadenylated during IVT by using a DNA template encoding poly(A) tail. The mRNA may be capped. For maximizing the efficiency of expression in cells, a great majority of mRNA molecules may contain caps.

The mRNA may have a 5'cap[m7G(5')ppp(5')G] structure. This sequence stabilizes mRNA and promotes mRNA transcription. From an mRNA having 5' triphosphate, the 5' triphosphate may be removed by dephosphorylation treatment. The mRNA may have [3'O-Me-m7G(5')ppp(5')G] as an anti-reverse cap analog (ARCA). ARCA is a sequence that is inserted upstream of a transcription start point and doubles the efficiency of mRNA transcription. The mRNA may have poly(A) tail.

The inducer RNA comprises, for example, Ngn2-T2A-Puro mRNA (TriLink BioTechnologies, Inc., an RNA corresponding to the DNA described in SEQ ID NO: 1). Cells transfected with Ngn2-T2A-Puro mRNA (TriLink BioTechnologies, Inc.) produce neurogenin 2 (Ngn2) and also exhibit puromycin resistance. The mRNA may be capped with an anti-reverse cap analog (ARCA), polyadenylated, and substituted with 5-methylcytidine and pseudouridine. The 5-methylcytidine and the pseudouridine reduce the ability of an antibody to recognize mRNA. An RNA corresponding to the DNA described in SEQ ID NO: 2 may be used. The DNA described in SEQ ID NO: 2 is derived from the DNA of SEQ ID NO: 1 by the removal of an xba1 restriction site.

The inducer RNA is transferred into the animal cells by a lipofection method. The lipofection method is a method which involves forming a complex of nucleic acids (negatively charged substances) and positively charged lipids through electrical interaction, and taking up the complex into cells by endocytosis or membrane fusion. The lipofection method has advantages such as little damage on cells, excellent transfer efficiency, convenient operation, and a short duration.

For example, Lipofectamine MessengerMAX® is used as a lipofection reagent in the lipofection with the inducer RNA. Alternatively, for example, Lipofectamine® RNAiMAX (Thermo Fisher Scientific, Inc.), Lipofectamine® 2000, Lipofectamine® 3000, Neon Transfection System (Thermo Fisher Scientific, Inc.), Stemfect RNA transfection reagent (STEMGENT), NextFect® RNA Transfection Reagent (Bioo Scientific Corp.), Amaxa® Human T cell Nucleofector® kit (Lonza Japan Ltd., VAPA-1002), Amaxa® Human CD34 cell Nucleofector® kit (Lonza Japan Ltd., VAPA-1003), and ReproRNA® transfection reagent (STEMCELL Technologies Inc.) may be used as a lipofection reagent.

In the case of using, for example, a 12-well plate, the number of the cells for the lipofection with the inducer RNA is $1\times10^4$ to $1\times10^8$, $5\times10^4$ to $1\times10^6$, or $1\times10^5$ to $5\times10^5$ per well. The area of the bottom of one well is 4 $cm^2$. The amount of the inducer RNA for the lipofection with the inducer RNA is 200 ng to 5000 ng, 400 ng to 2000 ng, or 500 ng to 1000 ng per run. The amount of the lipofection reagent for the lipofection with the inducer RNA is 0.1 µL to 100 µL, 1 µL to 50 µL, or 1.5 µL to 10 µL.

The medium used for the lipofection with the inducer RNA is, for example, a low-serum medium such as Opti-MEM® (Gibco). The medium for use in the lipofection with the inducer RNA and before or after this lipofection may contain B18R protein. The B18R protein mitigates the innate antiviral response of cells. The B18R protein may be used for suppressing cell death resulting from immune response associated with RNA insertion into cells. However, since the method for producing somatic cells from animal cells according to this embodiment differentiates the animal cells into somatic cells in a short period, the medium may not contain the B18R protein or may contain the B18R protein at a dilute concentration of 0.01% to 1%.

The animal cells are differentiated into the somatic cells within ten days, nine days, eight days, or seven days from the lipofection with the inducer RNA. When the somatic cells to be produced are neuronal, whether or not they are differentiated into the neuronal cells is confirmed on the basis of whether or not they are positive for Ngn2, β-III Tubulin, MAP2, PsA-NCAM, or vGlu. Ngn2 is a switch protein necessary for differentiation into neuronal cells. The β-III Tubulin, the MAP2, the PsA-NCAM, and the vGlu are markers labeling neuronal cells and are constituent proteins of microtubules in neurites.

When the inducer RNA comprises an mRNA corresponding to a drug resistance gene, cells that exhibit the drug resistance may be selected after the lipofection. When the inducer RNA comprises, for example, an mRNA corresponding to puromycin resistance gene, cells other than cells harboring the inducer RNA can be destroyed by the exposure of the lipofected cells to puromycin to select the cells harboring the inducer RNA. The inducer RNA may comprise an mRNA corresponding to a gene of any antibiotic selected from neomycin, blasticidin, G418, hygromycin, Zeocin, and the like as the mRNA corresponding to a drug resistance gene.

The method for producing somatic cells from animal cells according to the embodiment of the present invention described above makes it possible to efficiently produce somatic cells such as neuronal cells without damaging genes of the animal cells including iPS/ES cells and the like by expressing RNA encoding particular genes in animal cells including iPS/ES cells and the like.

A method for producing somatic cells from iPS/ES cells and the like using hormones or chemical substances requires a very long time for producing the somatic cells. By contrast, the method for producing somatic cells from animal cells according to the embodiment of the present invention makes it possible to produce somatic cells in a very short time.

In a method for producing somatic cells from animal cells including iPS/ES cells and the like using hormones or chemical substances, only some of the animal cells including iPS/ES cells and the like are converted to the somatic cells of interest. By contrast, the method for producing somatic cells from animal cells according to the embodiment of the present invention converts 90% or more of the cells to the somatic cells of interest by RNA transfer.

In a method for producing somatic cells from iPS/ES cells and the like using hormones or chemical substances, even if the same protocol is used, it results in variations among clones in such a way that some clones become the somatic cells of interest and others do not. By contrast, the method for producing somatic cells from animal cells according to the embodiment of the present invention makes it possible to yield high efficiency of induced differentiation for a plurality of clones.

In the case of producing cells for transplantation by the induced differentiation of an undifferentiated cell population such as ES/iPS cells using cytokines or the like, there is a likelihood that undifferentiated cells remain in the cells for transplantation. Such residual undifferentiated cells have the risk of forming teratomas, etc., through their own cell division and proliferation at the transplantation site. By contrast, the method for producing somatic cells from animal cells according to the embodiment of the present invention makes it possible to select cells harboring the inducer RNA on the basis of a drug because the drug resistance gene can be co-expressed therewith. Therefore, the cells produced by the method of the present invention can avoid the risk of contamination with undifferentiated cells, teratoma formation, etc., and are thus suitable for medical transplantation.

No virus is used in the method for producing somatic cells from animal cells according to the embodiment of the present invention using a lipofection method. Therefore, genes of stem cells are not damaged, and the produced somatic cells are free from the associated risk of tumorigenesis and as such, can be utilized in clinical therapy.

A method for producing somatic cells from stem cells using viruses requires *E. coli* for the production and proliferation of virus vectors. However, cells produced by the transfer of substances produced using a nonhuman organism are unsuitable for clinical application. By contrast, the method for producing somatic cells from animal cells according to the embodiment of the present invention may transfer RNA into animal cells including iPS/ES cells and the like by using a lipofection method. Since RNA is a chemical substance and can be artificially synthesized, RNA can be produced without the use of an organism such as *E. coli* and is suitable for clinical application.

For example, iPS cells are produced from blood cells in a clean environment of a completely sealed system, and subsequently, somatic cells are produced from the iPS cells in a clean environment of a completely sealed system. In such a case, it is possible to produce cleaner and safer somatic cells.

In addition, the method for producing somatic cells from animal cells according to the embodiment of the present invention makes it possible to produce somatic cells in a short period of time. Therefore, for example, B18R which suppresses cell death resulting from immune response associated with mRNA insertion does not have to be used. Even if such a substance is used, a very dilute concentration thereof is possible.

Example 14

A 12-well dish coated with a solubilized basement membrane preparation (Matrigel, Corning Inc.) was prepared. A feeder-free medium (mTeSR® 1, STEMCELL Technologies Inc.) containing ROCK (Rho-associated coiled-coil forming kinase/Rho-binding kinase) inhibitor (Selleck Chemicals) at a concentration of 10 umol/L was placed in each well. The ROCK inhibitor suppresses cell death.

iPS cells were dispersed in a detachment/separation/dispersion solution for tissues/culture cells (Accutase, Innovative Cell Technologies, Inc.) and seeded to the 12-well dish. The cells to be transfected were seeded at a density of $4 \times 10^5$ cells per well. The area of the bottom of one well was 4 cm². Untransfected control cells were seeded at a density of $2 \times 10^5$ cells per well. Then, the cells were cultured for 24 hours in the feeder-free medium. In this culture, the temperature was 37° C., the $CO_2$ concentration was 5%, and the oxygen concentration was 25% or lower.

1.25 mL of a xeno-free medium (Pluriton, Stemgent Inc.), 0.5 µL of Pluriton Supplement (Stemgent Inc.), and 2 µL of a solution containing B18R recombinant protein at a concentration of 100 ng/µL (eBioscience) were mixed to prepare a transfection medium. Before transfection, the feeder-free medium in each well was replaced with the transfection medium where the cells were cultured at 37° C. for two hours.

Green fluorescent protein (GFP) mRNA (TriLink BioTechnologies, Inc.) was prepared. The mRNA was capped with an anti-reverse cap analog (ARCA), polyadenylated, and substituted with 5-methylcytidine and pseudouridine.

1.5-mL microcentrifuge separation tubes A and 1.5-mL microcentrifuge separation tubes B were each prepared so as to correspond to the number of wells.

62.5 µL of a low-serum medium (Opti-MEM®, Gibco) was placed in each tube A to which 1.875 µL of a reagent for mRNA transfer (Lipofectamine MessengerMAX®, Invitrogen Corp.) was then added and well mixed to prepare a first reaction solution. Then, the tube A was gently tapped at room temperature for ten minutes such that the first reaction solution was mixed.

62.5 µL of a low-serum medium (Opti-MEM®, Gibco) was placed in each tube B to which 500 ng of GFP mRNA (TriLink BioTechnologies, Inc.) was then added and well mixed to prepare a second reaction solution.

The second reaction solution was added to the first reaction solution in the tube A to prepare a mixed reaction solution. Then, the tube A was gently tapped at room temperature for five minutes such that liposomes were formed. Next, the mixed reaction solution was added to each well and left standing overnight at 37° C. As a result, 500 ng of the GFP mRNA was added to each well.

On the next day, the cells were observed under a fluorescence microscope. As a result, as shown in FIGS. 37 and 38, the cells transfected by using MessengerMAX developed color most strongly. As shown in FIG. 39, the cells transfected by using MessengerMAX also exhibited the highest survival rate. This revealed that MessengerMAX is most suitable for mRNA transfer. These results demonstrated that it is possible to express a protein in iPS cells by mRNA transfer using a lipofection reagent and RNA.

Example 15

A 12-well dish coated with a solubilized basement membrane preparation (Matrigel, Corning Inc.) was prepared. A feeder-free medium (mTeSR® 1, STEMCELL Technologies Inc.) containing ROCK (Rho-associated coiled-coil forming kinase/Rho-binding kinase) inhibitor (Selleck Chemicals) at a concentration of 10 µmol/L was placed in each well. The ROCK inhibitor suppresses cell death.

iPS cells were dispersed in a detachment/separation/dispersion solution for tissues/culture cells (Accutase, Innovative Cell Technologies, Inc.) and seeded to the 12-well dish. The cells to be transfected were seeded at a density of $4 \times 10^5$ cells per well. Untransfected control cells were seeded at a density of $2 \times 10^5$ cells per well. Then, the cells were cultured for 24 hours in the feeder-free medium.

1.25 mL of a xeno-free medium (Pluriton, Stemgent Inc.), 0.5 µL of Pluriton Supplement (Stemgent Inc.), and 2 µL of a solution containing B18R recombinant protein at a concentration of 100 ng/µL (eBioscience) were mixed to prepare a transfection medium. Before transfection, the feeder-free medium in each well was replaced with the transfection medium where the cells were cultured at 37° C. for two hours.

Ngn2-T2A-Puro mRNA (TriLink BioTechnologies, Inc.) and green fluorescent protein (GFP) mRNA (TriLink BioTechnologies, Inc.) were prepared. Each mRNA was capped with an anti-reverse cap analog (ARCA), polyadenylated, and substituted with 5-methylcytidine and pseudouridine. Also, the mRNA was purified through a silica membrane and prepared, together with a reagent for mRNA transfer (Lipofectamine MessengerMAX®, Invitrogen Corp.), into a solution containing 1 mmol/L sodium citrate (pH 6) as a solvent. 1.5-mL microcentrifuge separation tubes A and 1.5-mL microcentrifuge separation tubes B were each prepared so as to correspond to the number of wells.

62.5 µL of a low-serum medium (Opti-MEM®, Gibco) was placed in each tube A to which 1.875 µL of a reagent for mRNA transfer (Lipofectamine MessengerMAX®, Invitrogen Corp.) was then added and well mixed to prepare a first reaction solution. Then, the tube A was gently tapped at room temperature for ten minutes such that the first reaction solution was mixed.

62.5 µL of a low-serum medium (Opti-MEM®, Gibco) was placed in each tube B to which 500 ng of Ngn2-T2A-Puro mRNA (TriLink BioTechnologies, Inc.) and 1500 ng of GFP mRNA (TriLink BioTechnologies, Inc.) were then added and well mixed to prepare a second reaction solution.

The second reaction solution was added to the first reaction solution in the tube A to prepare a mixed reaction solution. Then, the tube A was gently tapped at room temperature for five minutes such that liposomes were formed. Next, the mixed reaction solution was added to each well and left standing overnight at 37° C. As a result, 500 ng of the Ngn2 mRNA and 100 ng of the GFP mRNA were added to each well.

As a result of observing the cells one day after the mRNA transfer, as shown in FIG. 40, the cells transfected by using MessengerMAX developed color most strongly.

Then, the medium was completely replaced every day for two days with a neural differentiation medium (N2/DMEM/F12/NEAA, Invitrogen Corp.) containing a ROCK inhibitor (Selleck Chemicals) at a concentration of 10 µmol/L and an antibiotic (puromycin) at a concentration of 1 mg/L to select the mRNA-transfected cells. At day 3, the medium was replaced with a neural differentiation medium (N2/DMEM/F12/NEAA, Invitrogen Corp.) containing a solution containing B18R recombinant protein at a concentration of 200 ng/mL (eBioscience). Then, the medium was replaced in half the amount each time with the same medium as above until day 7.

At day 7, the medium was removed from each well, and the well was washed with 1 mL of PBS. Then, 4% PFA was placed therein and allowed to react with the cells at 4° C. for 15 minutes for fixation. Then, after washing with PBS twice, each primary antibody was diluted with a medium containing 5% CCS and 0.1% Triton in PBS and added at 500 µL/well. The primary antibodies used were a rabbit anti-human Tuj1 antibody (BioLegend 845501) and a mouse anti-rat and human Ngn2 antibody (R&D Systems, Inc.). The rabbit anti-human Tuj1 antibody (BioLegend 845501) was diluted 1/1000 with the buffer, or the mouse anti-rat and human Ngn2 antibody (R&D Systems, Inc.) was diluted 1/75 with the buffer, and DAPI was diluted 1/10000 with the buffer. These dilutions were added to each well and allowed to react at room temperature for one hour. The antibody against Tuj1 is an antibody against β-III Tubulin.

After the reaction at room temperature for one hour, 1 mL of PBS was added to each well and well spread in the well, followed by the discarding of PBS. Again, PBS was added thereto and then discarded. A secondary antibody-containing permeabilization buffer containing a donkey anti-mouse IgG (H+L) secondary antibody-Alexa Fluor® 555 complex (Thermo Fisher Scientific, Inc.) diluted 1/1000 or a donkey anti-rabbit IgG (H+L) secondary antibody-Alexa Fluor® 647 complex (Thermo Fisher Scientific, Inc.) diluted 1/1000 in a permeabilization buffer was added at 500 µL/well and allowed to react at room temperature for 30 minutes.

After the reaction at room temperature for 30 minutes, the cells were washed twice with PBS and observed under a fluorescence microscope to count cells emitting fluorescence.

FIG. 41 is a photograph taken by the observation under a fluorescence microscope of the cells that were cultured for two days after the transfer of the Ngn2-T2A-Puro mRNA by lipofection and the subsequent addition of puromycin, further cultured for five days without the addition of puromycin, and stained with Tuj1. FIG. 42 shows the percentage of TUJ-1-positive cells at day 7 among the cells transfected with the Ngn2-T2A-Puro mRNA by the procedures described above using each transfection reagent. MessengerMAX was found to have four or more times higher than the ability of RNAiMAX or Stemfect to convert iPS cells to the neuronal cells.

FIG. 43 shows photographs taken by the observation under a fluorescence microscope of the cells that were cultured for 6 days after the transfer of the Ngn2-T2A-Puro mRNA by triple lipofection and the subsequent addition of puromycin, further cultured for 16 days without the addition of puromycin, and stained with MAP2 (Sigma Cat #M4403) and vGlut(Synaptic Systems Cat #135 302).

Example 16

A 12-well dish coated with a solubilized basement membrane preparation (Matrigel, Corning Inc.) was prepared. A feeder-free medium (mTeSR® 1, STEMCELL Technologies Inc.) containing ROCK (Rho-associated coiled-coil forming kinase/Rho-binding kinase) inhibitor (Selleck Chemicals) at a concentration of 10 µmol/L was placed in each well.

iPS cells were dispersed in a detachment/separation/dispersion solution for tissues/culture cells (Accutase, Innovative Cell Technologies, Inc.) and seeded to the 12-well dish. The cells to be transfected were seeded at a density of $4 \times 10^5$ cells per well. Untransfected control cells were seeded at a density of $1 \times 10^5$ cells per well. Then, the cells were cultured for 24 hours in the feeder-free medium. In this culture, the temperature was 37° C., the $CO_2$ concentration was 5%, and the oxygen concentration was 25% or lower.

1.25 mL of a xeno-free medium (Pluriton, Stemgent Inc.), 0.5 µL of Pluriton Supplement (Stemgent Inc.), and 2 µL of a solution containing B18R recombinant protein at a concentration of 100 ng/µL (eBioscience) were mixed to prepare a transfection medium with B18R. Also, 1.25 mL of a xeno-free medium (Pluriton, Stemgent Inc.) and 0.5 µL of Pluriton Supplement (Stemgent Inc.) were mixed to prepare a transfection medium without B18R.

Before transfection, the feeder-free medium in each well was replaced with the transfection medium with B18R or the transfection medium without B18R where the cells were cultured at 37° C. for two hours.

Ngn2-T2A-Puro mRNA (TriLink BioTechnologies, Inc.) and GFP mRNA (TriLink BioTechnologies, Inc.) were prepared. The mRNA was capped with an anti-reverse cap analog (ARCA), polyadenylated, and substituted with 5-methylcytidine and pseudouridine.

1.5-mL microcentrifuge separation tubes A and 1.5-mL microcentrifuge separation tubes B were each prepared so as to correspond to the number of wells.

62.5 µL of a low-serum medium (Opti-MEM®, Gibco) was placed in each tube A to which 1.875 µL of a reagent for mRNA transfer (Lipofectamine MessengerMAX®, Invitrogen Corp.) was then added and well mixed to prepare a first reaction solution. Then, the tube A was gently tapped at room temperature for ten minutes such that the first reaction solution was mixed.

62.5 µL of a low-serum medium (Opti-MEM®, Gibco) was placed in each tube B to which 500 ng of Ngn2-T2A-Puro mRNA (TriLink BioTechnologies, Inc.) and 100 ng of GFP mRNA (TriLink BioTechnologies, Inc.) were then added and well mixed to prepare a second reaction solution.

The second reaction solution was added to the first reaction solution in the tube A to prepare a mixed reaction solution. Then, the tube A was gently tapped at room temperature for five minutes such that liposomes were formed. Next, the mixed reaction solution was added to each well and left standing overnight at 37° C. As a result, 500 ng of the Ngn2 mRNA and 100 ng of the GFP mRNA were added to each well. As shown in FIG. 44, singly transfected sample, dually transfected sample, and triply transfected sample were prepared.

Then, the medium was completely replaced every day for two days with a neural differentiation medium (N2/DMEM/F12/NEAA, Invitrogen Corp.) containing a ROCK inhibitor (Selleck Chemicals) at a concentration of 10 μmol/L and an antibiotic (puromycin) at a concentration of 1 mg/L to select the mRNA-transfected cells. At day 3, the medium was replaced with a neural differentiation medium (N2/DMEM/F12/NEAA, Invitrogen Corp.) containing a solution containing B18R recombinant protein at a concentration of 200 ng/mL (eBioscience). Then, the medium was replaced in half the amount each time with the same medium as above until day 7.

At day 7, the medium was removed from each well, and the well was washed with 1 mL of PBS. Then, 4% PFA was placed therein and allowed to react with the cells at 4° C. for 15 minutes for fixation. Then, after washing with PBS twice, each primary antibody diluted with a permeabilization buffer containing 5% CCS and 0.1% Triton X in PBS was added at 50 μL/well and allowed to react at room temperature for one hour. The primary antibodies used were a mouse anti-human Tuj1 antibody (BioLegend 845501) diluted 1:1000 with the permeabilization buffer and a mouse anti-human Ngn2 antibody (R&D Systems, Inc., MAB3314-SP) diluted 1:150 with the permeabilization buffer, and further, DAPI was added thereto at 1:10,000.

One hour later, 1 mL of PBS was added to each well and well spread in the well, followed by the discarding of PBS. Again, PBS was added thereto and then discarded. A secondary antibody-containing permeabilization buffer containing a donkey anti-mouse IgG (H+L) secondary antibody-Alexa Fluor® 555 complex (Thermo Fisher Scientific, Inc., A-21428) diluted 1:1000 or a donkey anti-rabbit IgG (H+L) secondary antibody-Alexa Fluor® 647 complex (Thermo Fisher Scientific, Inc., A31573) diluted 1:1000 in a permeabilization buffer was added at 500 μL/well and allowed to react at room temperature for 30 minutes.

The cells were washed twice with PBS and observed under a fluorescence microscope to count cells emitting fluorescence. As a result, as shown in FIG. 45, the cells singly transfected with the mRNA hardly expressed GFP at day 9. On the other hand, the cells triply transfected with the mRNA expressed GFP even at day 9. This revealed that the mRNA is decomposed in cells and protein expression is transient. FIG. 46 shows an enlarged image of the cells triply transfected with the mRNA expressed GFP at day 7.

The results described above demonstrated that it is possible to induce neuronal cells in a few days after transfection with RNA following seeding of iPS cells. The results also demonstrated that since neuronal cells can be induced in a short period, a medium does not have to contain B18R protein, which is usually used for suppressing cell death resulting from immune response associated with RNA insertion to cells.

REFERENCE SIGNS LIST

10: Separation apparatus
20: Pre-transfer cell solution sending channel
21: Inducer solution sending mechanism
30: Inducer transfer apparatus
31: Post-transfer cell solution sending channel
40: Cell mass production apparatus
50: Reprogramming culture apparatus
51: Cell cluster solution sending channel
60: Division mechanism
70: Expansion culture apparatus
71: Expansion culture solution sending channel
72: Cell cluster solution sending channel
80: Division mechanism
90: Cell cluster delivery mechanism
91: Pre-packaging cell channel
100: Packaging apparatus
110: Cryopreservation solution sending mechanism
200: Container

```
                          Sequence Listing

SEQUENCE LISTING
<110> I Peace, Inc.

<120> Method for manufacturing specific somatic cells from animal cells

<130> A2479AIP0001-PCT

<160> 2

<170> PatentIn version 3.5.1

<210> 1
<211> 1479
<212> DNA
<213> Artificial Sequence

<220>

<223> Inducing factor

<400> 1
atggactaca aggacgacga tgacaagttc gtcaaatctg agactctgga gttgaaggag      60
gaagaggagg tactgatgct gctgggctcg gcttcccccgg cctcggcgac cctgaccccg    120
atgtcctcca gcgcggacga ggaggaggac gaggagctgc gccggccggg ctccgcgcgt    180
gggcagcgtg gagcggaagc cgggcagggg gtgcaggggca gtccggcgtc gggtgccggg    240
ggttgccggc cagggcggct gctgggcctg atgcacgagt gcaagcgtcg cccgtcgcgc    300
tcacgggccg tctcccgagg tgccaagacg gcggagacgg tgcagcgcat caagaagacc    360
```

Sequence Listing

```
cgcaggctca aggccaacaa ccgcgagcgc aaccgcatgc acaacctaaa cgccgcgctg    420
gacgcgctgc gcgaggtgct gcccaccttc cccgaggatg ccaagctcac gaagatcgag    480
acgctgcgct tcgcccacaa ttacatctgg gcgctcaccg agactctgcg cctggcggac    540
cactgcgccg gcgccggtgg cctccagggg gcgctcttca cggaggcggt gctcctgagc    600
ccgggagctg cgctcggcgc cagcggggac agcccttctc caccttcctc ctggagctgc    660
accaacagcc cggcgtcatc ctccaactcc acgtccccat acagctgcac tttatcgccc    720
gctagccccg ggtcagacgt ggactactgg cagcccccac ctccggagaa gcatcgttat    780
gcgcctcacc tgcccctcgc cagggactgt atctctagag agggcagggg aagtcttcta    840
acatgcgggg acgtggagga aaatcccggc ccactcgaga tgaccgagta caagcccacg    900
gtgcgcctcg ccacccgcga cgacgtcccc agggccgtac gcaccctcgc cgccgcgttc    960
gccgactacc ccgccacgcg ccacaccgtc gatccggacc gccacatcga gcgggtcacc   1020
gagctgcaag aactcttcct cacgcgcgtc gggctcgaca tcggcaaggt gtgggtcgcg   1080
gacgacggcg ccgcggtggc ggtctgacc acgccggaga gcgtcgaagc ggggcggtg    1140
ttcgccgaga tcgcccgcg catggccgag ttgagcggtt cccggctggc cgcgcagcaa   1200
cagatggaag gcctcctggc gccgcaccgg cccaaggagc ccgcgtggtt cctggccacc   1260
gtcggcgtct cgcccgacca ccagggcaag ggtctgggca gccgtcgt gctccccgga   1320
gtggaggcgg ccgagcgcgc cggggtgccc gccttcctgg agacctccgc gccccgcaac   1380
ctccccttct acgagcggct cggcttcacc gtcaccgccg acgtcgaggt gcccgaagga   1440
ccgcgcacct ggtgcatgac ccgcaagccc ggtgcctga                         1479
```

<210> 2
<211> 1473
<212> DNA
<213> Artificial Sequence

<220>

<223> Inducing factor

<400> 2

```
atggactaca aggacgacga tgacaagttc gtcaaatctg agactctgga gttgaaggag    60
gaagaggagg tactgatgct gctgggctcg gcttccccgg cctcggcgac cctgaccccg   120
atgtcctcca gcgcggacga ggaggaggac gaggagctgc gccggcgggg ctccgcgcgt   180
gggcagcgtg gagcggaagc cgggcagggg gtgcagggca gtccggcgtc gggtgccggg   240
ggttgccggc cagggcggct gctgggcctg atgcacgagt gcaagcgtcg cccgtcgcgc   300
tcacgggccg tctcccgagg tgccaagacg gcggagacgt gcagcgcat caagaagacc   360
cgcaggctca aggccaacaa ccgcgagcgc aaccgcatgc acaacctaaa cgccgcgctg    420
gacgcgctgc gcgaggtgct gcccaccttc cccgaggatg ccaagctcac gaagatcgag    480
acgctgcgct tcgcccacaa ttacatctgg gcgctcaccg agactctgcg cctggcggac    540
cactgcgccg gcgccggtgg cctccagggg gcgctcttca cggaggcggt gctcctgagc    600
ccgggagctg cgctcggcgc cagcggggac agcccttctc caccttcctc ctggagctgc    660
accaacagcc cggcgtcatc ctccaactcc acgtccccat acagctgcac tttatcgccc    720
gctagccccg ggtcagacgt ggactactgg cagcccccac ctccggagaa gcatcgttat    780
gcgcctcacc tgcccctcgc cagggactgt atcgaggca ggggaagtct tctaacatgc    840
gggggactgg aggaaaatcc cggcccactc gagatgaccg agtacaagcc cacggtgcgc    900
ctcgccaccc gcgacgacgt ccccagggcc gtacgcaccc tcgccgcgc gttcgccgac    960
taccccgcca cgccacacac cgtcgatccg gaccgccaca tcgagcgggt caccgagctg   1020
caagaactct tcctcacgcg cgtcgggctc gacatcggca aggtgtgggt cgcggacgac   1080
ggcgccgcgc tggcggtctg gaccacgccg agagcgtcg aagcggggc ggtgttcgcc   1140
gagatcgccc gcgcatggc cgagttgagc ggttcccggc tggccgcgca gcaacagatg   1200
gaaggcctcc tggcgccgca ccggcccaag gagcccgcgt ggttcctggc caccgtcggc   1260
gtctcgcccg accaccaggg caagggtctg gcagcccg tcgtgctccc cggagtggag   1320
gcggccgagc gcgccggggt gcccgccttc ctggagacct ccgcgcccg caacctcccc   1380
ttctacgagc ggctcggctt caccgtcacc gccgacgtcg aggtgcccga aggaccgcgc   1440
acctggtgca tgacccgcaa gcccggtgcc tga                               1473f
```

---

SEQUENCE LISTING

<160> NUMBER OF SEQ ID NOS: 2

<210> SEQ ID NO 1
<211> LENGTH: 1479
<212> TYPE: DNA
<213> ORGANISM: Artificial Sequence
<220> FEATURE:
<223> OTHER INFORMATION: Inducing factor

<400> SEQUENCE: 1

```
atggactaca aggacgacga tgacaagttc gtcaaatctg agactctgga gttgaaggag    60
gaagaggagg tactgatgct gctgggctcg gcttccccgg cctcggcgac cctgaccccg   120
```

```
atgtcctcca gcgcggacga ggaggaggac gaggagctgc gccggccggg ctccgcgcgt      180
gggcagcgtg gagcggaagc cgggcagggg gtgcagggca gtccggcgtc gggtgccggg      240
ggttgccggc cagggcggct gctgggcctg atgcacgagt gcaagcgtcg cccgtcgcgc      300
tcacgggccg tctcccgagg tgccaagacg gcggagacgg tgcagcgcat caagaagacc      360
cgcaggctca aggccaacaa ccgcgagcgc aaccgcatgc acaacctaaa cgccgcgctg      420
gacgcgctgc gcgaggtgct gcccaccttc cccgaggatg ccaagctcac gaagatcgag      480
acgctgcgct tcgcccacaa ttacatctgg gcgctcaccg agactctgcg cctggcggac      540
cactgcgccg gcgccggtgg cctccagggg gcgctcttca cggaggcggt gctcctgagc      600
ccgggagctg cgctcggcgc cagcggggac agcccttctc caccttcctc ctggagctgc      660
accaacagcc cggcgtcatc ctccaactcc acgtccccat acagctgcac tttatcgccc      720
gctagccccg ggtcagacgt ggactactgg cagcccccac ctccggagaa gcatcgttat      780
gcgcctcacc tgccccctcgc cagggactgt atctctagag agggcagggg aagtcttcta      840
acatgcgggg acgtggagga aaatcccggc ccactcgaga tgaccgagta caagcccacg      900
gtgcgcctcg ccacccgcga cgacgtcccc agggccgtac gcaccctcgc cgccgcgttc      960
gccgactacc ccgccacgcg ccacaccgtc gatccggacc gccacatcga gcgggtcacc     1020
gagctgcaag aactcttcct cacgcgcgtc gggctcgaca tcggcaaggt gtgggtcgcg     1080
gacgacggcg ccgcggtggc ggtctggacc acgccggaga gcgtcgaagc gggggcggtg     1140
ttcgccgaga tcggcccgcg catggccgag ttgagcggtt cccggctggc cgcgcagcaa     1200
cagatggaag gcctcctggc gccgcaccgg cccaaggagc ccgcgtggtt cctggccacc     1260
gtcggcgtct cgcccgacca ccagggcaag ggtctgggca gcgccgtcgt gctccccgga     1320
gtggaggcgg ccgagcgcgc cggggtgccc gccttcctgg agacctccgc gccccgcaac     1380
ctccccttct acgagcggct cggcttcacc gtcaccgccg acgtcgaggt gcccgaagga     1440
ccgcgcacct ggtgcatgac ccgcaagccc ggtgcctga                            1479
```

<210> SEQ ID NO 2
<211> LENGTH: 1473
<212> TYPE: DNA
<213> ORGANISM: Artificial Sequence
<220> FEATURE:
<223> OTHER INFORMATION: Inducing factor

<400> SEQUENCE: 2

```
atggactaca aggacgacga tgacaagttc gtcaaatctg agactctgga gttgaaggag       60
gaagaggagg tactgatgct gctgggctcg gcttccccgg cctcggcgac cctgaccccg      120
atgtcctcca gcgcggacga ggaggaggac gaggagctgc gccggccggg ctccgcgcgt      180
gggcagcgtg gagcggaagc cgggcagggg gtgcagggca gtccggcgtc gggtgccggg      240
ggttgccggc cagggcggct gctgggcctg atgcacgagt gcaagcgtcg cccgtcgcgc      300
tcacgggccg tctcccgagg tgccaagacg gcggagacgg tgcagcgcat caagaagacc      360
cgcaggctca aggccaacaa ccgcgagcgc aaccgcatgc acaacctaaa cgccgcgctg      420
gacgcgctgc gcgaggtgct gcccaccttc cccgaggatg ccaagctcac gaagatcgag      480
acgctgcgct tcgcccacaa ttacatctgg gcgctcaccg agactctgcg cctggcggac      540
cactgcgccg gcgccggtgg cctccagggg gcgctcttca cggaggcggt gctcctgagc      600
ccgggagctg cgctcggcgc cagcggggac agcccttctc caccttcctc ctggagctgc      660
accaacagcc cggcgtcatc ctccaactcc acgtccccat acagctgcac tttatcgccc      720
```

```
gctagcccg  ggtcagacgt  ggactactgg  cagcccccac  ctccggagaa  gcatcgttat    780
gcgcctcacc  tgcccctcgc  cagggactgt  atcgagggca  ggggaagtct  tctaacatgc    840
ggggacgtgg  aggaaaatcc  cggcccactc  gagatgaccg  agtacaagcc  cacggtgcgc    900
ctcgccaccc  gcgacgacgt  ccccagggcc  gtacgcaccc  tcgccgccgc  gttcgccgac    960
tacccgcca   cgcgccacac  cgtcgatccg  gaccgccaca  tcgagcgggt  caccgagctg   1020
caagaactct  tcctcacgcg  cgtcgggctc  gacatcggca  aggtgtgggt  cgcggacgac   1080
ggcgccgcgg  tggcggtctg  gaccacgccg  gagagcgtcg  aagcggggc   ggtgttcgcc   1140
gagatcggcc  cgcgcatggc  cgagttgagc  ggttcccggc  tggccgcgca  gcaacagatg   1200
gaaggcctcc  tggcgccgca  ccggcccaag  gagcccgcgt  ggttcctggc  caccgtcggc   1260
gtctcgcccg  accaccaggg  caagggtctg  ggcagcgccg  tcgtgctccc  cggagtggag   1320
gcggccgagc  gcgccggggt  gcccgccttc  ctggagacct  ccgcgccccg  caacctcccc   1380
ttctacgagc  ggctcggctt  caccgtcacc  gccgacgtcg  aggtgcccga  aggaccgcgc   1440
acctggtgca  tgacccgcaa  gcccggtgcc  tga                                   1473
```

The invention claimed is:

1. A method for inducing pluripotent stem cells, comprising
   (a) culturing somatic cells in a floating culture;
   (b) inducing pluripotent stem cells from the somatic cells in the floating culture, the floating culture comprising a medium; and
   (c) forming colonies of the induced pluripotent stem cells in the floating culture.

2. The method according to claim 1, wherein the medium is not stirred.

3. The method according to claim 1, wherein the medium comprises a gel medium that is gelled with deacetylated gellan gum.

4. The method according to claim 1, wherein the medium is free from a growth factor.

5. The method according to claim 1, wherein the medium contains a growth factor at a concentration of 40% by weight or lower.

6. The method according to claim 1, wherein the medium is free from bFGF.

7. The method according to claim 1, wherein the medium comprises a human ES/iPS culture medium.

8. The method according to claim 1, wherein the medium is free from Tgf-β.

* * * * *